US005817762A

United States Patent [19]
Kleyn et al.

[11] Patent Number: 5,817,762
[45] Date of Patent: Oct. 6, 1998

[54] MAMMALIAN TUB PROTEIN

[75] Inventors: Patrick W. Kleyn, Cambridge; Karen J. Moore, Maynard, both of Mass.

[73] Assignee: Millennium Pharmaceuticals, Inc., Cambridge, Mass.

[21] Appl. No.: 829,553

[22] Filed: Mar. 28, 1997

Related U.S. Application Data

[62] Division of Ser. No. 631,200, Apr. 12, 1996, Pat. No. 5,646,040.

[60] Provisional application Nos. 60/000,604 Jun. 30, 1995, 60/001,273 Jul. 20, 1995, 60/001,444 Jul. 26, 1995, 60/002,759 Aug. 24, 1995, 60/004,424 Sep. 28, 1995 and 60/015,396 Apr. 9, 1996. 63]

[51] Int. Cl.$^6$ .......................... C07K 14/47; C12N 15/11; C12N 15/12
[52] U.S. Cl. ........................................ 530/350; 536/23.5
[58] Field of Search ........................... 530/350; 536/23.5

[56] References Cited

PUBLICATIONS

Friedman, J.M. et al., 1991, "Molecular Mapping of Obesity Genes", Mamm. Genome 1:130–144.
Bray, G.A., 1992, "Genetic, Hypothalamic and Endocrine Features of Clinical and Experimental Obesity", Prog. Brain Res. 93:333–341.
Friedman, J.M. and Leibel, R.L., 1992, "Tackling a Weighty Problem", Cell 69:217–220.
Coleman, D.L. and Eicher, E.M., 1990, "Fat (*fat*) and Tubby (*tub*): Two Autosomal Recessive Mutations Causing Obesity Syndromes in the Mouse", J. Hered. 81:424–427.
Jones, J.M. et al., 1992, "Localization of Insulin–2 (*Ins–2*) and the Obesity Mutant Tubby (*tub*) to Distinct Regions of Mouse Chromosome 7", Genomics 14:197–199.
Warden, C.H. et al., 1993, "Coincidence of Genetic Loci for Plasma Cholesterol Levels and Obesity in a Multifactorial Mouse Model", J. Clin. Invest. 92:773–779.
Nishina, P.M. et al., 1994, "Characterization of Plasma Lipids in Genetically Obese Mice: The Mutants Obese, Diabetes, Fat, Tubby, and Lethal Yellow", Metabolism 43:549–553.
Nishina, P.M. et al., 1994, "Atherosclerosis in Genetically Obese Mice: The Mutants Obese, Diabetes, Fat, Tubby, and Lethal Yellow", Metabolism 43:554–558.
Seldin, M.F. et al., 1994, "Glycogen Synthase: A Putative Locus for Diet–Induced Hyperglycemia", J. Clin. Invest. 94:269–276.
West, D.B. et al., 1994, "Genetics of Dietary Obesity in AKR/J X SWR/J Mice: Segregation of the Trait and Identification of a Linked Locus on Chromosome 4", Mamm. Genome 5:546–552.
Warden, C.H. et al., 1995, "Identification of Four Chromosomal Loci Determining Obesity in a Multifactorial Mouse Model", J. Clin. Invest. 95:1545–1552.
Samuelson, L.C. et al., 1995, "Localization of the Murine Cholecystokinin A and B Receptor Genes", Mamm. Genome 6:242–246.

Ohlemiller, K.K. et al., 1995, "Cochlear and Retinal Degeneration in the *tubby*Mouse", Neuroreport 6:845–849.
Heckenlively, J.R. et al., 1995, "Mouse Model for Usher Syndrome: Linkage Mapping Suggests Homology to Usher Type I Reported at Human Chromosome 11p15", Proc. Natl. Acad. Sci. USA 92:11100–11104.
Chung, W.K. et al., 1996, "Molecular Mapping of the Tubby (*tub*) Mutation on Mouse Chromosome 7", Genomics 32:210–217.
Genbank Accession No. X69827 NCBI Entrez Record.
Vambutas, V. and Wolgemuth, D.J., 1994, "Identification and Characterization of the Developmentally Regulated Pattern of Expression in the Testis of a Mouse Gene Exhibiting Similarity to the Family of Phosphodiesterases", Biochim. Biophys. Acta 1217:203–206.
Genbank Accession No. Z48334 NCBI Entrez Record.
Wilson, R. et al., 1994 "2.2 Mb of Contiguous Nucleotide Sequence from Chromosome III of *C. elegans*", Nature 368:32–38.
Genbank Accession No. Z50688 NCBI Entrez Record.
Genbank Accession No. H92408 NCBI Entrez Record.
Bray, GA, 1989, "1989 McCollum Award Lecture. Genetic and Hypothalamic Mechanisms for Obesity–Finding the Needle in the Haystack" Am. J. Clin. Nur. 50:891–902.
Borjeson, M., 1976, "The Aetiology of Obesity in Children", Acta. Paediatr. Scand. 65:279:287.
Chen, H. et al., "Evidence that the Diabetes Gene Encodes the leptin Receptor: identification of a Mutation in the Leptin Receptor Gene in *db/db* Mice", Cell 84:491–495.
Coleman, D.L., 1978, "Obese and Diabetes: Two Mutant Genes causing Diabetes–Obesity Syndromes in Mice", Diabetologia 14:141–148.
Grundy and Barnett, 1990, Dis. Mon. 36:641–731.
Heckenlively, 1988, in Retinitis Pigmentosa, Heckenlively, ed., Lippincott, Philadelphia, pp. 221–235.
Herberg and Coleman, 1977, "Laboratory Animals Exhibiting Obesity and Diabetes Syndromes", Metabolism 26:59–59.
Kleyn, P. et al., 1996, "Identification and Characterization of the Mouse Obesity Gens *tubby*: A Member of a Novel Gene Family", Cell 85:281–290.
Knoll, J.H. et al., 1993, Am. J. Med. Genet. 46:2–6.
Marshall, E., 1995, "Gene Therapy's Growing Pains", Science 269:1050–1055.
Michaud, E. et al., 1994, "Differential Expression of a New Dominant Agouti Allele ($A^{i s p y}$) is Correlated with Methylation State and is Influenced by Parental Lineage", Genes Devel. 8:1463–1472.

(List continued on next page.)

*Primary Examiner*—Johnny F. Railey II
*Attorney, Agent, or Firm*—Pennie & Edmonds

[57] ABSTRACT

The present invention relates to the identification of novel nucleic acid molecules and proteins encoded by such nucleic acid molecules or degenerate variants thereof, that participate in the control of mammalian body weight. The nucleic acid molecules of the present invention represent the genes corresponding to the mammalian tub gene, a gene that is involved in the regulation of body weight.

29 Claims, 29 Drawing Sheets

OTHER PUBLICATIONS

Moll, et al., 1991, "The Genetic and Environmental Sources of Body Mass Index Variability: The Muscatime Ponderosity Family Study", Am. J. Hum. Gen. 49:1243–1255.

Naggert, J. et al., 1995, "Hyperproinsulinaemia in Obese fat/fat Mice Associated with a Carboxypeptidase E Mutation which Reduces Enzyme Activity", Nature Genetics 10:135–141.

Noben–Trauth, K. et al., 1996, "A Candidate Gene for the Mouse Mutation Tubby", Nature 380:534–538.

Leibel, R. et al., 1990, in "Genetic Variation and Nutrition in Obesity", Simopoulos AP, Childs B (eds): Genetic Variation and Nutrition. World Rev. Nutr. Diab. basel, Karger, Switzerland, Vol.63, pp. 90–101.

Stunkard, 1990, "The Body–Mass Index of Twins Who Have Been Reared Apart", N. Engl. J. Med. 322:1483–1487.

Tartaglia, L.A. et al., 1995, "Identification and Expression Cloning of a Leptin Receptor", Cell 83:1263–1271.

Zhang, Y et al., 1994, "Positional Cloning of the Mouse Obese Gene and its Human Homologue", Nature 372:425–432.

```
                GGATGCGGCCCGGGGGCCCGGAGAGTTGAGCAGGGTCCCCGGCCCAGCCCCGAGCGGTCCCGGCCACCCGAGCCGCAG
                CTGCAGGATTCGGCACGAGCAGCGGTCGGGCCGGGGA

M   T   S   K   P   H   S   D   W   I   P   Y   S   V                              14
      ATG ACT TCC AAG CCG CAT TCC GAC TGG ATT CCT TAC AGT GTC                              42

L   D   D   E   G   S   N   L   R   Q   K   L   D   R   Q   R   A   L                   34
  CTA GAT GAT GAG GGC AGC AAC CTG AGG CAG AAG CTC GAC CGG CAG CGG GCC CTG TTG             102

E   Q   K   Q   K   K   R   Q   E   P   L   M   V   Q   A   N   A   D   G               54
  GAA CAG AAG CAG AAG AAG CGC CAA GAG CCC TTG ATG GTA CAG GCC AAT GCA GAT GGA             162

R   P   R   S   R   R   A   R   Q   S   E   E   Q   A   P   L   V   E   S   Y           74
  CGG CCC CGG AGT CGG CGA GCC CGG CAG TCA GAG GAG CAA GCC CCC CTG GTG GAG TCC TAC         222

L   S   S   G   S   T   R   P   P   A   P   A   P   V   Q   D   S   I   A   S   V       94
  CTC AGC AGT GGC AGC AGC ACC CGC CCA CCA GCA CCA GCT TCA GAG GCC TCG ATT GCC AGT GTA     282

Q   L   G   A   T   R   P   A   G   A   S   K   S   K   K   G   A                      114
  CAG CTG GGA GCC ACC CGC CCA GCT GCT TCA GCC AAG TCC AAA AAG GGA GCG GCT                 342

A   S   G   G   Q   G   A   P   R   K   E   K   K   H   K   G   T                      134
  GCA TCT GGG GGC CAG GGT GCC CCT AGG AAG GAG AAG AAG CAT AAA GGC ACC                     402
```

```
V   D   P   T   D   L   S   R   G   G   D   S   Y   I   G   K   L   R   S   N    334
GTG GAC CCA ACA GAC TTG TCT CGG GGA GGC GAT AGC TAT ATC GGG AAA TTG CGG TCC AAC  1002

L   M   G   T   K   F   T   V   Y   D   N   G   V   N   P   Q   K   A   S   S    354
CTG ATG GGC ACC AAG TTC ACC GTT TAT GAC AAT GGC GTC AAC CCT CAG AAG GCA TCC TCT  1062

S   T   L   E   S   G   T   L   R   Q   E   L   A   A   V   N   P   Q   A   T    374
TCC ACG CTG GAA AGC GGA ACC TTG CGC CAG GAG CTG GCA GCG GTG AAC CCT CAG GCA TCC  1122

V   L   G   F   K   G   P   R   K   M   S   V   I   V   P   G   M   N   M   V    394
GTC CTA GGC TTC AAG GGA CCT CGG AAG ATG AGT GTG ATC GTC CCA GGC ATG AAC ATG GTT  1182

H   E   R   V   C   I   R   P   N   E   H   E   T   L   A   R   W   Q           414
CAT GAG AGA GTC TGT ATC CGC CCC AAT GAA CAT GAG ACC CTG TTA GCA CGC TGG CAG      1242

N   K   N   T   E   S   I   E   L   Q   N   K   T   P   V   W   N   D           434
AAC AAG AAC ACG GAG AGC ATC ATT GAG CTG CAG AAC AAG ACG CCA TGG AAT GAT          1302

T   Q   S   Y   V   L   G   R   H   G   R   V   T   Q   A   S   V   K   N   F    454
ACA CAG TCC TAT GTA CTT CAC GGC CGT GTC ACA CAG GCT TCT GTG AAG AAC TTC          1362

Q   I   H   G   N   D   P   D   Y   I   V   M   Q   F   G   R   V   A   E        474
CAG ATC CAC GGC AAT GAC CCG TAC ATC GTC ATG CAG CAG TTT GGC CGG GTA GCA GAA      1422
```

FIG.6C

```
        D   V   F   T   M   D   Y   N   Y   P   L   C   A   L   Q   A   F   A   I   A    494
        GAT GTG TTC ACC ATG GAT TAC AAC TAC CCA CTG TGT GCA CTG CAG GCC TTC GCC ATT GCT   1482

L   S   S   F   D   S   K   L   A   C   E   *                                    505
        CTG TCC AGC TTT GAC AGC AAG CTG TGC GAG TAG AGGCCCCCACTGCCGTTAGGTGGCCAGTC          1515

CGGAGTGGAGCTTGCCTGCCAAGACAGGCCTGCCTACCCTCTGTTCATAGGCCCTCTATGGGCTTTCTGGTCTGA

CCAACCAGAGATTGGTTTGCTCTGCCTCTGCTGCTTGA
```

FIG.6D

```
tubgenomic    ACGGCAATGA  CCTTGAGTGT  TGCCACTCCC  TGTTTTTGAT
B6genomic     ACGGCAATGA  CCGTGAGTGT  TGCCACTCCC  TGTTTTTGAT
tubcdna       ACGGCAATGA  CCTTGAGTGT  TGCCACTCCC  TGTTTTTGAT
B6cdna        ACGGCAATGA  CC::::::::  ::::::::::  ::::::::::
1            ********             ***  ******** tubgenomic    GTTGTACGCA  TGGTGCCCAG  CCCCCACCCC  ACCCCCAATC
B6genomic     GTTGTACGCA  TGGTGCCCAG  CCCCCACCCC  ACCCCCAATC
tubcdna       GTTGTACGCA  TGGTGCCCAG  CCCCCACCCC  ACCCCCAATC
B6cdna        ::::::::::  ::::::::::  ::::::::::  ::::::::::
41           ********  ******  ******  ******** tubgenomic    CCCTGATCTG  GTCCATATCA  GCCAGTGATG  GGATGTGGGT
B6genomic     CCCTGATCTG  GTCCATATCA  GCCAGTGATG  GGATGTGGGT
tubcdna       CCCTGATCTG  GTCCATATCA  GCCAGTGATG  GGATGTGGGT
B6cdna        ::::::::::  ::::::::::  ::::::::::  ::::::::::
#81           **********  **********  **********  **********
```

FIG. 7A

```
tubgenomic  ATATGGCTTT  TGTTAGAACT  TTCTAACTGT  AGTGATCTAG
B6genomic   ATATGGCTTT  TGTAAGAACT  TTCTAACTGT  AGTGATCTAG
tubcdna     ATATGGCTTT  TGTTAGAACT  TTCTAACTGT  AGTGATCTAG
B6cdna      ..........  ..........  ..........  ..........
            ::::::::::  ::: ::::::  ::::::::::  ::::::::::
121        ********  * ****  ******  ******** tubgenomic  AGTCCTGCCC  CTAGTGCCCT  GCATGTCTGG  GGCTTGGGAA
B6genomic   AGTCCTGCCC  CTAGTGCCCT  GCATGTCTGG  GGCTTGGGAA
tubcdna     AGTCCTGCCC  CTAGTGCCCT  GCATGTCTGG  GGCTTGGGAA
B6cdna      ..........  ..........  ..........  ..........
            ::::::::::  ::::::::::  ::::::::::  ::::::::::
161        ********  ******  ******  ******** tubgenomic  TACCCTTTAA  ATGGATGTCT  TTTCTCTCCT  GGGCCCTGCT
B6genomic   TACCCTTTAA  ATGGATGTCT  TTTCTCTCCT  GGGCCCTGCT
tubcdna     TACCCTTTAA  ATGGATGTCT  TTTCTCTCCT  GGGCCCTGCT
B6cdna      ..........  ..........  ..........  ..........
            ::::::::::  ::::::::::  ::::::::::  ::::::::::
#201        **********  **********  **********  **********
```

FIG.7B

```
tubgenomic   GTCTGTGTGC  ATCTCCCCCC  TTCACCCTCT  TGCTTCATAA
B6genomic    GTCTGTGTGC  ATCTCCCCCC  TTCACCCTCT  TGCTTCATAA
tubcdna      GTCTGTGTGC  ATCTCCCCCC  TTCACCCTCT  TGCTTCATAA
B6cdna       ::::::::::  ::::::::::  ::::::::::  ::::::::::

241         ********  ******  ******  ******** tubgenomic   TGTTTCTCTT  GAACCTTTGT  TTTGTTCATC  CTTTCGATCT
B6genomic    TGTTTCTCTT  GAACCTTTGT  TTTGTTCATC  CTTTCGATCT
tubcdna      TGTTTCTCTT  GAACCTTTGT  TTTGTTCATC  CTTTCGATCT
B6cdna       ::::::::::  ::::::::::  ::::::::::  ::::::::::

281         ********  ******  ******  ******** tubgenomic   CTTTGGCATT  TCTGCTTTCT  CCTTCCCTCT  TGTGGCCCAT
B6genomic    CTTTGGCATT  TCTGCTTTCT  CCTTCCCTCT  TGTGGCCCAT
tubcdna      CTTTGGCATT  TCTGCTTTCT  CCTTCCCTCT  TGTGGCCCAT
B6cdna       ::::::::::  ::::::::::  ::::::::::  ::::::::::

```
tubgenomic  GTCTTACCTG GTCTCCCTGT CTCCACCATT CTTGCTTGTG
B6genomic   GTCTTACCTG GTCTCCCTGT CTCCACCATT CTTGCTTGTG
tubcdna     GTCTTACCTG GTCTCCCTGT CTCCACCATT CTTGCTTGTG
B6cdna      ::::::::::  ::::::::    ::::::::   ::::::::
361        ********  ****    ****   ****** tubgenomic  CATTCCACAG CGGACTACAT CGTCATGCAG TTTGGCC
B6genomic   CATTCCACAG CGGACTACAT CGTCATGCAG TTTGGCC
tubcdna     CATTCCACAG CGGACTACAT CGTCATGCAG TTTGGCC
B6cdna      CATTCCACAG CGGACTACAT CGTCATGCAG TTTGGCC
#401        ********** ********** ********** *******
```

FIG. 7D

```
AGCCCNCCGGTCCCAGAGCCGCAGCCGCCACCGCCCCCGCCCCCGAGAGAC                              TGGCGTGCAGCAGGGGCTCGGGGGCCC
                                                                                 CCCCGCCCCGGAGCTGAGCAGCCCCCTCCGGGC

M   T   S   K   P   H   S   D   W                                                                      9
              ATG ACT TCC AAG CCG CAT TCC GAC TGG                                                                    27

I   P   Y   S   V   L   D   D   E   G   R   N   L   R   Q   Q   K   L   D   R                                     29
  ATT CCC TAC AGT GTC TTA GAT GAT GAG GGC AGA AAC CTG AGG CAG CAG AAG CTT GAT CGG                                    87

Q   R   A   L   L   E   Q   K   Q   K   K   R   Q   E   P   L   M   V   Q                                         49
  CAG CGG GCC CTG CTG GAG CAG AAG CAG AAG AAG CGC CAG GAG CCC CTG ATG GTG CAG                                       147

A   N   A   D   G   R   P   R   S   S   R   A   R   Q   S   E   E   Q   A   P                                     69
  GCC AAT GCA GAT GGG CGG CCC CGG AGC AGC CGG GCC CGG CAG TCA GAG GAA CAA GCC CCC                                   207

L   V   E   S   Y   L   S   S   G   A   T   R   P   T   S   Y   Q   V   E   A   D                                 89
  CTG GTG GAG TCC TAC CTC AGC AGT GGC GCC ACG CGC CCA ACA AGC TAC CAA GTT CAA GAG GCC GAC                           267

S   L   A   S   V   Q   L   G   G   Q   L   G   A   P   A   S   A   K   R                                        109
  TCA CTC GCC AGT GTG CAG CTG GGA GCC CCA GCA GCA GCC TCA GCC AAG AGA                                               327

T   K   A   A   A   T   A   G   G   G   Q   G   A   A   R   K   E   K   K   G                                    129
  ACC AAG GCC GCA GCT ACA GCA GGG GGC CAG GGT GCC GCT AGG AAG GAG AAG AAG GGA                                       387
```

| | | | | | | | | | | | | | | | | | | | | |
|---|---|---|---|---|---|---|---|---|---|---|---|---|---|---|---|---|---|---|---|---|
| K | H | K | G | T | S | G | P | A | A | L | A | E | D | K | S | E | A | Q | G | 149 |
| AAG | CAC | AAA | GGC | ACC | AGC | GGG | CCA | GCA | GCA | CTG | GCA | GAA | GAC | AAG | TCT | GAG | GCC | CAA | GGC | 447 |
| P | V | Q | I | L | T | V | G | Q | S | D | H | A | Q | E | T | E | A | | | 169 |
| CCA | GTG | CAG | ATT | CTG | ACT | GTG | GGC | CAG | TCA | GAC | CAC | GCC | CAG | GAG | ACG | GAG | GCA | | | 507 |
| A | G | G | P | S | Q | G | A | D | R | L | A | M | T | Q | R | K | G | | | 189 |
| GCT | GGT | GGG | CCA | AGC | CAG | GGG | GCA | GAC | CGT | CTC | GCC | ATG | ACG | CAG | AGG | AAG | GGC | | | 567 |
| I | S | S | M | S | F | D | E | E | D | E | E | N | S | R | K | S | S | | | 209 |
| ATC | TCC | AGC | ATG | AGC | TTT | GAC | GAG | GAG | GAT | GAG | GAG | AAT | AGC | AGG | AAG | TCC | AGC | | | 627 |
| S | Q | L | N | S | A | T | R | P | S | S | A | T | S | R | K | V | R | | | 229 |
| TCC | CAG | CTA | AAT | AGT | GCT | ACT | CGC | CCC | AGC | TCT | GCT | ACC | AGC | AGG | AAG | GTC | AGG | | | 687 |
| E | A | S | A | P | S | R | P | T | A | P | E | Q | P | D | V | E | V | Q | | 249 |
| GAG | GCA | TCA | GCC | CCT | AGC | CGC | CCA | ACA | GCT | CCA | GAG | CAA | CCA | GAC | GTG | GAG | GTC | CAG | | 747 |
| D | L | E | E | F | A | L | R | P | A | P | Q | G | I | T | I | K | C | R | I | 269 |
| GAT | CTT | GAG | GAG | TTT | GCA | CTG | AGG | CCG | GCC | CCC | CAG | GGT | ATC | ACC | ATC | AAA | TGC | CGC | ATC | 807 |
| T | R | D | K | K | G | M | D | R | G | M | Y | P | T | Y | F | L | H | L | D | 289 |
| ACT | CGG | GAC | AAG | AAA | GGG | ATG | GAC | CGG | GGC | ATG | TAC | CCC | ACC | TAC | TTT | CTG | CAC | CTG | GAC | 867 |

```
R   E   D   G   K   K   V   F   L   L   A   G   R   K   K   S   K   T                         309
CGT GAG GAT GGG AAG AAG GTG TTC CTC CTG GCG GGA AGG AAG AGA AGT AAA ACT                         927

S   N   Y   L   I   S   N   D   G   G   R   D   L   S   Y   I                                 329
TCC AAT TAC CTC ATC TCT GTG GAC CCA ACA GAC TTG TCT CGA GGA GAC AGC TAT ATC                     987

G   K   L   R   S   N   L   M   G   T   K   F   T   V   Y   D   N   G   V   N                 349
GGG AAA CTG CGG TCC AAC TTG ATG GGC ACC AAG TTC ACT GTT TAT GAC AAT GGA GTC AAC                1047

P   Q   K   A   S   S   T   L   E   S   G   T   L   R   Q   E   L   A   A                     369
CCT CAG AAG GCC TCA TCC ACT TTG GAA AGT GGA ACC TTA CGT CAG GAG CTG GCA GCT                    1107

V   C   Y   E   T   N   V   L   G   F   K   G   P   R   K   M   S   V   I   V                 389
GTG TGC TAC GAG ACA AAC GTC TTA GGC TTC AAG GGG CCT CGG AAG ATG AGC GTG ATT GTC                1167

P   G   M   N   M   V   H   E   R   V   S   I   R   P   R   N   E   H   E   T                 409
CCA GGC ATG AAC ATG GTT CAT GAG AGA GTC TCT ATC CGC CCC CGC AAC GAG CAT GAG ACA                1227

L   A   R   W   Q   N   K   N   T   E   S   I   I   E   L   Q   N   K   T                     429
CTG GCA CGC TGG CAG AAT AAC ACG GAG ATC ATC GAG CTG CAA AAC AAG ACA                            1287

P   V   W   N   D   D   T   Q   S   Y   V   L   N   F   H   G   R   V   T   Q                 449
CCT GTC TGG AAT GAT GAC ACA CAG TCC TAT GTA CTC AAC TTC CAT GGG CGC GTC ACA CAG                1347
```

FIG. 9C

```
 A   S   V   K   N   F   Q   I   I   H   G   N   D   P   D   Y   I   V   M   Q     469
GCC TCC GTG AAG AAC TTC CAG ATC ATC CAT GGC AAT GAC CCG GAC TAC ATC GTG ATG CAG    1407

F   G   R   V   A   E   D   V   F   T   M   D   Y   N   Y   P   L   C   A   L     489
TTT GGC CGG GTA GCA GAG GAT GTG TTC ACC ATG GAT TAC AAC TAC CCG CTG TGT GCA CTG    1467

Q   A   F   A   I   A   L   S   S   F   D   S   K   L   A   C   E   *             506
CAG GCC TTT GCC ATT GCC CTG TCC AGC TTC GAC AGC AAG CTG GCG TGC GAG TAG AGGCCTC    1528

TTCGTGCCCTTTGGGGTTGCCCAGCCTGGAGCGGAGCTTGCCTGCCCTGTGGAGACAGCCCTGCCTATCCTCTGTA      1607

TATAGGCCTTCCGCCAGATGAAGCTTTGGCCCCTCAGTGGGCTCCCTGGCCCAGCCAGCCAGGAACTGGCTCCTTTGCT   1686

CTGCTACTGAGGCAGGAGTAGTAGTGGGGTGTGTTGAAGGATTGAGAATTAATTCTTCCATGCCAC                1765

GAGGATCAACACACACTCCCACCCTTGGGTAGTAAGTGGTTGTGTGTNAGTGGTACTTTACCAAAGTTGAGCAACTC     1844

TTCCAAGCTTGGGAAAGGGCCGCAAAAGGCATTAGGAGGGGAG                                       1888
```

FIG. 9D

```
AGCCTACAGTTTAAACAGTCGACTCTAGACTTAATTAAGGNTCCGGNGCG
CCCCGGGTACCGAGCTCGGTCTCCACCCACTGCCTGTTTCTCTCTCC
ATCTGGGATGTTTCCTGAGCAGTTCAAGAGGCCGACTCACTGCCAGTG
TGCAGCTGGGAGCGCGCCAACCAGCTTCAGCCAAGAGAACC
AAGGGCGGCAGCTACAGCAGGGGCGGCCGCGCTAGGAAGGAGAA
GAAGGGAAAGCACACAAAGGTCAGCTCACATTCTCTACAGCCCTGCCCAGCA
GGCCTGGCCTCCACTGTAGGGCTGGGAAGTTTGTCCTCCTGACTTGGA
GGGGAGGGATAGAACAGCCTCAGGAAGACAGACTGCCACTCTG
GGCACCCCCCTCAGGTGCCTCACAGGCCTCATCTAGCTTGGGAGGTGCCTG
GGCTGCCTCTGGGTCTGGGCATGCCTACCAACACTGCCAGGAAGTGAAGT
CCTGCTCAGCTTTGGCCCAGAACCACCGTCCCNANCTTNAGTTACTTTGG
CCTTGAGGAACCTTTATNATGACCCNTNAAGGAGGATTTTAACCAAGCT
GGATT
```

FIG.10A

```
TTCAAGGGCCAAAGTTTTTAATGATGTATGGGAGTTAATGAAGGNGGTA
TGTGGGTNTGTTNGNGGAAGAAAACACCAGCATTGATGGTTGTAGNTGKT
GGTGTCCAKGAATGATTGCTGGCCTTGCCTATGGTNTGGATCAGTCCTTG
TTNTCCCATCTTGTTTTTTCCCATGTGCAGTGTGGTTTTTGTAGATGGCTG
CCGTCTGCTTTAAAGGACGTGAGGTGTGTAAACAACCCTCGCAATTA
ATTTGGGGAAGAGCAGAAGAAATGAAGCCCAACATCCCTTACTAGCTTA
CCAGTGTTAACAGGCTGGTGCAATCATTAGTTTTATAAAAATCAGTTTT
GCAAATAAAGTTTTGCAGAGGGTTTCCCACTCTTCCCTCCTCATCCCTTCA
TGGACGTCTGAGAATCCAGGCCCTCCAGGCACCAGCAGCCTCCTGGATGTAACTCA
GGCGTGTCCGTGGCCTGCAGGCCCAAGCCCAGTGCCAGATTCTGACTGGCCAGTCA
ACAAGWCTGAGGCCCAGGACGCAGGGAGACGGCCAGCTGGTGGGGCGAACGCC
GACCACGCCCAGGATCTCCGTKCCCACGATGCAGAGGAAGGTGAGCCCCATG
CAGCGGGCAGGATCTCCGTKCCCACGATGCAGAGGAAGGTGAGCCCCATG
GGGGCCCAGTGGATGATACCCCAAAACTCAGTCGTTCTCAGATGCACCT
TTCTCTGGAGCATGGNCTTCCTGTGTCCAAACCCCTCCTGCAATGGT
GGGTGAGGGTGGGGCACACTTCGGAGACAATNAGAAACTCTTAGGCAGG
GNCCCTGCTAAGGCCCCCAGGGAGGCC
```

FIG.10B

```
TTAAACAGTCGACTCTAGACTTAATTAAGGATCCGGCGCGCCCCGGTA
CCGAGCTCAGTGCAGGCCTTGATACACAAGAGACAGTGGTAGGGTGSCTG
CTAGGTAGTGGGGTAATGTAGGACTGAGCTGAAACTGGGTGGTGGGGAT
ATATCCTGAGGATTGTGGCCAGCCCCGGCTCATGTGTGTACCTGAGAGAA
TATCCTTTTATATCTGGACAGTGTGGGAATATATGTGTGAATGGGAGTC
TATATGTGTAGATATGGCTAAGAGTGTGTCATAAGTTTGTGGGTACA
GGTGAGTCAGTGTCTGAACATGAGTATGTGACCATGTGTATTTCAGGGGC
AGGGTAGACTTCCCTCATTCATCCCTTCTCTCTCCTTGCCCAGG
CATCTCCAGCAGCATGAGCTTTGACGAGGATGAGGAGGATGAGGAGGAGA
ATAGCTCCAGCAGGAAGTCCGTCAGGGTGAGTGAGTGCATCCACAGCAG
ACTAGCAGGAAGTCCGTCAGGGTTAGAGGTGGACTGCATGTGAAGAGATG
TTTTGGAGGACTGCTCATCCGTTAGAGGTGGACTGCATGTGAAGAGATG
GACTCGTATGCCTTAGGAGGTTCTGCTGCCCTTGCTGCAGGTCCCTAC
CTTGCCTCCTAACCTCTCAGCTCAGCCAGGTGACCTGCAGGGTGATGTATGGGGGA
GATGCAGTTGGACAGGATGACCTCTGAGGACCTCCCGTATCTCCCATCTC
CACCTCTAGGAACTGTTGAGGCCAGGCCCCAATCCCAGAGATCCTTCCCTCTCCCAC
AGGCCAGGCTGGCCAGGCCCCAATCCCAGAGATCCTTCCCTCTCCCAC
CGCCACGTTAGGAGGCAGATTGGATCCAGAGCAGCACCACCACCAATTTGGCTGCT
TAGGGTCCTTGGGCTCAGGCACCTATTCTGCATCCATAGAGGCAGC
CTCAGCCCCTAGCCACCAACAGCTCCAGAGCAACCAGTGGACGTTGAGGTCC
AGGATCTTGAGGAGTTTGCACTCGGGACAGTTGCACTATCACCATC
AAATGCCGCATCACTCGGGACAAGAAAGGGATGGACCGGGCATGTACCC
```

FIG.10C

CACCTACTTTCTGCACCTGGACCGTGAGGATGGGAAGAAGAGTAAGGTTGG
TCTGGGCATGTTATCATCTAGGCTTTACAGCCCTTTGAAATCCTAGGGGC
TGAAATGTGACTGGAAGTCTCATATCTACCGCTCTCAGTTCCTCA
AAGAAACTGCCTTCGTGTCTGTGGTCTGTGTGCACATCTTTGTGTTTCCAGTG
CATTTGTGTGTGAGTGCGTTTGGGAGCTGTGCAACGAGAG
AGTCTGTGTGAGTGGCTCTCATGACTGTGCAGACCAGAGGCTGAGTCT
GGAATATGACCTCATTCCACTCCCCCAAGGTGTTCCTCCTGGCGGAAGA
AGAGAAAGAGTAAAACTTCCAATTACCTCTGTGACCCAACA
GACTTGTCTCGAGGAGGGACAGCTATATCGGGAAACTGCGGGTACTAGC
ATTCCCCAGGAAGCAGGGAGTGGGAGGGGAGGAGCAAGCTG
TCTGTAGAGGCCTGAATCTTCCTGAAGGAGATCTAGGCCAGGATGGAT
ACTCTCCCAGGATCCCTCTCTGATAATCACATCACAACTGAGCCTATGTC
TATGCCAGCCTAGACCCAGGAGACTTGGAGATGGAGACTCACACCCGACCCC
AAGCTGTTCCCAGGAGGTGGGTGCAGGCCCACCAAGAGTGATGGATCCAA
CCCCAGGGTGTCACTGATAACGCAGGCCCACCATGGAAGAGTTGCCTTGGC
TCCATGGTCAAATGCCAAGGACAGGCTGAGAGTGAGCTCGGTACCCGGG
GGCGCKCCGATCCCTTAATTAAGTCTAGAGTCGACTGTTTAAG

FIG.10D

GATTTAGNGGAACACAGCANCTTGNGGTGGGANGGCAGTGGTGAAGGGG
CAGGAAGGCTCTGAGCCTAGGCCTCCAGTGGGGCAGTGGGGAGGTAGG
GTTTGCTGAGGAACTGAGTACCAGATTTGGGAGCATAAATAAAGATGAG
AGGTCAGGAGCTAAAGCTGGAGATGGGGCTGAGACTGAGACTTAGGCTGGC
TGCCGACAGAGGAGATCTCATCCTCTGTTTGCTCACCTCCATGAGGAGAACTC
CTGTCTTATCAGATGCCATTCTGTTTGCTCACCTCCATGAGGAGAACTC
CCATGTTCCCCAGATAAATCTYCTGAAGATGCACTTGAGTCAACTCAGAGCAAGTCC
ATTGCTCTCACTGAACTGAAATGCACTTGAGTCAACTCAGAGCAAGTCC
AGGCCTTCTGCCCACGAAGTGTCTTCAAAGATGTGGATTCAGTGAGCAGT
ATGCCTCCCTGGGCCTGCTCCTGTTCCAGCCCAGAATGTTTTGCAGGCTC
CTCATAGAGACAGAGACGATGAGCTGTCCCTGCTTCTGGGCAGAGGGTGCA
TGACTCTATACTGATTGTGCCTTTATTTCAGGTCCAACTTGATGGGCACC
AAGTTCACTGTTTATGACAATGGAGTCAACCCTCAGAAGCCTCATCCTC
CACTTTGGAAAGTGGAACCTTACGTCAGGCTGGCAGCTGTGTGCTACG
TGAGTCCTAGGTTCGGGGTCTCTGATTTCCAAGGTAGATATGAAATCCA
GGACTTGATGCCTAGGGCTATCCTAGGGCTATCCATCCTTAGTGGTAGAC
AAGGCTGTGTGAGAGGGCCTCTGTGGAGTGTTCCTGGCCTAGGA
CAGGGGCTCTGGCTCTCCTCCCTGACTTCA
```

FIG.10E

AGTAGTTTGCCGGAYCGAAGTGGAAGAACARCATTCCCGTGAGCAGAACC
AAGGATGACGCATAAGAGGAGCTAGTTCTGGCAGGTAGAGACCCCAGGG
GCTCAGTTCTGGCCCGTGTTAGGTTTAGAGGATGTGTGTTAGACTTCGG
AGTGGAGATGGTGGGAACTAGTCCTCTTCCTTTATTCCCGTCCCCCCAC
CTTCCAGTAGGTAAATAGACGCCTCAGGTGGCCAGTGTTGCGTTCTCT
TTCCCAGGAGACAAACGTCTTAGGCTTCAAGGVCCTCGGAAGATGAGCG
TGATTGTCCCAGGCATGAACATGGTTCATGAGAGAGTCTCTATCCGCCC
CGCAACGTGAGTGTCTACCCCCTTCCCCTCCCCATCATCCTAGT
CTCTGATGAGCTTCTAAGGCAGAACTCCAGCTGATGTGTATATGTGGA
GGGGTACCATGTGAGAAGAGCTTCTAGGGAAATCCAAGGACCCC
CATCCCGGATAGATCCCTTCTGGGTCATGGTGCCAAAGGCCTG
GGCCTGGCTCAGTGAGGCTGCCCTGCAGAGCATGAGACACTGCTAGC
ACGCTGGCAGAATAAGAACACGGAGTGTATCATCGAGCTGCAAAACAAGA
CACCTGTCTGGAATGATGACACAGTCCTATGTACTCAACTTCCATGGG
CGCGTCACACAGGCCCTCCGTGAAGAACTTCCAGATCATCATGGCAATGA
CCGTGAGTGTTTCTGTCCCTACTCATTATGTCCGTAGGATACCCAAGGC
CCTTAGCGTAGGGTTCAGCACCCTGCCTACCACTGCTAGAGTT
TAAGAATGTGAGCTATACAGTTAGATGTATGGAACTTTCTAACC

FIG. 10F

CTAATGACTGGAGGTCCTGGAAGAACCTTCTTTGTGAGCCCTGGTCCTAG
ATTCTGTATTCAAGGAGTCTCAGGCACGGAACACCCTTTAAAAGGA
CTTTCCTCTTTCTGTCCCTGGTGTTCACATGCATCTTACTTTGTCCT
TTGSCATCTGCCACCTCTTTCCTGCCACTTCTCCCAATGGCCTTTGTTT
TACTTCCCTTGTGATTCCCTGGCATCTCTATCTCTGCTTCACTGTTCTTCC
CTCATGTGGTTGGGTGTCTGTGTCCCCTGGCTTCCCTGCCACCATTCCTG
TCCTGTCCCTTTCTCTGTCTGTGCTCTGGCCCCAGGGACTACAT
CGTGATGCAGTTTGGCCGGGTAGCAGAGGATGTTCACCATGGATTACA
ACTACCCGCTGCACTGCAGCGTGCAGGCCCTTTGCCCGTCCCAGCTTC
GACAGCAAGCTGGAGTAGAGGCCTGAGCTTTCGTGCCCTTTGGGGTG
CCCAGCCTGGATGCCCTGCCTGCCCTGTGGAGACAGCCCTGCCT
ATCCTCTGTATATAGGCCCCAGCCCTTTCCCGCCAGATGAAGCTTTGGCCCTCAGTGGG
CTCCCTGGCCACCAGCCAGAGAGCGGGTGAAGCTTTGCCTCTGCTACTGAG
GCAGGGAGTAGTGCCAGGAGAGCGGGGTGAAGGATGAGAATAA
TTCTTTCCATGCCACCGAGATCC

FIG.10G

```
       V   I   K   N   S   N   Q   K   G   K   A   K   G   K   K   K   A   K        20
      GTG ATA AAG AAC AGC AAT CAA AAG GGC AAA GCC AAA GGA AAA AAG AAA GCG AAG        60

E   E   R   A   P   S   P   P   V   E   V   D   E   P   R   E   F   V   L   R   40
      GAG GAG AGG GCC CCG TCT CCC CCC GTG GAG GTG GAC GAA CCC CGG GAG TTT GTG CTC CGG  120

P   A   P   Q   G   R   T   V   R   C   R   L   T   R   D   K   K   G   M   D   60
      CCT GCC CCC CAG GGC CGC ACG GTG CGC TGC CGG CTG ACC CGG GAC AAA AAG GGC ATG GAT  180

R   G   M   Y   P   S   Y   F   L   H   L   D   T   E   K   K   V   F   L   L   80
      CGA GGC ATG TAT CCC TCC TAC TTC CTG CAC CTG GAC ACG GAG AAG AAG GTG TTC CTC TTG  240

A   G   R   K   R   K   K   S   K   T   A   N   Y   L   I   S   I   D   P   T   100
      GCT GGC AGG AAA CGA AAA AAG AGC AAG ACA GCC AAT TAC CTC ATC TCC ATC GAC CCT ACC  300

N   L   S   R   G   G   E   N   F   I   G   K   L   R   S   N   L   G   N       120
      AAT CTG TCC CGA GGA GGG GAG AAT TTC ATC GGG AAG CTG AGG TCC AAC CTC GGG AAC       360

R   F   T   V   F   D   N   G   Q   N   P   Q   R   G   Y   S   T   N   V   A   140
      CGC TTC ACG GTC TTT GAC AAC GGG CAG AAC CCA CAG CGT GGG TAC AGC ACT AAT GTG GCA  420
```

FIG.12A

|     |     |     |     |     |     |     |     |     |     |     |
| --- | --- | --- | --- | --- | --- | --- | --- | --- | --- | --- |
| S   | L   | R   | Q   | E   | L   | A   | A   | V   | I   | Y   | E   | T   | N   | V   | L   | G   | F   | R   | G   | 160 |
| AGC | CTT | CGG | CAG | GAG | CTG | GCA | GCT | GTG | ATC | TAT | GAA | ACC | AAC | GTG | CTG | GGC | TTC | CGT | GGC | 480 |
| P   | R   | R   | M   | T   | V   | I   | I   | P   | G   | M   | S   | A   | E   | N   | E   | R   | V   | P   | I   | 180 |
| CCC | CGC | CGC | ATG | ACC | GTC | ATC | ATT | CCT | GGC | ATG | AGT | GCG | GAG | AAC | GAG | AGG | GTC | CCC | ATC | 540 |
| R   | P   | R   | N   | A   | S   | D   | G   | L   | V   | R   | W   | Q   | N   | K   | T   | L   | E   | S   |     | 200 |
| CGG | CCC | CGA | AAT | GCT | AGT | GAT | GGC | CTG | GTG | CGC | TGG | CAG | AAC | AAG | ACG | CTG | GAG | AGC |     | 600 |
| L   | I   | E   | L   | H   | N   | K   | P   | P   | V   | W   | N   | D   | D   | S   | G   | S   | Y   | T   | L   | 220 |
| CTC | ATA | GAA | CTG | CAC | AAC | AAG | CCA | CCT | GTC | TGG | AAC | GAT | GAC | AGT | GGC | TCC | TAC | ACC | CTC | 660 |
| N   | F   | Q   | R   | G   | R   | V   | T   | Q   | A   | S   | V   | K   | N   | F   | Q   | I   | V   | H   | D   | 240 |
| AAC | TTC | CAA | CGG | GGC | CGG | GTC | ACC | CAG | GCC | TCA | GTC | AAG | AAC | TTC | CAG | ATT | GTC | CAC | GAT | 720 |
| D   | P   | D   | Y   | I   | Q   | L   | V   | F   | G   | R   | V   | A   | E   | D   | A   | F   | T   | L   | D   | 260 |
| GAC | CCC | GAC | TAT | ATC | CAG | CTG | GTG | TTC | GGC | CGC | GTG | GCG | GAG | GAC | GCC | TTC | ACC | CTA | GAC | 780 |
| Y   | R   | Y   | P   | L   | C   | A   | L   | Q   | A   | F   | A   | I   | A   | L   | S   | S   | F   | D   | G   | 280 |
| TAC | CGG | TAC | CCG | CTG | TGC | GCC | CTG | CAG | GCC | TTC | GCC | ATC | GCC | CTC | TCC | AGT | TTC | GAC | GGG | 840 |

FIG.12B

```
K   L   A   C   E   *
AAG CTG GCC TGC GAG TGA  CCCCAGCAGCCCTCAGGCCCCAGAGCCCGTCAGCGTGGG      285
                                                                      900

GGAAAGGATTCAGTGGAGGCTGGCAGGTCCCTCCAGCAAAGCTCCCGCGGAAAACTGCT           960

CCTGTGTCGGGGGCTGACCCTCTCACTGCCTCTCGGTGACCTCTCGTCCCCAGCCTGG            1020

CACAGGCCGAGGCAGGAGACCCGACGGGGTAGGACGGGAGATGAAGAACATCTGA               1080

GTTGGAGCCGCACATCTGGTCTCGGAGCTCGCCCTGCCCCGTGTGCCCCTCTCCCG              1140

CGCCCCAGTCACTTCCGTCCGGAGCAGTAGTCATTGTGTTTAACCTCCCTCTCCC               1200

CGGGACCGGCTAGGGCTCCGAGAGCTGGAGGGGCTAGAGGAGGGGTAGGTGATGG               1260

GGGACGAGGGCCAGGCACCCCACATCCCAATAAGCCGGTCCTTGCAAAAAAAAAA               1320

AAAAAAAAAAAAAAAAAA                                                    1338
```

FIG.12C

SEQUENCE LISTING ( 1 ) GENERAL INFORMATION:

( i i i ) NUMBER OF SEQUENCES: 59

( 2 ) INFORMATION FOR SEQ ID NO:1:

( i ) SEQUENCE CHARACTERISTICS:
        ( A ) LENGTH: 1804 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 139..1653

( x i ) SEQUENCE DESCRIPTION: SEQ ID NO:1:

```
CTGCAGGATT    CGGCACGAGC    AGCGGTCGGG    CCGGGGAGGA    TGCGGCCCGG    GGCGGCCCGA              60

GAGTTGAGCA    GGGTCCCCGC    GCCAGCCCCG    AGCGGTCCCG    GCCACCGGAG    CCGCAGCCGC             120

CGCCCCGCCC    CCGGGAGA    ATG   ACT   TCC   AAG   CCG   CAT   TCC   GAC   TGG   ATT   CCT   171
                          Met   Thr   Ser   Lys   Pro   His   Ser   Asp   Trp   Ile   Pro
                            1                     5                              10

TAC   AGT   GTC   CTA   GAT   GAT   GAG   GGC   AGC   AAC   CTG   AGG   CAG   CAG   AAG   CTC        219
Tyr   Ser   Val   Leu   Asp   Asp   Glu   Gly   Ser   Asn   Leu   Arg   Gln   Gln   Lys   Leu
                  15                        20                             25

GAC   CGG   CAG   CGG   GCC   CTG   TTG   GAA   CAG   AAG   CAG   AAG   AAG   CGC   CAA              267
Asp   Arg   Gln   Arg   Ala   Leu   Leu   Glu   Gln   Lys   Gln   Lys   Lys   Arg   Gln
            30                        35                        40

GAG   CCC   TTG   ATG   GTA   CAG   GCC   AAT   GCA   GAT   GGA   CGG   CCC   CGG   AGT   CGG        315
Glu   Pro   Leu   Met   Val   Gln   Ala   Asn   Ala   Asp   Gly   Arg   Pro   Arg   Ser   Arg
            45                        50                        55
```

| | | | | | | | | | | | | | | | | |
|---|---|---|---|---|---|---|---|---|---|---|---|---|---|---|---|---|
| CGA | GCC | CGG | CAG | TCA | GAG | GAG | CAA | GCC | CCC | CTG | GTG | GAG | TCC | TAC | CTC | 363 |
| Arg | Ala | Arg | Gln | Ser | Glu | Glu | Gln | Ala | Pro | Leu | Val | Glu | Ser | Tyr | Leu | |
| 60 | | | | 65 | | | | | 70 | | | | | | 75 | |
| AGC | AGC | AGT | GGC | AGC | ACC | AGC | TAC | CAA | GTT | CAA | GAG | GCC | GAC | TCG | ATT | 411 |
| Ser | Ser | Ser | Gly | Ser | Thr | Ser | Tyr | Gln | Val | Gln | Glu | Ala | Asp | Ser | Ile | |
| | | | | 80 | | | | | 85 | | | | | 90 | | |
| GCC | AGT | GTA | CAG | CTG | GGA | GCC | ACC | CGC | CCA | CCA | GCA | CCA | GCT | TCA | GCC | 459 |
| Ala | Ser | Val | Gln | Leu | Gly | Ala | Thr | Arg | Pro | Pro | Ala | Pro | Ala | Ser | Ala | |
| | | | 95 | | | | | 100 | | | | | 105 | | | |
| AAG | AAA | TCC | AAG | GGA | GCG | GCT | GCA | TCT | GGG | GGC | CAG | GGT | GGA | GCC | CCT | 507 |
| Lys | Lys | Ser | Lys | Gly | Ala | Ala | Ala | Ser | Gly | Gly | Gln | Gly | Gly | Ala | Pro | |
| | | 110 | | | | | 115 | | | | | 120 | | | | |
| AGG | AAG | GAG | AAG | AAG | GGA | AAG | CAT | AAA | GGC | ACC | AGC | GGG | CCA | GCA | ACT | 555 |
| Arg | Lys | Glu | Lys | Lys | Gly | Lys | His | Lys | Gly | Thr | Ser | Gly | Pro | Ala | Thr | |
| | 125 | | | | | 130 | | | | | 135 | | | | | |
| CTG | GCA | GAA | GAC | AAG | TCT | GAG | GCC | CAA | GGC | CCA | GTG | CAG | ATC | TTG | ACT | 603 |
| Leu | Ala | Glu | Asp | Lys | Ser | Glu | Ala | Gln | Gly | Pro | Val | Gln | Ile | Leu | Thr | |
| 140 | | | | | 145 | | | | | 150 | | | | | 155 | |
| GTG | GGA | CAG | TCA | GAC | CAC | GAC | AAG | GAT | GCG | GGA | GAG | ACA | GCA | GCC | GGC | 651 |
| Val | Gly | Gln | Ser | Asp | His | Asp | Lys | Asp | Ala | Gly | Glu | Thr | Ala | Ala | Gly | |
| | | | | 160 | | | | | 165 | | | | | 170 | | |
| GGG | GGC | GCA | CAG | CCC | AGT | GGG | CAG | GAC | CTC | CGT | GCC | ACG | ATG | CAG | AGG | 699 |
| Gly | Gly | Ala | Gln | Pro | Ser | Gly | Gln | Asp | Leu | Arg | Ala | Thr | Met | Gln | Arg | |
| | | | 175 | | | | | 180 | | | | | 185 | | | |
| AAG | GGC | ATC | TCC | AGC | AGC | ATG | AGC | TTT | GAC | GAG | GAC | GAG | GAT | GAG | GAT | 747 |
| Lys | Gly | Ile | Ser | Ser | Ser | Met | Ser | Phe | Asp | Glu | Asp | Glu | Asp | Glu | Asp | |
| | | 190 | | | | | 195 | | | | | 200 | | | | |
| GAA | AAC | AGC | TCC | AGC | TCC | TCC | CAG | CTA | AAC | AGC | AAC | ACC | CGC | CCT | AGT | 795 |
| Glu | Asn | Ser | Ser | Ser | Ser | Ser | Gln | Leu | Asn | Ser | Asn | Thr | Arg | Pro | Ser | |
| | 205 | | | | | 210 | | | | | 215 | | | | | |
| TCT | GCC | ACT | AGC | AGA | AAG | TCC | ATC | CGG | GAG | GCA | GCT | TCA | GCC | CCC | AGC | 843 |
| Ser | Ala | Thr | Ser | Arg | Lys | Ser | Ile | Arg | Glu | Ala | Ala | Ser | Ala | Pro | Ser | |
| 220 | | | | | 225 | | | | | 230 | | | | | 235 | |
| CCA | GCC | GCC | CCA | GAG | CCA | CCA | GTG | GAT | ATT | GAG | GTC | CAG | GAT | CTA | GAG | 891 |
| Pro | Ala | Ala | Pro | Glu | Pro | Pro | Val | Asp | Ile | Glu | Val | Gln | Asp | Leu | Glu | |
| | | | | 240 | | | | | 245 | | | | | 250 | | |
| GAG | TTT | GCA | CTG | AGG | CCA | GCC | CCA | CAA | GGG | ATC | ACC | ATC | AAA | TGC | CGC | 939 |
| Glu | Phe | Ala | Leu | Arg | Pro | Ala | Pro | Gln | Gly | Ile | Thr | Ile | Lys | Cys | Arg | |
| | | | 255 | | | | | 260 | | | | | 265 | | | |
| ATC | ACT | CGG | GAC | AAG | AAG | GGG | ATG | GAC | CGC | GGC | ATG | TAC | CCC | ACC | TAC | 987 |
| Ile | Thr | Arg | Asp | Lys | Lys | Gly | Met | Asp | Arg | Gly | Met | Tyr | Pro | Thr | Tyr | |
| | | 270 | | | | | 275 | | | | | 280 | | | | |
| TTT | CTG | CAC | CTA | GAC | CGT | GAG | GAT | GGC | AAG | AAG | GTG | TTC | CTC | CTG | GCG | 1035 |
| Phe | Leu | His | Leu | Asp | Arg | Glu | Asp | Gly | Lys | Lys | Val | Phe | Leu | Leu | Ala | |
| | 285 | | | | | 290 | | | | | 295 | | | | | |
| GGC | AGG | AAG | AGA | AAG | AAG | AGT | AAA | ACT | TCC | AAT | TAC | CTC | ATC | TCT | GTG | 1083 |
| Gly | Arg | Lys | Arg | Lys | Lys | Ser | Lys | Thr | Ser | Asn | Tyr | Leu | Ile | Ser | Val | |
| 300 | | | | | 305 | | | | | 310 | | | | | 315 | |
| GAC | CCA | ACA | GAC | TTG | TCT | CGG | GGA | GGC | GAT | AGC | TAT | ATC | GGG | AAA | TTG | 1131 |
| Asp | Pro | Thr | Asp | Leu | Ser | Arg | Gly | Gly | Asp | Ser | Tyr | Ile | Gly | Lys | Leu | |
| | | | | 320 | | | | | 325 | | | | | 330 | | |
| CGG | TCC | AAC | CTG | ATG | GGC | ACC | AAG | TTC | ACC | GTT | TAT | GAC | AAT | GGC | GTC | 1179 |
| Arg | Ser | Asn | Leu | Met | Gly | Thr | Lys | Phe | Thr | Val | Tyr | Asp | Asn | Gly | Val | |
| | | | 335 | | | | | 340 | | | | | 345 | | | |
| AAC | CCT | CAG | AAG | GCA | TCC | TCT | TCC | ACG | CTG | GAA | AGC | GGA | ACC | TTG | CGC | 1227 |
| Asn | Pro | Gln | Lys | Ala | Ser | Ser | Ser | Thr | Leu | Glu | Ser | Gly | Thr | Leu | Arg | |
| | | 350 | | | | | 355 | | | | | 360 | | | | |
| CAG | GAG | CTG | GCA | GCG | GTG | TGC | TAT | GAG | ACA | AAT | GTC | CTA | GGC | TTC | AAG | 1275 |
| Gln | Glu | Leu | Ala | Ala | Val | Cys | Tyr | Glu | Thr | Asn | Val | Leu | Gly | Phe | Lys | |
| | 365 | | | | | 370 | | | | | 375 | | | | | |

| | | | | | | | | | | | | | | | | |
|---|---|---|---|---|---|---|---|---|---|---|---|---|---|---|---|---|
| GGA | CCT | CGG | AAG | ATG | AGT | GTG | ATC | GTC | CCA | GGC | ATG | AAC | ATG | GTT | CAT | 1323 |
| Gly | Pro | Arg | Lys | Met | Ser | Val | Ile | Val | Pro | Gly | Met | Asn | Met | Val | His | |
| 380 | | | | 385 | | | | | 390 | | | | | 395 | | |
| GAG | AGA | GTC | TGT | ATC | CGC | CCC | CGC | AAT | GAA | CAT | GAG | ACC | CTG | TTA | GCA | 1371 |
| Glu | Arg | Val | Cys | Ile | Arg | Pro | Arg | Asn | Glu | His | Glu | Thr | Leu | Leu | Ala | |
| | | | | 400 | | | | | 405 | | | | | 410 | | |
| CGC | TGG | CAG | AAC | AAG | AAC | ACG | GAG | AGC | ATC | ATT | GAG | CTG | CAG | AAC | AAG | 1419 |
| Arg | Trp | Gln | Asn | Lys | Asn | Thr | Glu | Ser | Ile | Ile | Glu | Leu | Gln | Asn | Lys | |
| | | | 415 | | | | | 420 | | | | | 425 | | | |
| ACG | CCA | GTC | TGG | AAT | GAT | GAC | ACA | CAG | TCC | TAT | GTA | CTT | AAC | TTC | CAC | 1467 |
| Thr | Pro | Val | Trp | Asn | Asp | Asp | Thr | Gln | Ser | Tyr | Val | Leu | Asn | Phe | His | |
| | | 430 | | | | | 435 | | | | | 440 | | | | |
| GGC | CGT | GTC | ACA | CAG | GCT | TCT | GTG | AAG | AAC | TTC | CAG | ATC | ATC | CAC | GGC | 1515 |
| Gly | Arg | Val | Thr | Gln | Ala | Ser | Val | Lys | Asn | Phe | Gln | Ile | Ile | His | Gly | |
| 445 | | | | | 450 | | | | | 455 | | | | | | |
| AAT | GAC | CCG | GAC | TAC | ATC | GTC | ATG | CAG | TTT | GGC | CGG | GTA | GCA | GAA | GAT | 1563 |
| Asn | Asp | Pro | Asp | Tyr | Ile | Val | Met | Gln | Phe | Gly | Arg | Val | Ala | Glu | Asp | |
| 460 | | | | | 465 | | | | | 470 | | | | | 475 | |
| GTG | TTC | ACC | ATG | GAT | TAC | AAC | TAC | CCA | CTG | TGT | GCA | CTG | CAG | GCC | TTC | 1611 |
| Val | Phe | Thr | Met | Asp | Tyr | Asn | Tyr | Pro | Leu | Cys | Ala | Leu | Gln | Ala | Phe | |
| | | | | 480 | | | | | 485 | | | | | 490 | | |
| GCC | ATT | GCT | CTG | TCC | AGC | TTT | GAC | AGC | AAG | CTG | GCC | TGC | GAG | | | 1653 |
| Ala | Ile | Ala | Leu | Ser | Ser | Phe | Asp | Ser | Lys | Leu | Ala | Cys | Glu | | | |
| | | | | 495 | | | | 500 | | | | | 505 | | | |

TAGAGGCCCC CCACTGCCGT TAGGTGGCCC AGTCCGGAGT GGAGCTTGCC TGCCTGCCAA  1713

GACAGGCCTG CCTACCCTCT GTTCATAGGC CCTCTATGGG CTTTCTGGTC TGACCAACCA  1773

GAGATTGGTT TGCTCTGCCT CTGCTGCTTG A  1804

(2) INFORMATION FOR SEQ ID NO:2:

(i) SEQUENCE CHARACTERISTICS:
        (A) LENGTH: 505 amino acids
        (B) TYPE: amino acid
        (D) TOPOLOGY: unknown (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
| Met | Thr | Ser | Lys | Pro | His | Ser | Asp | Trp | Ile | Pro | Tyr | Ser | Val | Leu | Asp |
| 1 | | | | 5 | | | | 10 | | | | | 15 | | |
| Asp | Glu | Gly | Ser | Asn | Leu | Arg | Gln | Gln | Lys | Leu | Asp | Arg | Gln | Arg | Ala |
| | | | 20 | | | | 25 | | | | | 30 | | | |
| Leu | Leu | Glu | Gln | Lys | Gln | Lys | Lys | Arg | Gln | Glu | Pro | Leu | Met | Val | |
| | | 35 | | | | 40 | | | | | 45 | | | | |
| Gln | Ala | Asn | Ala | Asp | Gly | Arg | Pro | Arg | Ser | Arg | Ala | Arg | Gln | Ser | |
| | 50 | | | | 55 | | | | | 60 | | | | | |
| Glu | Glu | Gln | Ala | Pro | Leu | Val | Glu | Ser | Tyr | Leu | Ser | Ser | Gly | Ser | |
| 65 | | | | 70 | | | | 75 | | | | | 80 | | |
| Thr | Ser | Tyr | Gln | Val | Gln | Glu | Ala | Asp | Ser | Ile | Ala | Ser | Val | Gln | Leu |
| | | | | 85 | | | | 90 | | | | | 95 | | |
| Gly | Ala | Thr | Arg | Pro | Pro | Ala | Pro | Ala | Ser | Ala | Lys | Lys | Ser | Lys | Gly |
| | | | 100 | | | | 105 | | | | | 110 | | | |
| Ala | Ala | Ala | Ser | Gly | Gly | Gln | Gly | Gly | Ala | Pro | Arg | Lys | Glu | Lys | Lys |
| | | 115 | | | | 120 | | | | | 125 | | | | |
| Gly | Lys | His | Lys | Gly | Thr | Ser | Gly | Pro | Ala | Thr | Leu | Ala | Glu | Asp | Lys |
| | 130 | | | | 135 | | | | | 140 | | | | | |
| Ser | Glu | Ala | Gln | Gly | Pro | Val | Gln | Ile | Leu | Thr | Val | Gly | Gln | Ser | Asp |
| 145 | | | | 150 | | | | 155 | | | | | 160 | | |

| | | | | | | | | | | | | | | |
|---|---|---|---|---|---|---|---|---|---|---|---|---|---|---|
| His | Asp | Lys | Asp | Ala | Gly | Glu | Thr | Ala | Ala | Gly | Gly | Gly | Ala | Gln | Pro |
| | | | 165 | | | | 170 | | | | | 175 | | |
| Ser | Gly | Gln | Asp | Leu | Arg | Ala | Thr | Met | Gln | Arg | Lys | Gly | Ile | Ser | Ser |
| | | | 180 | | | | 185 | | | | | 190 | | |
| Ser | Met | Ser | Phe | Asp | Glu | Asp | Glu | Asp | Glu | Asp | Glu | Asn | Ser | Ser | Ser |
| | | 195 | | | | 200 | | | | | 205 | | | |
| Ser | Ser | Gln | Leu | Asn | Ser | Asn | Thr | Arg | Pro | Ser | Ala | Thr | Ser | Arg |
| 210 | | | | | 215 | | | | | 220 | | | | |
| Lys | Ser | Ile | Arg | Glu | Ala | Ala | Ser | Ala | Pro | Ser | Pro | Ala | Ala | Pro | Glu |
| 225 | | | | | 230 | | | | | 235 | | | | | 240 |
| Pro | Pro | Val | Asp | Ile | Glu | Val | Gln | Asp | Leu | Glu | Glu | Phe | Ala | Leu | Arg |
| | | | | 245 | | | | | 250 | | | | | 255 | |
| Pro | Ala | Pro | Gln | Gly | Ile | Thr | Ile | Lys | Cys | Arg | Ile | Thr | Arg | Asp | Lys |
| | | | 260 | | | | | 265 | | | | | 270 | | |
| Lys | Gly | Met | Asp | Arg | Gly | Met | Tyr | Pro | Thr | Tyr | Phe | Leu | His | Leu | Asp |
| | | 275 | | | | | 280 | | | | | 285 | | | |
| Arg | Glu | Asp | Gly | Lys | Lys | Val | Phe | Leu | Leu | Ala | Gly | Arg | Lys | Arg | Lys |
| | 290 | | | | | 295 | | | | | 300 | | | | |
| Lys | Ser | Lys | Thr | Ser | Asn | Tyr | Leu | Ile | Ser | Val | Asp | Pro | Thr | Asp | Leu |
| 305 | | | | | 310 | | | | | 315 | | | | | 320 |
| Ser | Arg | Gly | Gly | Asp | Ser | Tyr | Ile | Gly | Lys | Leu | Arg | Ser | Asn | Leu | Met |
| | | | | 325 | | | | | 330 | | | | | 335 | |
| Gly | Thr | Lys | Phe | Thr | Val | Tyr | Asp | Asn | Gly | Val | Asn | Pro | Gln | Lys | Ala |
| | | | 340 | | | | | 345 | | | | | 350 | | |
| Ser | Ser | Ser | Thr | Leu | Glu | Ser | Gly | Thr | Leu | Arg | Gln | Glu | Leu | Ala | Ala |
| | | 355 | | | | | 360 | | | | | 365 | | | |
| Val | Cys | Tyr | Glu | Thr | Asn | Val | Leu | Gly | Phe | Lys | Gly | Pro | Arg | Lys | Met |
| | 370 | | | | | 375 | | | | | 380 | | | | |
| Ser | Val | Ile | Val | Pro | Gly | Met | Asn | Met | Val | His | Glu | Arg | Val | Cys | Ile |
| 385 | | | | | 390 | | | | | 395 | | | | | 400 |
| Arg | Pro | Arg | Asn | Glu | His | Glu | Thr | Leu | Leu | Ala | Arg | Trp | Gln | Asn | Lys |
| | | | | 405 | | | | | 410 | | | | | 415 | |
| Asn | Thr | Glu | Ser | Ile | Ile | Glu | Leu | Gln | Asn | Lys | Thr | Pro | Val | Trp | Asn |
| | | | 420 | | | | | 425 | | | | | 430 | | |
| Asp | Asp | Thr | Gln | Ser | Tyr | Val | Leu | Asn | Phe | His | Gly | Arg | Val | Thr | Gln |
| | | 435 | | | | | 440 | | | | | 445 | | | |
| Ala | Ser | Val | Lys | Asn | Phe | Gln | Ile | Ile | His | Gly | Asn | Asp | Pro | Asp | Tyr |
| | 450 | | | | | 455 | | | | | 460 | | | | |
| Ile | Val | Met | Gln | Phe | Gly | Arg | Val | Ala | Glu | Asp | Val | Phe | Thr | Met | Asp |
| 465 | | | | | 470 | | | | | 475 | | | | | 480 |
| Tyr | Asn | Tyr | Pro | Leu | Cys | Ala | Leu | Gln | Ala | Phe | Ala | Ile | Ala | Leu | Ser |
| | | | | 485 | | | | | 490 | | | | | 495 | |
| Ser | Phe | Asp | Ser | Lys | Leu | Ala | Cys | Glu | | | | | | | |
| | | | 500 | | | | | 505 | | | | | | | |

( 2 ) INFORMATION FOR SEQ ID NO:3:

( i ) SEQUENCE CHARACTERISTICS:
        ( A ) LENGTH: 437 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:3:

| | | | | | | |
|---|---|---|---|---|---|---|
| ACGGCAATGA | CCTTGAGTGT | TGCCACTCCC | TGTTTTTGAT | GTTGTACGCA | TGGTGCCCAG | 60 |
| CCCCCACCCC | ACCCCCAATC | CCCTGATCTG | GTCCATATCA | GCCAGTGATG | GGATGTGGGT | 120 |
| ATATGGCTTT | TGTTAGAACT | TTCTAACTGT | AGTGATCTAG | AGTCCTGCCC | CTAGTGCCCT | 180 |
| GCATGTCTGG | GGCTTGGGAA | TACCCTTTAA | ATGGATGTCT | TTTCTCTCCT | GGGCCCTGCT | 240 |
| GTCTGTGTGC | ATCTCCCCCC | TTCACCCTCT | TGCTTCATAA | TGTTTCTCTT | GAACCTTTGT | 300 |
| TTTCTTCATC | CTTTCGATCT | CTTTGGCATT | TCTGCTTTCT | CCTTCCCTCT | TGTGGCCCAT | 360 |
| GTCTTACCTG | GTCTCCCTGT | CTCCACCATT | CTTGCTTGTG | CATTCCACAG | CGGACTACAT | 420 |
| CGTCATGCAT | TTTGGCC | | | | | 437 |

( 2 ) INFORMATION FOR SEQ ID NO:4:

( i ) SEQUENCE CHARACTERISTICS:
        ( A ) LENGTH: 437 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:4:

| | | | | | | |
|---|---|---|---|---|---|---|
| ACGGCAATGA | CCGTGAGTGT | TGCCACTCCC | TGTTTTTGAT | GTTGTACGCA | TGGTGCCCAG | 60 |
| CCCCCACCCC | ACCCCCAATC | CCCTGATCTG | GTCCATATCA | GCCAGTGATG | GGATGTGGGT | 120 |
| ATATGGCTTT | TGTAAGAACT | TTCTAACTGT | AGTGATCTAG | AGTCCTGCCC | CTAGTGCCCT | 180 |
| GCATGTCTGG | GGCTTGGGAA | TACCCTTTAA | ATGGATGTCT | TTTCTCTCCT | GGGCCCTGCT | 240 |
| GTCTGTGTGC | ATCTCCCCCC | TTCACCCTCT | TGCTTCATAA | TGTTTCTCTT | GAACCTTTGT | 300 |
| TTTGTTCATC | CTTTCGATCT | CTTTGGCATT | TCTGCTTTCT | CCTTCCCTCT | TGTGGCCCAT | 360 |
| GTCTTACCTG | GTCTCCCTGT | CTCCACCATT | CTTGCTTGTG | CATTCCACAG | CGGACTACAT | 420 |
| CGTCATGCAG | TTTGGCC | | | | | 437 |

( 2 ) INFORMATION FOR SEQ ID NO:5:

( i ) SEQUENCE CHARACTERISTICS:
        ( A ) LENGTH: 437 base pairs
        ( B ) TYPE: nucleic acid
        ( C ) STRANDEDNESS: single
        ( D ) TOPOLOGY: unknown ( i i ) MOLECULE TYPE: cDNA ( x i ) SEQUENCE DESCRIPTION: SEQ ID NO:5:

| | | | | | | |
|---|---|---|---|---|---|---|
| ACGGCAATGA | CCTTGAGTGT | TGCCACTCCC | TGTTTTTGAT | GTTGTACGCA | TGGTGCCCAG | 60 |
| CCCCCACCCC | ACCCCCAATC | CCCTGATCTG | CTCCATATCA | GCCAGTGATG | GGATGTGGGT | 120 |
| ATATGGCTTT | TGTTAGAACT | TTCTAACTGT | AGTGATCTAG | AGTCCTGCCC | CTAGTGCCCT | 180 |
| GCATGTCTGG | GGCTTGGGAA | TACCCTTTAA | ATGGATGTCT | TTTCTCTCCT | GGGCCCTGCT | 240 |
| GTCTGTGTGC | ATCTCCCCCC | TTCACCCTCT | TGCTTCATAA | TGTTTCTCTT | GAACCTTTGT | 300 |
| TTTGTTCATC | CTTTCGATCT | CTTTGGCATT | TCTGCTTTCT | CCTTCCCTCT | TGTGGCCCAT | 360 |
| GTCTTACCTG | GTCTCCCTGT | CTCCACCATT | CTTGCTTGTG | CATTCCACAG | CGGACTACAT | 420 |
| CGTCATGCAG | TTTGGCC | | | | | 437 |

( 2 ) INFORMATION FOR SEQ ID NO:6:

( i ) SEQUENCE CHARACTERISTICS:
        ( A ) LENGTH: 39 base pairs
        ( B ) TYPE: nucleic acid ( C ) STRANDEDNESS: single
( D ) TOPOLOGY: unknown ( i i ) MOLECULE TYPE: cDNA ( x i ) SEQUENCE DESCRIPTION: SEQ ID NO:6:

ACGGCAATGA CCCGGACTAC ATCGTCATGC AGTTTGGCC       39

( 2 ) INFORMATION FOR SEQ ID NO:7:

( i ) SEQUENCE CHARACTERISTICS:
( A ) LENGTH: 2040 base pairs
( B ) TYPE: nucleic acid
( C ) STRANDEDNESS: unknown
( D ) TOPOLOGY: unknown ( i i ) MOLECULE TYPE: DNA (genomic)

( i x ) FEATURE:
( A ) NAME/KEY: CDS
( B ) LOCATION: 153..1670

( x i ) SEQUENCE DESCRIPTION: SEQ ID NO:7:

```
TGGCGTGCAG CAGGGGCCTC GGCGGGGCCC AGCCCNCCGG TCCCGGGGAG GATACGTCCC        60

GGGGGCGGCC CGGGAGCTGA GCAGGCCCCC CGCGCCGGCC CCTCCGGGCC CCGGCCTCCA       120

GAGCCGCAGC CACCGCCCCG CCCCCGAGAG AC ATG ACT TCC AAG CCG CAT TCC        173
                                   Met Thr Ser Lys Pro His Ser
                                    1               5

GAC TGG ATT CCC TAC AGT GTC TTA GAT GAT GAG GGC AGA AAC CTG AGG        221
Asp Trp Ile Pro Tyr Ser Val Leu Asp Asp Glu Gly Arg Asn Leu Arg
         10              15                  20

CAG CAG AAG CTT GAT CGG CAG CGG GCC CTG CTG GAG CAG AAG CAG AAG        269
Gln Gln Lys Leu Asp Arg Gln Arg Ala Leu Leu Glu Gln Lys Gln Lys
     25              30                  35

AAG AAG CGC CAG GAG CCC CTG ATG GTG CAG GCC AAT GCA GAT GGG CGG        317
Lys Lys Arg Gln Glu Pro Leu Met Val Gln Ala Asn Ala Asp Gly Arg
 40              45                  50                      55

CCC CGG AGC CGG CGG GCC CGG CAG TCA GAG GAA CAA GCC CCC CTG GTG        365
Pro Arg Ser Arg Arg Ala Arg Gln Ser Glu Glu Gln Ala Pro Leu Val
                 60                  65                  70

GAG TCC TAC CTC AGC AGC AGT GGC AGC ACC AGC TAC CAA GTT CAA GAG        413
Glu Ser Tyr Leu Ser Ser Ser Gly Ser Thr Ser Tyr Gln Val Gln Glu
             75                  80                  85

GCC GAC TCA CTC GCC AGT GTG CAG CTG GGA GCC ACG CGC CCA ACA GCA        461
Ala Asp Ser Leu Ala Ser Val Gln Leu Gly Ala Thr Arg Pro Thr Ala
         90                  95                 100

CCA GCT TCA GCC AAG AGA ACC AAG GCG GCA GCT ACA GCA GGG GGC CAG        509
Pro Ala Ser Ala Lys Arg Thr Lys Ala Ala Ala Thr Ala Gly Gly Gln
105                 110                 115

GGT GGC GCC GCT AGG AAG GAG AAG AAG GGA AAG CAC AAA GGC ACC AGC        557
Gly Gly Ala Ala Arg Lys Glu Lys Lys Gly Lys His Lys Gly Thr Ser
120                 125                 130                 135

GGG CCA GCA GCA CTG GCA GAA GAC AAG TCT GAG GCC CAA GGC CCA GTG        605
Gly Pro Ala Ala Leu Ala Glu Asp Lys Ser Glu Ala Gln Gly Pro Val
                140                 145                 150

CAG ATT CTG ACT GTG GGC CAG TCA GAC CAC GCC CAG GAC GCA GGG GAG        653
Gln Ile Leu Thr Val Gly Gln Ser Asp His Ala Gln Asp Ala Gly Glu
            155                 160                 165

ACG GCA GCT GGT GGG GGC GAA CGG CCC AGC GGG CAG GAT CTC CGT GCC        701
Thr Ala Ala Gly Gly Gly Glu Arg Pro Ser Gly Gln Asp Leu Arg Ala
        170                 175                 180

ACG ATG CAG AGG AAG GGC ATC TCC AGC AGC ATG AGC TTT GAC GAG GAT        749
Thr Met Gln Arg Lys Gly Ile Ser Ser Ser Met Ser Phe Asp Glu Asp
```

|  |  |  |  |  |  |  |  |  |  |  |  |  |  |  |  |  |
|---|---|---|---|---|---|---|---|---|---|---|---|---|---|---|---|---|
| | | | | 185 | | | | | 190 | | | | | 195 | | |
| GAG | GAG | GAT | GAG | GAG | GAG | AAT | AGC | TCC | AGC | TCC | TCC | CAG | CTA | AAT | AGT | 797 |
| Glu | Glu | Asp | Glu | Glu | Glu | Asn | Ser | Ser | Ser | Ser | Ser | Gln | Leu | Asn | Ser | |
| 200 | | | | | 205 | | | | | 210 | | | | | 215 | |
| AAC | ACC | CGC | CCC | AGC | TCT | GCT | ACT | AGC | AGG | AAG | TCC | GTC | AGG | GAG | GCA | 845 |
| Asn | Thr | Arg | Pro | Ser | Ser | Ala | Thr | Ser | Arg | Lys | Ser | Val | Arg | Glu | Ala | |
| | | | | 220 | | | | | 225 | | | | | 230 | | |
| GCC | TCA | GCC | CCT | AGC | CCA | ACA | GCT | CCA | GAG | CAA | CCA | GTG | GAC | GTT | GAG | 893 |
| Ala | Ser | Ala | Pro | Ser | Pro | Thr | Ala | Pro | Glu | Gln | Pro | Val | Asp | Val | Glu | |
| | | | 235 | | | | | 240 | | | | | 245 | | | |
| GTC | CAG | GAT | CTT | GAG | GAG | TTT | GCA | CTG | AGG | CCG | GCC | CCC | CAG | GGT | ATC | 941 |
| Val | Gln | Asp | Leu | Glu | Glu | Phe | Ala | Leu | Arg | Pro | Ala | Pro | Gln | Gly | Ile | |
| | | 250 | | | | | 255 | | | | | 260 | | | | |
| ACC | ATC | AAA | TGC | CGC | ATC | ACT | CGG | GAC | AAG | AAA | GGG | ATG | GAC | CGG | GGC | 989 |
| Thr | Ile | Lys | Cys | Arg | Ile | Thr | Arg | Asp | Lys | Lys | Gly | Met | Asp | Arg | Gly | |
| | 265 | | | | | 270 | | | | | 275 | | | | | |
| ATG | TAC | CCC | ACC | TAC | TTT | CTG | CAC | CTG | GAC | CGT | GAG | GAT | GGG | AAG | AAG | 1037 |
| Met | Tyr | Pro | Thr | Tyr | Phe | Leu | His | Leu | Asp | Arg | Glu | Asp | Gly | Lys | Lys | |
| 280 | | | | | 285 | | | | | 290 | | | | | 295 | |
| GTG | TTC | CTC | CTG | GCG | GGA | AGG | AAG | AGA | AAG | AAG | AGT | AAA | ACT | TCC | AAT | 1085 |
| Val | Phe | Leu | Leu | Ala | Gly | Arg | Lys | Arg | Lys | Lys | Ser | Lys | Thr | Ser | Asn | |
| | | | | 300 | | | | | 305 | | | | | 310 | | |
| TAC | CTC | ATC | TCT | GTG | GAC | CCA | ACA | GAC | TTG | TCT | CGA | GGA | GGG | GAC | AGC | 1133 |
| Tyr | Leu | Ile | Ser | Val | Asp | Pro | Thr | Asp | Leu | Ser | Arg | Gly | Gly | Asp | Ser | |
| | | | 315 | | | | | 320 | | | | | 325 | | | |
| TAT | ATC | GGG | AAA | CTG | CGG | TCC | AAC | TTG | ATG | GGC | ACC | AAG | TTC | ACT | GTT | 1181 |
| Tyr | Ile | Gly | Lys | Leu | Arg | Ser | Asn | Leu | Met | Gly | Thr | Lys | Phe | Thr | Val | |
| | | 330 | | | | | 335 | | | | | 340 | | | | |
| TAT | GAC | AAT | GGA | GTC | AAC | CCT | CAG | AAG | GCC | TCA | TCC | TCC | ACT | TTG | GAA | 1229 |
| Tyr | Asp | Asn | Gly | Val | Asn | Pro | Gln | Lys | Ala | Ser | Ser | Ser | Thr | Leu | Glu | |
| | 345 | | | | | 350 | | | | | 355 | | | | | |
| AGT | GGA | ACC | TTA | CGT | CAG | GAG | CTG | GCA | GCT | GTG | TGC | TAC | GAG | ACA | AAC | 1277 |
| Ser | Gly | Thr | Leu | Arg | Gln | Glu | Leu | Ala | Ala | Val | Cys | Tyr | Glu | Thr | Asn | |
| 360 | | | | | 365 | | | | | 370 | | | | | 375 | |
| GTC | TTA | GGC | TTC | AAG | GGG | CCT | CGG | AAG | ATG | AGC | GTG | ATT | GTC | CCA | GGC | 1325 |
| Val | Leu | Gly | Phe | Lys | Gly | Pro | Arg | Lys | Met | Ser | Val | Ile | Val | Pro | Gly | |
| | | | | 380 | | | | | 385 | | | | | 390 | | |
| ATG | AAC | ATG | GTT | CAT | GAG | AGA | GTC | TCT | ATC | CGC | CCC | CGC | AAC | GAG | CAT | 1373 |
| Met | Asn | Met | Val | His | Glu | Arg | Val | Ser | Ile | Arg | Pro | Arg | Asn | Glu | His | |
| | | | 395 | | | | | 400 | | | | | 405 | | | |
| GAG | ACA | CTG | CTA | GCA | CGC | TGG | CAG | AAT | AAG | AAC | ACG | GAG | AGT | ATC | ATC | 1421 |
| Glu | Thr | Leu | Leu | Ala | Arg | Trp | Gln | Asn | Lys | Asn | Thr | Glu | Ser | Ile | Ile | |
| | | 410 | | | | | 415 | | | | | 420 | | | | |
| GAG | CTG | CAA | AAC | AAG | ACA | CCT | GTC | TGG | AAT | GAT | GAC | ACA | CAG | TCC | TAT | 1469 |
| Glu | Leu | Gln | Asn | Lys | Thr | Pro | Val | Trp | Asn | Asp | Asp | Thr | Gln | Ser | Tyr | |
| | 425 | | | | | 430 | | | | | 435 | | | | | |
| GTA | CTC | AAC | TTC | CAT | GGG | CGC | GTC | ACA | CAG | GCC | TCC | GTG | AAG | AAC | TTC | 1517 |
| Val | Leu | Asn | Phe | His | Gly | Arg | Val | Thr | Gln | Ala | Ser | Val | Lys | Asn | Phe | |
| 440 | | | | | 445 | | | | | 450 | | | | | 455 | |
| CAG | ATC | ATC | CAT | GGC | AAT | GAC | CCG | GAC | TAC | ATC | GTG | ATG | CAG | TTT | GGC | 1565 |
| Gln | Ile | Ile | His | Gly | Asn | Asp | Pro | Asp | Tyr | Ile | Val | Met | Gln | Phe | Gly | |
| | | | | 460 | | | | | 465 | | | | | 470 | | |
| CGG | GTA | GCA | GAG | GAT | GTG | TTC | ACC | ATG | GAT | TAC | AAC | TAC | CCG | CTG | TGT | 1613 |
| Arg | Val | Ala | Glu | Asp | Val | Phe | Thr | Met | Asp | Tyr | Asn | Tyr | Pro | Leu | Cys | |
| | | | 475 | | | | | 480 | | | | | 485 | | | |
| GCA | CTG | CAG | GCC | TTT | GCC | ATT | GCC | CTG | TCC | AGC | TTC | GAC | AGC | AAG | CTG | 1661 |
| Ala | Leu | Gln | Ala | Phe | Ala | Ile | Ala | Leu | Ser | Ser | Phe | Asp | Ser | Lys | Leu | |
| | | 490 | | | | | 495 | | | | | 500 | | | | |
| GCG | TGC | GAG | TAGAGGCCTC | TTCGTGCCCT | TTGGGGTTGC | CCAGCCTGGA | | | | | | | | | | 1710 |
| Ala | Cys | Glu | | | | | | | | | | | | | | |

```
                                        505
GCGGAGCTTG   CCTGCCTGCC   TGTGGAGACA   GCCCTGCCTA   TCCTCTGTAT   ATAGGCCTTC        1770

CGCCAGATGA   AGCTTTGGCC   CTCAGTGGGC   TCCCTGGCCC   AGCCAGCCAG   GAACTGGCTC        1830

CTTTGGCTCT   GCTACTGAGG   CAGGGGAGTA   GTGGAGAGCG   GGTGGGTGGG   TGTTGAAGGG        1890

ATTGAGAATT   AATTCTTTCC   ATGCCACGAG   GATCAACACA   CACTCCCACC   CTTGGGTAGT        1950

AAGTGGTTGT   TGTNAGTCGG   TACTTTACCA   AAGCTTGAGC   AACCTCTTCC   AAGCTTGGGA        2010

AAGGGCCGCA   AAAAGGCATT   AGGAGGGGAG                                               2040
```

( 2 ) INFORMATION FOR SEQ ID NO:8:

( i ) SEQUENCE CHARACTERISTICS:
        ( A ) LENGTH: 506 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:8:

```
Met  Thr  Ser  Lys  Pro  His  Ser  Asp  Trp  Ile  Pro  Tyr  Ser  Val  Leu  Asp
  1              5                      10                       15

Asp  Glu  Gly  Arg  Asn  Leu  Arg  Gln  Gln  Lys  Leu  Asp  Arg  Gln  Arg  Ala
              20                       25                       30

Leu  Leu  Glu  Gln  Lys  Gln  Lys  Lys  Arg  Gln  Glu  Pro  Leu  Met  Val
          35                       40                       45

Gln  Ala  Asn  Ala  Asp  Gly  Arg  Pro  Arg  Ser  Arg  Ala  Arg  Gln  Ser
     50                       55                       60

Glu  Glu  Gln  Ala  Pro  Leu  Val  Glu  Ser  Tyr  Leu  Ser  Ser  Gly  Ser
 65                       70                       75                   80

Thr  Ser  Tyr  Gln  Val  Gln  Glu  Ala  Asp  Ser  Leu  Ala  Ser  Val  Gln  Leu
                    85                       90                       95

Gly  Ala  Thr  Arg  Pro  Thr  Ala  Pro  Ala  Ser  Ala  Lys  Arg  Thr  Lys  Ala
               100                      105                      110

Ala  Ala  Thr  Ala  Gly  Gly  Gln  Gly  Gly  Ala  Ala  Arg  Lys  Glu  Lys  Lys
               115                      120                      125

Gly  Lys  His  Lys  Gly  Thr  Ser  Gly  Pro  Ala  Ala  Leu  Ala  Glu  Asp  Lys
     130                      135                      140

Ser  Glu  Ala  Gln  Gly  Pro  Val  Gln  Ile  Leu  Thr  Val  Gly  Gln  Ser  Asp
145                      150                      155                      160

His  Ala  Gln  Asp  Ala  Gly  Glu  Thr  Ala  Ala  Gly  Gly  Gly  Glu  Arg  Pro
               165                      170                      175

Ser  Gly  Gln  Asp  Leu  Arg  Ala  Thr  Met  Gln  Arg  Lys  Gly  Ile  Ser  Ser
               180                      185                      190

Ser  Met  Ser  Phe  Asp  Glu  Asp  Glu  Glu  Asp  Glu  Glu  Glu  Asn  Ser  Ser
               195                      200                      205

Ser  Ser  Ser  Gln  Leu  Asn  Ser  Asn  Thr  Arg  Pro  Ser  Ser  Ala  Thr  Ser
210                      215                      220

Arg  Lys  Ser  Val  Arg  Glu  Ala  Ala  Ser  Ala  Pro  Ser  Pro  Thr  Ala  Pro
225                      230                      235                      240

Glu  Gln  Pro  Val  Asp  Val  Glu  Val  Gln  Asp  Leu  Glu  Glu  Phe  Ala  Leu
                    245                      250                      255

Arg  Pro  Ala  Pro  Gln  Gly  Ile  Thr  Ile  Lys  Cys  Arg  Ile  Thr  Arg  Asp
               260                      265                      270

Lys  Lys  Gly  Met  Asp  Arg  Gly  Met  Tyr  Pro  Thr  Tyr  Phe  Leu  His  Leu
               275                      280                      285
```

| | | | | | | | | | | | | | | |
|---|---|---|---|---|---|---|---|---|---|---|---|---|---|---|
| Asp | Arg | Glu | Asp | Gly | Lys | Lys | Val | Phe | Leu | Leu | Ala | Gly | Arg | Lys | Arg |
| | 290 | | | | 295 | | | | | 300 | | | | |
| Lys | Lys | Ser | Lys | Thr | Ser | Asn | Tyr | Leu | Ile | Ser | Val | Asp | Pro | Thr | Asp |
| 305 | | | | 310 | | | | 315 | | | | | | 320 |
| Leu | Ser | Arg | Gly | Gly | Asp | Ser | Tyr | Ile | Gly | Lys | Leu | Arg | Ser | Asn | Leu |
| | | | | 325 | | | | | 330 | | | | | 335 | |
| Met | Gly | Thr | Lys | Phe | Thr | Val | Tyr | Asp | Asn | Gly | Val | Asn | Pro | Gln | Lys |
| | | | 340 | | | | | 345 | | | | | 350 | | |
| Ala | Ser | Ser | Ser | Thr | Leu | Glu | Ser | Gly | Thr | Leu | Arg | Gln | Glu | Leu | Ala |
| | | 355 | | | | | 360 | | | | | 365 | | | |
| Ala | Val | Cys | Tyr | Glu | Thr | Asn | Val | Leu | Gly | Phe | Lys | Gly | Pro | Arg | Lys |
| | 370 | | | | | 375 | | | | | 380 | | | | |
| Met | Ser | Val | Ile | Val | Pro | Gly | Met | Asn | Met | Val | His | Glu | Arg | Val | Ser |
| 385 | | | | | 390 | | | | | 395 | | | | | 400 |
| Ile | Arg | Pro | Arg | Asn | Glu | His | Glu | Thr | Leu | Leu | Ala | Arg | Trp | Gln | Asn |
| | | | | 405 | | | | | 410 | | | | | 415 | |
| Lys | Asn | Thr | Glu | Ser | Ile | Ile | Glu | Leu | Gln | Asn | Lys | Thr | Pro | Val | Trp |
| | | | 420 | | | | | 425 | | | | | 430 | | |
| Asn | Asp | Asp | Thr | Gln | Ser | Tyr | Val | Leu | Asn | Phe | His | Gly | Arg | Val | Thr |
| | | 435 | | | | | 440 | | | | | 445 | | | |
| Gln | Ala | Ser | Val | Lys | Asn | Phe | Gln | Ile | Ile | His | Gly | Asn | Asp | Pro | Asp |
| | 450 | | | | | 455 | | | | | 460 | | | | |
| Tyr | Ile | Val | Met | Gln | Phe | Gly | Arg | Val | Ala | Glu | Asp | Val | Phe | Thr | Met |
| 465 | | | | | 470 | | | | | 475 | | | | | 480 |
| Asp | Tyr | Asn | Tyr | Pro | Leu | Cys | Ala | Leu | Gln | Ala | Phe | Ala | Ile | Ala | Leu |
| | | | | 485 | | | | | 490 | | | | | 495 | |
| Ser | Ser | Phe | Asp | Ser | Lys | Leu | Ala | Cys | Glu | | | | | | |
| | | | 500 | | | | | 505 | | | | | | | |

( 2 ) INFORMATION FOR SEQ ID NO:9:

( i ) SEQUENCE CHARACTERISTICS:
        ( A ) LENGTH: 605 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:9:

| | | | | | |
|---|---|---|---|---|---|
| AGCCTACAGT | TTAAACAGTC | GACTCTAGAC | TTAATTAAGG | NTCCGGNGCG | CCCCCGGGTA | 60 |
| CCGAGCTCTG | GTCTCACCCA | CTGCCTGTTT | CTCTCTCTCC | ATCTGGGGAT | GTTTCCTGAG | 120 |
| CAGTTCAAGA | GGCCGACTCA | CTCGCCAGTG | TGCAGCTGGG | AGCCACGCGC | CCAACAGCAC | 180 |
| CAGCTTCAGC | CAAGAGAACC | AAGGCGGCAG | CTACAGCAGG | GGGCCAGGGC | GGCGCCGCTA | 240 |
| GGAAGGAGAA | GAAGGGAAAG | CACAAAGGTC | AGCTCACATT | CTCTACAGCC | CTGCCCAGCA | 300 |
| GGCCTGGCCT | CCACTGTAGG | GCTGGGGAAG | GTTTGTCCTC | CTGACTTGGA | GGGGAGGGAT | 360 |
| AGGATGAACA | GCCTCAGGGA | AGACACAGAC | TGCCACTCTG | GCACCCCCT | CAGGTGGCTC | 420 |
| ACAGGCCTCA | TCTAGCTTGG | GAGGTGCCTG | GGCTGCCTCT | GGGTGTGGGC | ATGCCTACCA | 480 |
| ACACTGCCAG | GAAGTGAAGT | CCTGCTCAGC | TTTGGCCCAG | AACCACCGTC | CCNANCTTNA | 540 |
| GTTACTTTGG | CCTTGAGGAA | CCTTTATNAT | GACCCCNTNA | AGGAGGATTT | TAACCAAGCT | 600 |
| GGATT | | | | | | 605 |

( 2 ) INFORMATION FOR SEQ ID NO:10:

( i ) SEQUENCE CHARACTERISTICS:
   ( A ) LENGTH: 826 base pairs
   ( B ) TYPE: nucleic acid
   ( C ) STRANDEDNESS: unknown
   ( D ) TOPOLOGY: unknown ( i i ) MOLECULE TYPE: DNA (genomic)

( x i ) SEQUENCE DESCRIPTION: SEQ ID NO:10:

| | | | | | | |
|---|---|---|---|---|---|---|
| TTCAAGGGCC | AAAGTTTTTT | AATGATGTAT | GGGAGTTAAT | GAAGGNGGTA | TGTGGGTNTG | 60 |
| TTNGNGGAAG | AAAACACCAG | CATTGATGGT | TGTAGNTGKT | GGTGTCCAKG | AATGATTGCT | 120 |
| GGCCTTGCCT | ATGGTNTGGA | TCAGTCCTTG | TTNTCCCATC | TTGTTTTTTC | CCATGTGCAG | 180 |
| TTGGTTTTTG | TAGATGGCTG | CCGTCTGCTT | TAAAGGACGT | GAGGTGTTGT | AAACCAACCC | 240 |
| TCGGCAATTA | ATTTGGGGGA | AGAGCAGAAG | AAATGAAGCC | CAACATCCCT | TACTAGCTTA | 300 |
| CCAGTTGTTA | ACAGGCTGGT | GCAATCATTA | GTTTTATAAA | AATCAGTTTT | GCAAATAAAG | 360 |
| TTTTGCAGAG | GGTTTCCCCA | CTCTTCCCTC | ATCCCCTTCA | TGGACGTCTG | AGAATCCAGG | 420 |
| CCCTCCTCTC | CTCCTCCTGG | ATGTAACTCA | GGCGTGTCCG | TGGCCTGCAG | GCACCAGCGG | 480 |
| GCCAGCAGCA | CTGGCAGAAG | ACAAGWCTGA | GGCCCAAGGC | CCAGTGCAGA | TTCTGACTGT | 540 |
| GGGCCAGTCA | GACCACGCCC | AGGACGCAGG | GGAGACGGCA | GCTGGTGGGG | GCGAACGGCC | 600 |
| CAGCGGGCAG | GATCTCCGTK | CCACGATGCA | GAGGAAGGGT | GAGCCCATG | GGGGCCCAGT | 660 |
| GATACCCCCA | AAACTCAGTC | CCAGGTTCTC | AGATGCACCT | TTCTCTGGGA | GCATGGNCTT | 720 |
| CCTGTGTCCA | AACCCCTCCC | TGGCAATGG | GGGTGAGGGT | GGGGCACACT | TCGGAGACAA | 780 |
| ATNAGAAACT | CTTAGGCAGG | GNCCCTGCTA | AGGCCCAGG | GAGGCC | | 826 |

( 2 ) INFORMATION FOR SEQ ID NO:11:

( i ) SEQUENCE CHARACTERISTICS:
   ( A ) LENGTH: 1943 base pairs
   ( B ) TYPE: nucleic acid
   ( C ) STRANDEDNESS: unknown
   ( D ) TOPOLOGY: unknown ( i i ) MOLECULE TYPE: DNA (genomic)

( x i ) SEQUENCE DESCRIPTION: SEQ ID NO:11:

| | | | | | | |
|---|---|---|---|---|---|---|
| TTAAACAGTC | GACTCTAGAC | TTAATTAAGG | ATCCGGCGCG | CCCCCGGGTA | CCGAGCTCAG | 60 |
| TGCAGGCCTT | GATACACAAG | AGACAGTGGT | AGGGTGSCTG | CTAGGTAGTG | GGGTAATGTA | 120 |
| GGGACTGAGC | TGAAACTGGG | TGGTGGGGAT | ATATCCTGAG | GATTGTGGCC | AGCCCGGCT | 180 |
| CATGTGTGTA | CCTGAGAGAA | TATCCTTTTA | TATCTGGACA | TGTGTGGGAA | TATATGTGTG | 240 |
| AATGGGAGTC | TATATGTGTA | GATATGGCTA | AGAGTGTGTG | CATAAGTTTG | TGGGGTACA | 300 |
| GGTGAGTCAG | TGTCTGAACA | TGAGTATGTG | ACCATGTGTA | TTTCAGGGGC | AGGGTAGACT | 360 |
| TCTCCTCATT | CATCCCTTCT | TCTTCTCTCC | TTGGCCCAGG | CATCTCCAGC | AGCATGAGCT | 420 |
| TTGACGAGGA | TGAGGAGGAT | GAGGAGGAGA | ATAGCTCCAG | CTCCTCCCAG | CTAAATAGTA | 480 |
| ACACCCGCCC | CAGCTCTGCT | ACTAGCAGGA | AGTCCGTCAG | GGTGAGTGAG | TGAGTCTGCA | 540 |
| TCCACAGCAG | TTTTTGGAGG | ACTGCTCATC | CGTTAGAGGT | GGACTGCATG | TGAAGAGATG | 600 |
| GACTCGTATG | CCTTTAGGAG | CTTCTCTGCT | GGCCTCTTAC | GTCCCTCTAC | CTTGCCTCCT | 660 |
| AACCTCTTCA | GCTAGGCCAG | CAGGGTGATG | TATGGGGGA | GATGCAGTTG | GACAGGATGA | 720 |
| CCTCTGAGGA | CCTCCCGTAT | CTCCCATCTC | CACCTCTAGG | AACTGTTGAG | GGCAGGGCTG | 780 |
| GGAAGATAGC | TTCTGACCCC | AGGCCCAGGC | TGGCCAGGCC | CCAATCCCAG | GATCCTTCCC | 840 |
| TCTCTCCCAC | CGCCACGTTA | GGAGGCAGAT | TTGGATCCCA | GACCACCAAT | TTGGGCTGCT | 900 |

-continued

| | | | | | | |
|---|---|---|---|---|---|---|
| TAGGGTCCTT | GGGGCTCAGG | CACCTATTCT | GCATCCCCAT | AGGAGGCAGC | CTCAGCCCCT | 960 |
| AGCCCAACAG | CTCCAGAGCA | ACCAGTGGAC | GTTGAGGTCC | AGGATCTTGA | GGAGTTTGCA | 1020 |
| CTGAGGCCGC | CCCCCCAGGG | TATCACCATC | AAATGCCGCA | TCACTCGGGA | CAAGAAAGGG | 1080 |
| ATGGACCGGG | GCATGTACCC | CACCTACTTT | CTGCACCTGG | ACCGTGAGGA | TGGGAAGAAG | 1140 |
| GTAAGGTTGG | TCTGGGCATG | TTATCATCTA | GGCTTTACAG | CCCTTTGAAA | TCCTAGGGGC | 1200 |
| TGAAATGTGA | CTGGAAGTCT | CATATCTACC | GCTGACCTCT | CAGTTCCTCA | AAGAAACTGC | 1260 |
| CTTCGTGTCT | GGTCTGTGCA | CATCTTTGTG | TTTTCCAGTG | CATTTGTGTG | TGTGCACATA | 1320 |
| TGTGCGTTTG | GGAGCTGACG | CAACGGAGAG | AGTCTGTGTG | AGTGGCTCTC | ATGACTGTGT | 1380 |
| GCAGACCAGA | GGCTGAGTCT | GGAATATGAC | CTCATTCCAC | TCCCCAAGGT | GTTCCTCCTG | 1440 |
| GCGGGAAGGA | AGAGAAAGAA | GAGTAAAACT | TCCAATTACC | TCATCTCTGT | GGACCCAACA | 1500 |
| GACTTGTCTC | GAGGAGGGGA | CAGCTATATC | GGGAAACTGC | GGGTACTAGC | ATTCCCCAG | 1560 |
| GAAGCAGGCG | GGAGTGGGAG | GGAGGGGCAG | GGGCAAGCTG | TCTGTAGAGG | GCCTGAATCT | 1620 |
| TCCTGAAGGA | GATCTAGGCC | AGGGATGGAT | ACTCTCCCAG | GATCCTCTCT | GATAATCACA | 1680 |
| TCCAACTGGA | GGCCTATGTC | TATGCCAGCC | TAGAGCCAGA | CTTGGAGATG | GGACTCACAC | 1740 |
| ACCCGACCCC | AAGCTGTTCC | CAGGAGGTGG | GTGCAGGCCC | ACCAAGAGTG | ATGGATCAA | 1800 |
| CCCCAGGGTG | TCACTGATAA | CGCAGGCCAC | CATGGAAGAG | TTGCCTTGGC | TCCATGGTCA | 1860 |
| ATGCCAAGGG | ACAGGGCTGA | GAGTGAGCTC | GGTACCCGGG | GGCGCKCCGG | ATCCTTAATT | 1920 |
| AAGTCTAGAG | TCGACTGTTT | AAG | | | | 1943 |

( 2 ) INFORMATION FOR SEQ ID NO:12:

( i ) SEQUENCE CHARACTERISTICS:
        ( A ) LENGTH: 881 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:12:

| | | | | | | |
|---|---|---|---|---|---|---|
| GATTTAGNGG | AACACAGCAN | CTTGNGGGTG | GGANGGCAGT | GGTGAAGGGG | CAGGAAGGCT | 60 |
| CTGAGCCTAG | GCCTCCAGGT | GGGGGCAGTG | GGGAGGTAGG | GTTTGCTGAG | GAACTGAGTA | 120 |
| CCAGATTTGG | GGAGCATAAA | TAAAGATGAG | AGGTCAGGAG | CTAAAGCTGG | AGATGGGGCT | 180 |
| GGACTGAGAC | TTAGGCTGGC | TGCGACAGAG | GAGATCTCAT | CCTCTCTCCA | CGGGTGCTAA | 240 |
| GCCTCTTCCA | CTGTCTTATC | AGATGCCATT | CTGTTTGCTC | ACCTCCCATG | AGGAGAACTC | 300 |
| CCATGTTCCC | CCAGATAAAT | CTYCTGAAGA | ATCCTGATTG | ACCTCCCTGA | ATTGCTCTCA | 360 |
| CTGAACTGAA | ATGCACTTTG | AGTCAACTCA | GAGCAAGTCC | AGGCCTTCTG | CCCACGAAGT | 420 |
| GTCTTCAAAG | ATGTGGATTC | AGTGAGCAGT | ATGCCTCCCT | GGGCCTGCTC | CTGTTCCAGC | 480 |
| CCAGAATGTT | TTGCAGGCTC | CTCATAGGAC | AGACGATGAG | CTGTTCCCTG | CTTCTGGGGC | 540 |
| AGAGGGTGCA | TGACTCTATA | CTGATTGTGC | CTTTATTTCA | GGTCCAACTT | GATGGGCACC | 600 |
| AAGTTCACTG | TTTATGACAA | TGGAGTCAAC | CCTCAGAAGG | CCTCATCCTC | CACTTTGGAA | 660 |
| AGTGGAACCT | TACGTCAGGA | GCTGGCAGCT | GTGTGCTACG | TGAGTCCTAG | GTTCGGGGT | 720 |
| CTCTGATTTC | CAAGGTAGAT | ATGAAATCCA | GGACTTGATG | CCTGATCTAG | GGCTATCCC | 780 |
| ATCCATCTTA | GTGGGTAGAC | AAGGCTGTGT | GGAGAGGGGC | TGTCCTCTGT | GGAGTGTTCC | 840 |
| TGGCCTAGGA | CAGGGGCTCT | GGCTCTCTCC | TCCTGACTTC | A | | 881 |

( 2 ) INFORMATION FOR SEQ ID NO:13:

( i ) SEQUENCE CHARACTERISTICS:
        ( A ) LENGTH: 1622 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:13:

```
AGTAGTTTGC  CGGAYCGAAG  TGGAAGAACA  RCATTCCCGT  GAGCAGAACC  AAGGATGACG    60
CATAAGAGGA  GCTAGTTCTG  GCAGGGTAGA  GACCCCAGGG  GCTCAGTTCT  GGCCCGTGTT   120
AGGTTTAGAG  GGATGTGTGT  TAGACTTCGG  AGTGGAGATG  GTGGGAACTA  GCTCTTCCTC   180
TTTATTCCCG  TCCCCCCCAC  CTTCTCCAGT  AGGTAAATAG  ACGCCTCAGG  TGGCCAGTGT   240
TGCGTTCTCT  TTCCCAGGAG  ACAAACGTCT  TAGGCTTCAA  GGGVCCTCGG  AAGATGAGCG   300
TGATTGTCCC  AGGCATGAAC  ATGGTTCATG  AGAGAGTCTC  TATCCGCCCC  CGCAACGTGA   360
GTGTCTACCC  CTTCCTCCCC  TCTTTCCCCA  TCATCCTAGT  CTCTGCATGA  GCTTCTAAGG   420
GCAGAACTCC  AGCTGATGTG  TATATGTGGA  GGGGTACCAT  GTGAGAAAGC  CCTGGAGGTC   480
TAGGGAAATC  CAAGGACCCC  CATTCCCGGG  ATAGATCCCT  TTCTGGGGTG  GTCATGGTGC   540
CAAAGGCCTG  GGCCTGGCTC  AGGTGAGGCT  GCCCTCCCAG  GAGCATGAGA  CACTGCTAGC   600
ACGCTGGCAG  AATAAGAACA  CGGAGTGTAT  CATCGAGCTG  CAAAACAAGA  CACCTGTCTG   660
GAATGATGAC  ACACAGTCCT  ATGTACTCAA  CTTCCATGGG  CGCGTCACAC  AGGCCTCCGT   720
GAAGAACTTC  CAGATCATCC  ATGGCAATGA  CCGTGAGTGT  TTCTGTCCCT  ACTCATTATG   780
GTCCGTAGGA  TACCCAAGGC  CCTTAGCGTA  GGGTTCAGCC  CACCTAGCCC  TGCCTACACT   840
GGCTAGAGTT  TAAGAATGTG  AGCTATACAG  CTAAGGTTAG  ATGTATGGAA  CTTTCTAACC   900
CTAATGACTG  GGAGGTCCTG  GAAGAACCTT  CTTTGSAGCC  CTGGTCCTAG  ATTCTGTGTA   960
TTCAACGGAG  TCTCAGGCAC  GGGAACACCC  TTTAAAGGA   CTTTTCCTCT  TTTCTGTCCC  1020
CTGGTGTTCA  CATGCATCTT  ACTTTGTCCT  TTGSCATCTG  CCACCTCTTT  CCTGCCACTT  1080
CTCCCAATTG  GCCTTTGTTT  TACTTCCCTT  TGTGATTCCC  CTGGCATCTC  TGCTTCTCAC  1140
TTGTTCTTCC  CTCATGTGGT  TTGGGTGTCT  GTCTATCCTT  CCCTGGCTCT  ACCATTCCTG  1200
TCCTGTCCTT  TTCTCTGTCT  GTGCCTGTGC  TTGGCCCCAG  CGGACTACAT  CGTGATGCAG  1260
TTTGGCCGGG  TAGCAGAGGA  TGTGTTCACC  ATGGATTACA  ACTACCCGCT  GTGTGCACTG  1320
CAGGCCTTTG  CCATTGCCCT  GTCCAGCTTC  GACAGCAAGC  TGGCGTGCGA  GTAGAGGCCT  1380
CTTCGTGCCC  TTTGGGGTTG  CCCAGCCTGG  AGCGGAGCTT  GCCTGCCTGC  CTGTGGAGAC  1440
AGCCCTGCCT  ATCCTCTGTA  TATAGGCCTT  CCGCCAGATG  AAGCTTTGGC  CCTCAGTGGG  1500
CTCCCTGGCC  CAGCCAGCCA  GGAACTGGCT  CCTTTGCCTC  TGCTACTGAG  GCAGGGGAGT  1560
AGTGGAGAGC  GGGTGGGTGG  GTGTGAAGGG  ATGAGAATAA  TTCTTTCCAT  GCCACGAGAT  1620
CC                                                                     1622
```

( 2 ) INFORMATION FOR SEQ ID NO:14:

( i ) SEQUENCE CHARACTERISTICS:
        ( A ) LENGTH: 1338 base pairs
        ( B ) TYPE: nucleic acid
        ( C ) STRANDEDNESS: unknown
        ( D ) TOPOLOGY: unknown ( i i ) MOLECULE TYPE: DNA (genomic)

-continued (ix) FEATURE:
  (A) NAME/KEY: CDS
  (B) LOCATION: 1..855

(xi) SEQUENCE DESCRIPTION: SEQ ID NO:14:

```
GTG ATA AAG AAC AGC AAT CAA AAG GGC AAA GCC AAA GGA AAA GGC AAA      48
Val Ile Lys Asn Ser Asn Gln Lys Gly Lys Ala Lys Gly Lys Gly Lys
 1           5                  10                  15

AAG AAA GCG AAG GAG GAG AGG GCC CCG TCT CCC CCC GTG GAG GTG GAC      96
Lys Lys Ala Lys Glu Glu Arg Ala Pro Ser Pro Pro Val Glu Val Asp
             20                  25                  30

GAA CCC CGG GAG TTT GTG CTC CGG CCT GCC CCC CAG GGC CGC ACG GTG     144
Glu Pro Arg Glu Phe Val Leu Arg Pro Ala Pro Gln Gly Arg Thr Val
         35                  40                  45

CGC TGC CGG CTG ACC CGG GAC AAA AAG GGC ATG GAT CGA GGC ATG TAT     192
Arg Cys Arg Leu Thr Arg Asp Lys Lys Gly Met Asp Arg Gly Met Tyr
     50                  55                  60

CCC TCC TAC TTC CTG CAC CTG GAC ACG GAG AAG AAG GTG TTC CTC TTG     240
Pro Ser Tyr Phe Leu His Leu Asp Thr Glu Lys Lys Val Phe Leu Leu
 65                  70                  75                  80

GCT GGC AGG AAA CGA AAA CGG AGC AAG ACA GCC AAT TAC CTC ATC TCC     288
Ala Gly Arg Lys Arg Lys Arg Ser Lys Thr Ala Asn Tyr Leu Ile Ser
                 85                  90                  95

ATC GAC CCT ACC AAT CTG TCC CGA GGA GGG GAG AAT TTC ATC GGG AAG     336
Ile Asp Pro Thr Asn Leu Ser Arg Gly Gly Glu Asn Phe Ile Gly Lys
            100                 105                 110

CTG AGG TCC AAC CTC CTG GGG AAC CGC TTC ACG GTC TTT GAC AAC GGG     384
Leu Arg Ser Asn Leu Leu Gly Asn Arg Phe Thr Val Phe Asp Asn Gly
        115                 120                 125

CAG AAC CCA CAG CGT GGG TAC AGC ACT AAT GTG GCA AGC CTT CGG CAG     432
Gln Asn Pro Gln Arg Gly Tyr Ser Thr Asn Val Ala Ser Leu Arg Gln
    130                 135                 140

GAG CTG GCA GCT GTG ATC TAT GAA ACC AAC GTG CTG GGC TTC CGT GGC     480
Glu Leu Ala Ala Val Ile Tyr Glu Thr Asn Val Leu Gly Phe Arg Gly
145                 150                 155                 160

CCC CGG CGC ATG ACC GTC ATC ATT CCT GGC ATG AGT GCG GAG AAC GAG     528
Pro Arg Arg Met Thr Val Ile Ile Pro Gly Met Ser Ala Glu Asn Glu
                165                 170                 175

AGG GTC CCC ATC CGG CCC CGA AAT GCT AGT GAC GGC CTG CTG GTG CGC     576
Arg Val Pro Ile Arg Pro Arg Asn Ala Ser Asp Gly Leu Leu Val Arg
            180                 185                 190

TGG CAG AAC AAG ACG CTG GAG AGC CTC ATA GAA CTG CAC AAC AAG CCA     624
Trp Gln Asn Lys Thr Leu Glu Ser Leu Ile Glu Leu His Asn Lys Pro
        195                 200                 205

CCT GTC TGG AAC GAT GAC AGT GGC TCC TAC ACC CTC AAC TTC CAA GGC     672
Pro Val Trp Asn Asp Asp Ser Gly Ser Tyr Thr Leu Asn Phe Gln Gly
    210                 215                 220

CGG GTC ACC CAG GCC TCA GTC AAG AAC TTC CAG ATT GTC CAC GCT GAT     720
Arg Val Thr Gln Ala Ser Val Lys Asn Phe Gln Ile Val His Ala Asp
225                 230                 235                 240

GAC CCC GAC TAT ATC GTG CTG CAG TTC GGC CGC GTG GCG GAG GAC GCC     768
Asp Pro Asp Tyr Ile Val Leu Gln Phe Gly Arg Val Ala Glu Asp Ala
                245                 250                 255

TTC ACC CTA GAC TAC CGG TAC CCG CTG TGC GCC CTG CAG GCC TTC GCC     816
Phe Thr Leu Asp Tyr Arg Tyr Pro Leu Cys Ala Leu Gln Ala Phe Ala
            260                 265                 270

ATC GCC CTC TCC AGT TTC GAC GGG AAG CTG GCC TGC GAG TGACCCAGC       865
Ile Ala Leu Ser Ser Phe Asp Gly Lys Leu Ala Cys Glu
        275                 280                 285

AGCCCCTCAG CGCCCCCAGA GCCCGTCAGC GTGGGGGAAA GGATTCAGTG GAGGCTGGCA     925
```

```
GGGTCCCTCC  AGCAAAGCTC  CCGCGGAAAA  CTGCTCCTGT  GTCGGGGCTG  ACCTCTCACT      985

GCCTCTCGGT  GACCTCCGTC  CTCTCCCCAG  CCTGGCACAG  GCCGAGGCAG  GAGGAGCCCG     1045

GACGGCGGGT  AGGACGGAGA  TGAAGAACAT  CTGGAGTTGG  AGCCGCACAT  CTGGTCTCGG     1105

AGCTCGCCTG  CGCCGCTGTG  CCCCCCTCCT  CCCCGCGCCC  CAGTCACTTC  CTGTCCGGGA     1165

GCAGTAGTCA  TTGTTGTTTT  AACCTCCCCT  CTCCCGGGA   CCGCGCTAGG  GCTCCGAGGA     1225

GCTGGGGCGG  GCTAGGAGGA  GGGGGTAGGT  GATGGGGAC   GAGGGCCAGG  CACCCACATC     1285

CCCAATAAAG  CCGCGTCCTT  GGCAAAAAAA  AAAAAAAAA   AAAAAAAAA   AAA            1338
```

( 2 ) INFORMATION FOR SEQ ID NO:15:

( i ) SEQUENCE CHARACTERISTICS:
        ( A ) LENGTH: 285 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:15:

```
Val  Ile  Lys  Asn  Ser  Asn  Gln  Lys  Gly  Lys  Ala  Lys  Gly  Lys  Gly  Lys
  1              5                    10                       15

Lys  Lys  Ala  Lys  Glu  Glu  Arg  Ala  Pro  Ser  Pro  Pro  Val  Glu  Val  Asp
               20                    25                       30

Glu  Pro  Arg  Glu  Phe  Val  Leu  Arg  Pro  Ala  Pro  Gln  Gly  Arg  Thr  Val
               35                    40                       45

Arg  Cys  Arg  Leu  Thr  Arg  Asp  Lys  Lys  Gly  Met  Asp  Arg  Gly  Met  Tyr
          50                    55                       60

Pro  Ser  Tyr  Phe  Leu  His  Leu  Asp  Thr  Glu  Lys  Lys  Val  Phe  Leu  Leu
 65                       70                       75                       80

Ala  Gly  Arg  Lys  Arg  Lys  Arg  Ser  Lys  Thr  Ala  Asn  Tyr  Leu  Ile  Ser
                    85                       90                       95

Ile  Asp  Pro  Thr  Asn  Leu  Ser  Arg  Gly  Gly  Glu  Asn  Phe  Ile  Gly  Lys
                    100                       105                      110

Leu  Arg  Ser  Asn  Leu  Leu  Gly  Asn  Arg  Phe  Thr  Val  Phe  Asp  Asn  Gly
               115                       120                       125

Gln  Asn  Pro  Gln  Arg  Gly  Tyr  Ser  Thr  Asn  Val  Ala  Ser  Leu  Arg  Gln
     130                       135                       140

Glu  Leu  Ala  Ala  Val  Ile  Tyr  Glu  Thr  Asn  Val  Leu  Gly  Phe  Arg  Gly
145                      150                       155                      160

Pro  Arg  Arg  Met  Thr  Val  Ile  Ile  Pro  Gly  Met  Ser  Ala  Glu  Asn  Glu
                    165                       170                       175

Arg  Val  Pro  Ile  Arg  Pro  Arg  Asn  Ala  Ser  Asp  Gly  Leu  Leu  Val  Arg
               180                       185                       190

Trp  Gln  Asn  Lys  Thr  Leu  Glu  Ser  Leu  Ile  Glu  Leu  His  Asn  Lys  Pro
          195                       200                       205

Pro  Val  Trp  Asn  Asp  Asp  Ser  Gly  Ser  Tyr  Thr  Leu  Asn  Phe  Gln  Gly
     210                       215                       220

Arg  Val  Thr  Gln  Ala  Ser  Val  Lys  Asn  Phe  Gln  Ile  Val  His  Ala  Asp
225                      230                       235                       240

Asp  Pro  Asp  Tyr  Ile  Val  Leu  Gln  Phe  Gly  Arg  Val  Ala  Glu  Asp  Ala
                    245                       250                       255

Phe  Thr  Leu  Asp  Tyr  Arg  Tyr  Pro  Leu  Cys  Ala  Leu  Gln  Ala  Phe  Ala
               260                       265                       270

Ile  Ala  Leu  Ser  Ser  Phe  Asp  Gly  Lys  Leu  Ala  Cys  Glu
          275                       280                       285
```

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

CCGACTCGAT TGCCAGTGTA        20

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

GCGGATACAG ACTCTCTCAT        20

( 2 ) INFORMATION FOR SEQ ID NO:18:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

GTTCAAGCTG GTTTCAAGAT G        21

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

ATCATCCAGG GAAGATGGAC        20

( 2 ) INFORMATION FOR SEQ ID NO:20:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

CTTCCTGGTG GAGGCAGTG        19

( 2 ) INFORMATION FOR SEQ ID NO:21:

( i ) SEQUENCE CHARACTERISTICS:
        ( A ) LENGTH: 20 base pairs (B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:21:

GAAGCAGTGA CGGGATGTGG 20

(2) INFORMATION FOR SEQ ID NO:22:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:22:

GGGTACCGAG CTCTGGTC 18

(2) INFORMATION FOR SEQ ID NO:23:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:23:

TCCAAGTCAG GAGGACAAAC 20

(2) INFORMATION FOR SEQ ID NO:24:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:24:

GAAAGTGCAT CTGAGAACCT G 21

(2) INFORMATION FOR SEQ ID NO:25:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:25:

CCTCCTCCTG GATGTAACTC 20

(2) INFORMATION FOR SEQ ID NO:26:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA ( x i ) SEQUENCE DESCRIPTION: SEQ ID NO:26:

TGTGACCATG TGTATTTCAG G 21

( 2 ) INFORMATION FOR SEQ ID NO:27:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:27:

CCTCTAACGG ATGAGCAGTC 20

( 2 ) INFORMATION FOR SEQ ID NO:28:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:28:

GATTTGGATC CCAGACCACC 20

( 2 ) INFORMATION FOR SEQ ID NO:29:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:29:

GACTTCCAGT CACATTTCAG C 21

( 2 ) INFORMATION FOR SEQ ID NO:30:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:30:

GTGCAGACCA GAGGCTGA 18

( 2 ) INFORMATION FOR SEQ ID NO:31:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:31:

TTCAGGCCCT CTACAGACAG 20

( 2 ) INFORMATION FOR SEQ ID NO:32:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:32:

TCATAGGACA GACGATGAGC  20

( 2 ) INFORMATION FOR SEQ ID NO:33:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:33:

GTCCTGGATT TCATATCTAC C  21

( 2 ) INFORMATION FOR SEQ ID NO:34:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:34:

AGGTAAATAG ACGCCTCAGG  20

( 2 ) INFORMATION FOR SEQ ID NO:35:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:35:

ACGTCTGCCC TTAGAAGCTC  20

( 2 ) INFORMATION FOR SEQ ID NO:36:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:36:

CTGGACCTGG CTCAGGTG  18

( 2 ) INFORMATION FOR SEQ ID NO:37:

( i ) SEQUENCE CHARACTERISTICS:
        ( A ) LENGTH: 22 base pairs (B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:37:

GTCATTAGGG TTAGAAAGTT CC 22

(2) INFORMATION FOR SEQ ID NO:38:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:38:

TCTTCCCTCA TGTGGTTTGG 20

(2) INFORMATION FOR SEQ ID NO:39:

(i) SEQUENCE CHARACTERISTICS:
(A) LENGTH: 19 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:39:

CCACAGGCAG GCAGGCAAG 19

(2) INFORMATION FOR SEQ ID NO:40:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:40:

TGCGCAGAAA CAATCACCTA 20

(2) INFORMATION FOR SEQ ID NO:41:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:41:

CAAGACGTGA ACCTGGA 17

(2) INFORMATION FOR SEQ ID NO:42:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: DNA ( x i ) SEQUENCE DESCRIPTION: SEQ ID NO:42:

GCGGATACAG ACTCTCTCAT 20

( 2 ) INFORMATION FOR SEQ ID NO:43:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:43:

GAGGACAAAT GTCCTAGGCT 20

( 2 ) INFORMATION FOR SEQ ID NO:44:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:44:

CATGCTCCTT GGGATGT 17

( 2 ) INFORMATION FOR SEQ ID NO:45:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:45:

TGAGGATTGC TTAAAGA 17

( 2 ) INFORMATION FOR SEQ ID NO:46:

( i ) SEQUENCE CHARACTERISTICS:
        ( A ) LENGTH: 90 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:46:

GAGACAAATG TCCTAGGCTT CAAGGGACCT CGGAAGATGA GTGTGATCGT CCCAGGCATG 60

AACATGGTTC ATGAGAGAGT CTGTATCCGC 90

( 2 ) INFORMATION FOR SEQ ID NO:47:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:47:

GGACAAGAAG GGGATGGAC 19

(2) INFORMATION FOR SEQ ID NO:48:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:48:

CCGTGGATGA TCTGGAAGT 19

(2) INFORMATION FOR SEQ ID NO:49:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:49:

TGAGACAAAT GTCCTAGGCT 20

(2) INFORMATION FOR SEQ ID NO:50:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:50:

TGGACAGAGC AATGGCGAAG 20

(2) INFORMATION FOR SEQ ID NO:51:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:51:

CCGACTCGAT TGCCAGTGTA 20

(2) INFORMATION FOR SEQ ID NO:52:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:52:

GCGGATACAG ACTCTCTCAT 20

(2) INFORMATION FOR SEQ ID NO:53:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:53:

CCGACTCGAT TGCCAGTGTA 20

( 2 ) INFORMATION FOR SEQ ID NO:54:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:54:

GGAGCTGTTT TCATCCTCAT C 21

( 2 ) INFORMATION FOR SEQ ID NO:55:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:55:

GAAGGAGAAG AAGGGAAAGC 20

( 2 ) INFORMATION FOR SEQ ID NO:56:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:56:

GGGTGTTACT ATTTAGCTGG 20

( 2 ) INFORMATION FOR SEQ ID NO:57:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:57:

TTCAAGAGGC CGACTCGATT 20

( 2 ) INFORMATION FOR SEQ ID NO:58:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear (ii) MOLECULE TYPE: DNA (xi) SEQUENCE DESCRIPTION: SEQ ID NO:58:

TTCCTCTGCA TCGTGGCAC                                                                                    1 9

(2) INFORMATION FOR SEQ ID NO:59:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:59:

CACCACCACC ACCACCACTG AATTC                                                                             2 5

MAMMALIAN TUB PROTEIN

This is a division of application Ser. No. 08/631,200, filed Apr. 12, 1996, now U.S. Pat. No. 5,646,040, which application claims the benefit of U.S. Provisional application No. 60/000,604, filed Jun. 30, 1995, U.S. Provisional application No. 60/001,273, filed Jul. 20, 1995, U.S. Provisional application No. 60/001,444, filed Jul. 26, 1995, U.S. Provisional application No. 60/002,759, filed Aug. 24, 1995, U.S. Provisional application No. 60/004,424, filed Sep. 28, 1995, and U.S. Provisional application No. 60/015,396, filed Apr. 9, 1996.

INTRODUCTION

The present invention relates to the mammalian tubby (tub) genes, including the human tub gene, which are novel genes involved in the control of mammalian body weight, including recombinant DNA molecules, cloned genes or degenerate variants thereof. The present invention further relates to novel mammalian, including human, tub gene products and to antibodies directed against such mammalian tub gene products, or conserved variants or fragments thereof. The present invention also includes cloning vectors containing mammalian tub gene molecules, and hosts which have been transformed with such molecules. In addition, the present invention presents methods for the diagnostic evaluation and prognosis of mammalian body weight disorders, including obesity, cachexia and anorexia, and for the identification of subjects exhibiting a predisposition to such conditions. Further, methods and compositions are presented for the treatment of mammalian body weight disorders, including obesity, cachexia and anorexia. Still further, the present invention relates to methods for the use of the mammalian tub gene and/or mammalian tub gene products for the identification of compounds which modulate the expression of the mammalian tub gene and/or the activity of the mammalian tub gene products. Such compounds can be used as therapeutic agents in the treatment of mammalian body weight disorders, including obesity, cachexia and anorexia.

BACKGROUND OF THE INVENTION

Obesity represents the most prevalent of body weight disorders, and it is the most important nutritional disorder in the western world, with estimates of its prevalence ranging from 30% to 50% within the middle-aged population. Other body weight disorders, such as anorexia nervosa and bulimia nervosa which together affect approximately 0.2% of the female population of the western world, also pose serious health threats. Further, such disorders as anorexia and cachexia (wasting) are also prominent features of other diseases such as cancer, cystic fibrosis, and AIDS.

Obesity, defined as an excess of body fat relative to lean body mass, also contributes to other diseases. For example, this disorder is responsible for increased incidences of diseases such as coronary artery disease, hypertension, stroke, diabetes, hyperlipidaemia and some cancers. (See, e.g., Nishina, P. M. et al., 1994, Metab. 43:554–558; Grundy, S. M. & Barnett, J. P., 1990, Dis. Mon. 36:641–731) Obesity is not merely a behavioral problem, i.e., the result of voluntary hyperphagia. Rather, the differential body composition observed between obese and normal subjects results from differences in both metabolism and neurologic/metabolic interactions. These differences seem to be, to some extent, due to differences in gene expression, and/or level of gene products or activity (Friedman, J. M. et al., 1991, Mammalian Gene 1:130–144).

The epidemiology of obesity strongly shows that the disorder exhibits inherited characteristics (Stunkard, 1990, N. Eng. J. Med. 322:1483). Moll et al. have reported that, in many populations, obesity seems to be controlled by a few genetic loci (Moll et al. 1991, Am. J. Hum. Gen. 49:1243). In addition, human twin studies strongly suggest a substantial genetic basis in the control of body weight, with estimates of heritability of 80–90% (Simbpoulos, A. P. & Childs B., eds., 1989, in "Genetic Variation and Nutrition in Obesity", World Review of Nutrition and Diabetes 63, S. Karger, Basel, Switzerland; Borjeson, M., 1976, Acta. Paediatr. Scand. 65:279–287).

Studies of non-obese persons who deliberately attempted to gain weight by systematically over-eating were found to be more resistant to such weight gain and able to maintain an elevated weight only by very high caloric intake. In contrast, spontaneously obese individuals are able to maintain their status with normal or only moderately elevated caloric intake. In addition, it is a commonplace experience in animal husbandry that different strains of swine, cattle, etc., have different predispositions to obesity. Studies of the genetics of human obesity and of models of animal obesity demonstrate that obesity results from complex defective regulation of both food intake, food induced energy expenditure and of the balance between lipid and lean body anabolism.

There are a number of genetic diseases in man and other species which feature obesity among their more prominent symptoms, along with, frequently, dysmorphic features and mental retardation. For example, Prader-Willi syndrome (PWS; reviewed in Knoll, J. H. et al., 1993, Am. J. Med. Genet. 46:2–6) affects approximately 1 in 20,000 live births, and involves poor neonatal muscle tone, facial and genital deformities, and generally obesity.

In addition to PWS, many other pleiotropic syndromes which include obesity as a symptom have been characterized. These syndromes are more genetically straightforward, and appear to involve autosomal recessive alleles. The diseases, which include, among others, Ahlstroem, Carpenter, Bardet-Biedl, Cohen, and Morgagni-Stewart-Monel Syndromes.

A number of models exist for the study of obesity (see, e.g., Bray, G. A., 1992, Prog. Brain Res. 93:333–341, and Bray, G. A., 1989, Amer. J. Clin. Nutr. 5:891–902). For example, animals having mutations which lead to syndromes that include obesity symptoms have also been identified. Attempts have been made to utilize such animals as models for the study of obesity, and the best studied animal models, to date, for genetic obesity are mice. For reviews, see e.g., Friedman, J. M. et al., 1991, Mamm. Gen. 1:130–144; Friedman, J. M. and Liebel, R. L., 1992, Cell 69:217–220.)

Studies utilizing mice have confirmed that obesity is a very complex trait with a high degree of heritability. Mutations at a number of loci have been identified which lead to obese phenotypes. These include the autosomal recessive mutations obese (ob), diabetes (db), fat (fat) and tubby (tub). In addition, the autosomal dominant mutations Yellow at the agouti locus and Adipose (Ad) have been shown to contribute to an obese phenotype.

The ob and db mutations are on chromosomes 6 and 4, respectively, but lead to clinically similar pictures of obesity, evident starting at about one month of age, which include hyperphagia, severe abnormalities in glucose and insulin metabolism, very poor thermoregulation and non-shivering thermogenesis, and extreme torpor and underdevelopment of the lean body mass.

The ob gene and its human homologue have recently been cloned (Zhang, Y. et al., 1994, Nature 372:425–432). The gene appears to produce a 4.5 kb adipose tissue messenger RNA which contains a 167 amino acid open reading frame. The predicted amino acid sequence of the ob gene product indicates that it is a secreted protein and may, therefore, play a role as part of a signalling pathway from adipose tissue which may serve to regulate some aspect of body fat deposition.

The db locus encodes a high affinity receptor for the ob gene product (Chen, H. et al., Cell 84:491–495). The db gene product is a single membrane-spanning receptor most closely related to the gp130 cytokine receptor signal transducing component (Tartaglia, L. A. et al., 1995, Cell 83:1263–1271).

Homozygous mutations at either the fat or tub loci cause obesity which develops more slowly than that observed in ob and db mice (Coleman, D. L., and Eicher, E. M., 1990, J. Heredity 81:424–427), with tub obesity developing slower than that observed in fat animals. This feature of the tub obese phenotype makes the development of tub obese phenotype closest in resemblance to the manner in which obesity develops in humans. Even so, however, the obese phenotype within such animals can be characterized as massive in that animals eventually attain body weights which are nearly two times the average weight seen in normal mice. tub/tub mice develop insulin resistance with their weight gain but do not progress to overt diabetes.

In addition to obesity, retinal defects, hearing loss and infertility have all been observed in tub mice (Heckenlively, 1988, in Retinitis Pigmentosa, Heckenlively, ed., Lippincott, Philadelphia, pp. 221–235; Coleman, D. L. & Eicher, E. M., 1990, J. Hered. 81:424–427; Ohlemiller, K. K. et al., 1995, Neuroreport 6:845–849). Several human syndromes exist in which such defects are found to co-exist with an obesity phenotype, including Bardet-Biedl syndrome, Ahlstroem syndrome, polycystic ovarian disease and Usher's syndrome.

The fat mutation has been mapped to mouse chromosome 8, while the tub mutation has been mapped to mouse chromosome 7. According to Naggert et al., the fat mutation has recently been identified (Naggert, J. K., et al., 1995, Nature Genetics 10:135–141). Specifically, the fat mutation appears to be a mutation within the Cpe locus, which encodes the carboxypeptidase (Cpe) E protein. Cpe is an exopeptidase involved in the processing of prohormones, including proinsulin.

The dominant Yellow mutation at the agouti locus, causes a pleiotropic syndrome which causes moderate adult onset obesity, a yellow coat color, and a high incidence of tumor formation (Herberg, L. and Coleman, D. L., 1977, Metabolism 26:59), and an abnormal anatomic distribution of body fat (Coleman, D. L., 1978, Diabetologia 14:141–148). This mutation may represent the only known example of a pleiotropic mutation that causes an increase, rather than a decrease, in body size. The mutation causes the widespread expression of a protein which is normally seen only in neonatal skin (Michaud, E. J. et al.) 1994, Genes Devel. 8:1463–1472).

Other animal models include fa/fa (fatty) rats, which bear many similarities to the ob/ob and db/db mice, discussed above. One difference is that, while fa/fa rats are very sensitive to cold, their capacity for non-shivering thermogenesis is normal. Torpor seems to play a larger part in the maintenance of obesity in fa/fa rats than in the mice mutants. In addition, inbred mouse strains such as NZO mice and Japanese KK mice are moderately obese. Certain hybrid mice, such as the Wellesley mouse, become spontaneously fat. Further, several desert rodents, such as the spiny mouse, do not become obese in their natural habitats, but do become so when fed on standard laboratory feed.

Animals which have been used as models for obesity have also been developed via physical or pharmacological methods. For example, bilateral lesions in the ventromedial hypothalamus (VMH) and ventrolateral hypothalamus (VLH) in the rat are associated, respectively, with hyperphagia and gross obesity and with aphagia, cachexia and anorexia. Further, it has been demonstrated that feeding monosodium-glutamate (MSG) or gold thioglucose to newborn mice also results in an obesity syndrome.

In summary, therefore, obesity, which poses a major, worldwide health problem, represents a complex, highly heritable trait. Given the severity, prevalence and potential heterogeneity of such disorders, there exists a great need for the identification of those genes that participate in the control of body weight.

It is an objective of the invention to provide modulators, such as intracellular modulators, of body weight, to provide methods for diagnosis of body weight disorders, to provide therapy for such disorders and to provide an assay system for the screening of substances which can be used to control body weight.

SUMMARY OF THE INVENTION

The present invention relates to the identification of novel nucleic acid molecules and proteins encoded by such nucleic acid molecules or degenerate variants thereof, that participate in the control of mammalian body weight. The nucleic acid molecules of the present invention represent the genes corresponding to the mammalian tub gene, including the human tub gene, which are involved in the regulation, control and/or modulation of body weight.

In particular, the compositions of the present invention include nucleic acid molecules (e.g., tub gene), including recombinant DNA molecules, cloned genes or degenerate variants thereof, especially naturally occurring variants, which encode novel tub gene products, and antibodies directed against such tub gene products or conserved variants or fragments thereof. The compositions of the present invention additionally include cloning vectors, including expression vectors, containing the nucleic acid molecules of the invention and hosts which have been transformed with such nucleic acid molecules.

Nucleic acid sequences of a wild type and a mutant form of the murine tub gene are provided. The wild type murine tub gene produces a full length transcript of approximately 7.0 kb and encodes a protein of 505 amino acids, the sequence of which is provided. The amino acid sequence of the predicted full length tub gene product does not contain either a recognizable transmembrane domain or a signal sequence, suggesting that the tub gene product is an intracellular gene product. The mammalian tub gene is, as shown herein, expressed in the brain, including the hypothalamus.

Nucleic acid sequences of a wild-type human tub gene are also provided. The human tub gene encodes a full length protein of 506 amino acids, the sequence of which is provided. The human tub gene and gene product are strikingly similar to the murine tub gene and gene product. Specifically, the human tub gene is, at the nucleotide level, 89% identical to the murine tub gene. Further, the amino acid sequence of the human tub gene product is 94% identical to the amino acid sequence of the murine tub gene product.

Both murine and human tub genes produce transcripts which undergo alternative splicing. Such alternative splicing yields, in addition to the full length transcripts, transcripts which lack sequences corresponding to tub exon 5. Nucleic acid sequences corresponding to such alternatively spliced transcripts and the tub gene products encoded by such alternatively spliced transcripts are provided herein.

In addition, this invention presents methods for the diagnostic evaluation and prognosis of body weight disorders, including obesity, cachexia and anorexia, and for the identification of subjects having a predisposition to such conditions. For example, nucleic acid molecules of the invention can be used as diagnostic hybridization probes or as primers for diagnostic PCR analysis for the identification of tub gene mutations, allelic variations and regulatory defects in the tub gene, and of alternatively spliced transcripts produced by the tub gene. For example, human tub genomic sequences are provided which can be used to selectively amplify human tub exons for analysis.

Further, methods and compositions are presented for the treatment of body weight disorders, including obesity, cachexia and anorexia. Such methods and compositions are capable of modulating the level of tub gene expression and/or the level of tub gene product activity. Such methods and compositions can also be utilized in the treatment or amelioration of symptoms of tub gene-related sensory defects (e.g., eye and hearing) and fertility defects.

Still further, the present invention relates to methods for the use of the tub gene and/or tub gene products for the identification of compounds which modulate tub gene expression and/or the activity of tub gene products. Such compounds can be used as agents to control body weight and, in particular, therapeutic agents in the treatment of body weight and body weight disorders, including obesity, cachexia and anorexia. Such methods and compositions can also be utilized in the treatment or amelioration of symptoms of tub gene-related sensory (e.g., eye and hearing) and fertility defects. It is further contemplated that the nucleic acid molecules, peptides and other compounds of the invention can have agricultural applications. For example, the ratio of fat to lean tissue of agricultural animals can be favorably altered, e.g., this ratio can be decreased.

This invention is based, in part, on the genetic and physical mapping of the tub gene to a specific portion of mouse chromosome 7, described in the Examples presented, below, in Section 6 and 7. The invention is further based, in part, on the expression and sequence analysis of a candidate tub gene using nucleic acid derived from wild type and tub homozygous animals, which proves that this candidate gene does, indeed, represent the tub gene. Such analyses are described in the Examples presented, below, in Sections 8–12, and include the identification of a splice site mutation in nucleic acid derived from tub animals which is absent from the corresponding nucleic acid derived from wild type, non-obese animals. This single base mutation consists of a guanine (G) to a thymidine (T) in the splice site recognition sequence, which results in the retention of an intronic sequence in the mature tub mRNA that encodes an abnormal, loss-of-function, tub gene product. Further, Section 13 presents the successful cloning of the human tub gene homologue.

Still further, the Example presented in Section 14 demonstrates that both the murine and human tub transcripts undergo alternative splicing. Section 15 demonstrates the successful expression of recombinant human and murine tub gene products. Finally, the Example presented in Section 16 describes the identification, cloning and characterization of a human tub homolog.

DESCRIPTION OF THE FIGURES

Figure 6B:
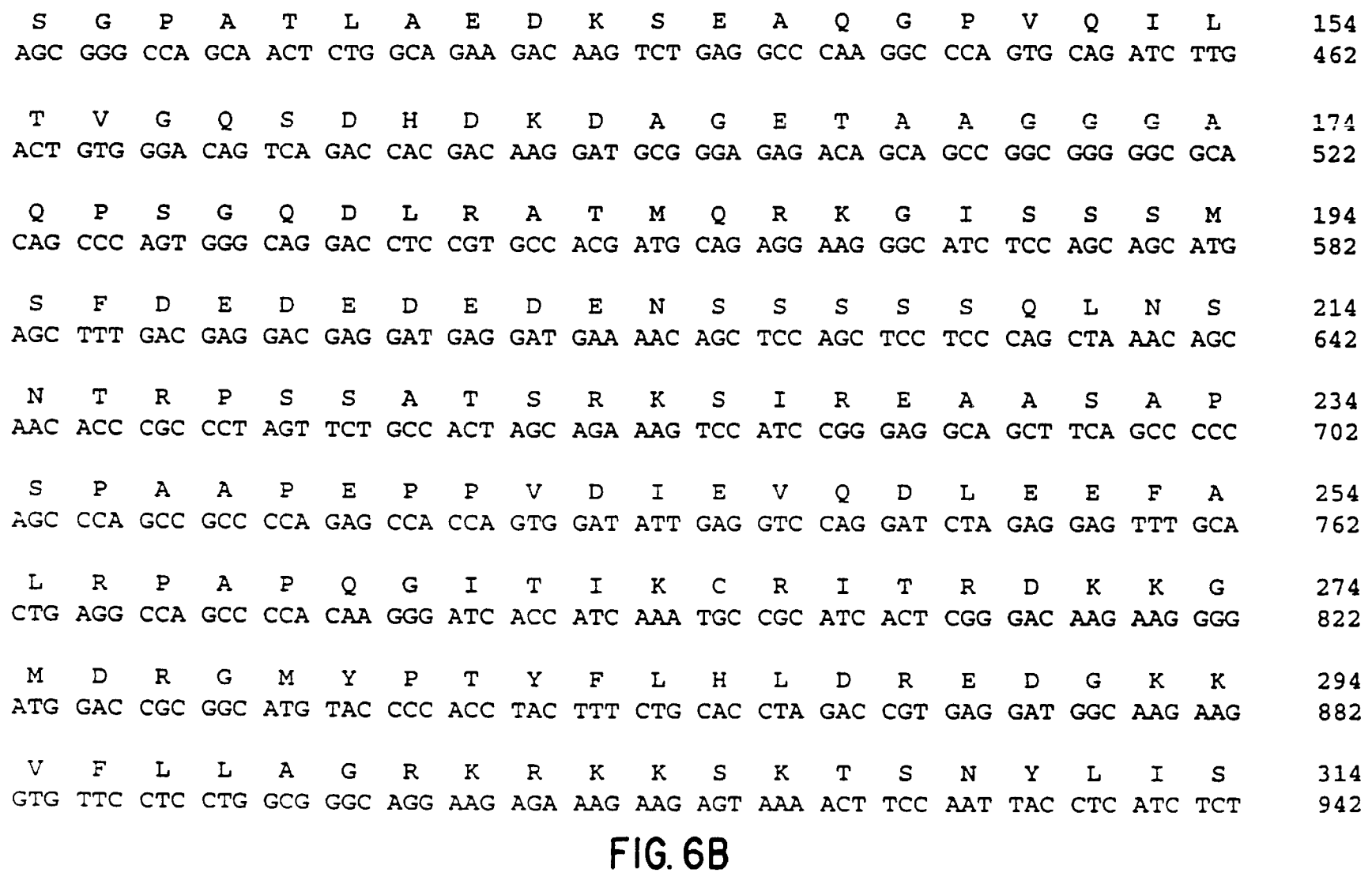

FIG. 6. Nucleotide sequence of the coding region (and portions of 5' and 3' untranslated regions) of the wild type tub gene (bottom line) (SEQ ID NO: 1) and the encoded amino acid sequence (top line) (SEQ ID NO: 2).

FIGS. 7A–7D. Alignment of cDNA and genomic sequences derived from wild type C57BL/6J (genomic= SEQ ID NO: 4; cDNA=SEQ ID NO: 6) and tub RNA (genomic=SEQ ID NO: 3; cDNA=SEQ ID NO: 5) in the region of the splice site mutation. See Section 12.1 and 12.2 for details.

FIGS. 9A–9D. Nucleotide sequence of the coding region (and portions of 5' and 3' untranslated regions) of the human tub gene (bottom line) (SEQ ID NO: 7) and the encoded human tub gene product amino acid sequence (top line) (SEQ ID NO: 8).

FIGS. 10A–10G. Human tub genomic sequence. Depicted herein are human tub gene exons 4–12 nucleotide sequences and flanking intronic sequences. Intron boundaries are depicted in bold; exon sequences are underlined. 10A (SEQ ID NO: 9). Exon 4 (corresponding to nucleotide sequence 254–397 of FIG. 9) and its flanking genomic sequence. 10B (SEQ ID NO: 10). Exon 5 (corresponding to nucleotide sequence 398–565 of FIG. 9) and its flanking genomic sequence. 10C–10D (SEQ ID NO: 11). Exons 6–8 (corresponding to nucleotide sequences 566–687, 688–885, and 886–998 of FIGS. 9A–9D, respectively) and its flanking genomic sequence. 10E (SEQ ID NO: 12). Exon 9 (corresponding to nucleotide sequence 999–1116 of FIG. 9) and its flanking genomic sequence. 10F–10G (SEQ ID NO: 13). Exons 10–12 (corresponding to nucleotide sequences 1117–1215, 1216–1387 and 1388–1729 of FIGS. 9A–9D, respectively) and its flanking genomic sequence.

FIGS. 12A–12C. Nucleotide and amino acid sequence of the human tub homolog 1 gene. Top line: amino acid sequence (SEQ ID NO: 15). Bottom line: nucleotide sequence (SEQ ID NO: 14). "*" represents the stop codon.

DETAILED DESCRIPTION OF THE INVENTION

Described herein are the identification of the novel mammalian tubby (tub) genes, including the human tub gene, which are involved in the control of mammalian body weight. Also described are recombinant mammalian, including human, tub DNA molecules, cloned genes, or degenerate variants thereof. The compositions of the present invention further include tub gene products (e.g., proteins) that are encoded by the tub gene, and the modulation of tub gene expression and/or tub gene product activity in the treatment of mammalian body weight, and body weight disorders, including obesity, cachexia and anorexia. Also described herein are antibodies against tub gene products (e.g., proteins), or conserved variants or fragments thereof, and nucleic acid probes useful for the identification of tub gene mutations and the use of such nucleic acid probes in diagnosing mammalian body weight disorders, including obesity, cachexia and anorexia. Further described are methods for the use of the tub gene and/or tub gene products in the identification of compounds which modulate the activity of the tub gene product.

Figure 1:
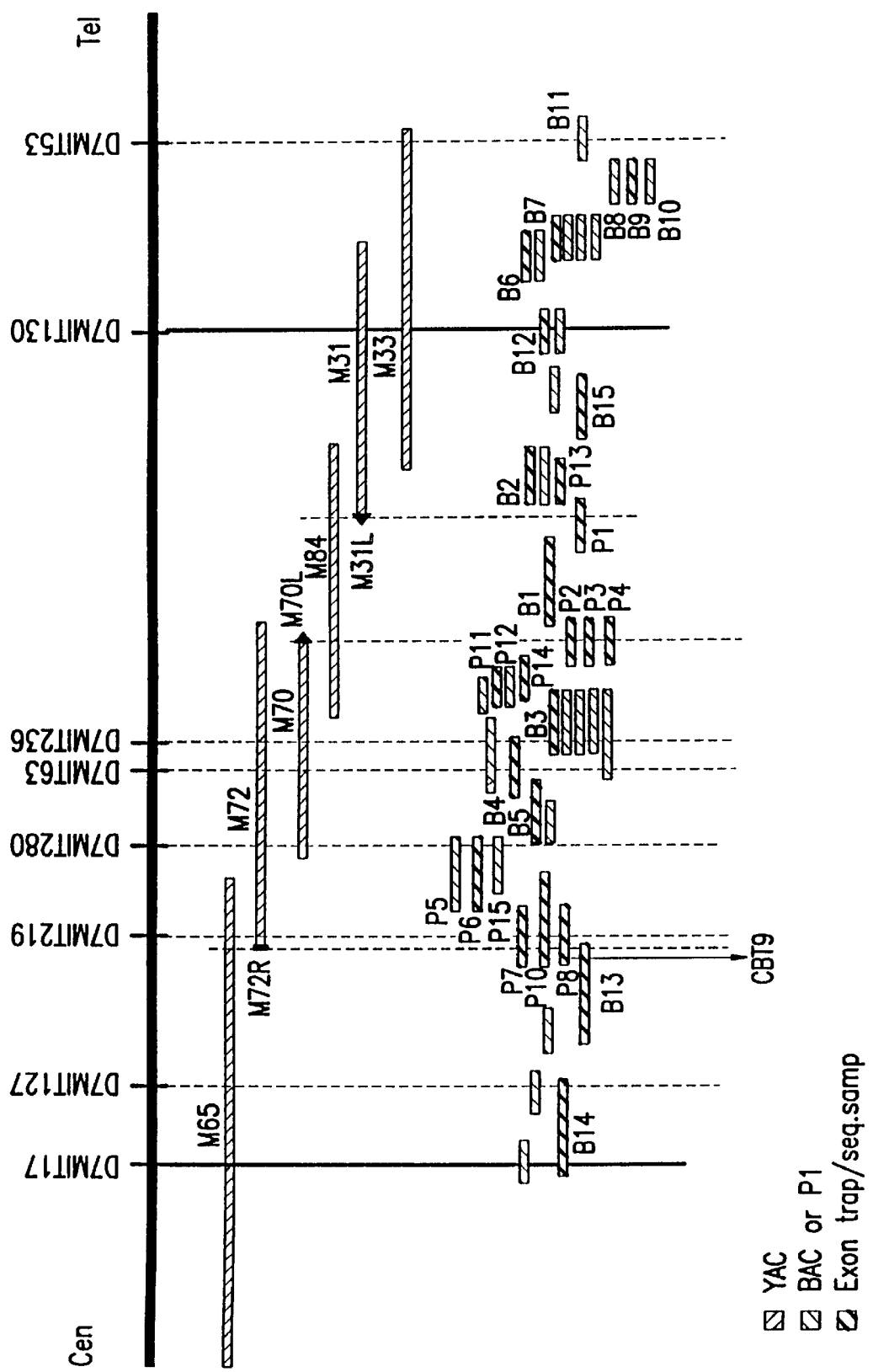
FIG. 1. Physical map of the D7Mit17 to D7Mit53 interval of mouse chromosome 7.

The murine tub nucleic acid compositions of the invention are demonstrated in the Examples presented, below, in Sections 6 through 12. The human tub nucleic acid compositions of the invention are demonstrated in Section 13, below. For clarity, it should be noted that the murine tub gene is also referred to herein as the CBT9 gene, and was identified and cloned as follows. Genetic and physical mapping of the murine tub gene interval was narrowed to the interval between markers D7Mit39 and D7Mit53. A P1 genomic clone, P8, was located within this interval, as indicated in FIG. 1. A P8 subclone, designated ium008p004, was sequenced. An analysis of ium008p004 indicated that this sequence was part of the coding region of a gene. A 90 bp fragment, designated P8X1, was amplified from this ium008p004 subclone. P8X1 was used as a probe to screen a mouse brain cDNA library, resulting in the identification of a 1.15 kb cDNA clone, designated fume009. fume009 was used as a probe to screen a mouse hypothalamus cDNA library, resulting in the identification of a 6.0 kb cDNA clone, designated fumh019. To summarize, therefore, ium008p004, PX81, fume009 and fumih019 are all part of the murine tub gene, which is also referred to herein as the CBT9 gene.

5.1. THE tub GENE

The murine tub gene, shown in FIGS. 6A–6D, and the human tub gene, shown in FIGS. 9A–9D, are novel genes involved in the control of body weight. Nucleic acid sequences of the identified tub gene are described herein. As used herein, "tub gene" refers to (a) a gene containing the DNA sequence shown in FIGS. 6A–6D or FIGS. 9A–9D or contained in the cDNA clone fumh019, CBT9H1 or CBT9H3, or genomic clone P6, P8, or B13, as deposited with the American Type Culture Collection (ATCC); (b) any DNA sequence that encodes the amino acid sequence shown in FIGS. 6A–6D or FIGS. 9A–9D, or encodes the amino acid sequence shown in FIGS. 6A–6D or FIGS. 9A–9D but lacking the amino acid residues encoded by tub exon 5 (i.e., amino acid residues 134–189 to 134–189 of FIGS. 6A–6D or FIGS. 9A–9D), or encoded by the cDNA clone fumh019, CBT9H1 or CBT9H3, or genomic clone P6, P8, or B13, as deposited with the ATCC; (c) any DNA sequence that hybridizes to the complement of the DNA sequences that encode the amino acid sequence shown in FIGS. 6A–6D or FIGS. 9A–9D, or encodes the amino acid sequence shown in FIGS. 6A–6D or FIGS. 9A–9D but lacking the amino acid residues encoded by tub exon 5 (i.e., amino acid residues 134 to 189 of FIGS. 6A–6D or FIGS. 9A–9D), or contained in the cDNA clone fumh019, CBT9H1 or CBT9H3, or genomic clone P6, P8, or B13, as deposited with the ATCC, under highly stringent conditions, e.g., hybridization to filter-bound DNA in 0.5M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a gene product functionally equivalent to a tub gene product encoded by sequences contained within the cDNA clone fumh19, CBT9H1 or CBT9H3, sequences shown in FIGS. 6A–6D or FIGS. 9A–9D, sequences shown in FIGS. 6A–6D or FIGS. 9A–9D, but lacking tub exon 5, or genomic clone P6, P8, or B13; and/or (d) any DNA sequence that hybridizes to the complement of the DNA sequences that encode the amino acid sequence shown in FIGS. 6A–6D or FIGS. 9A–9D, or encode the amino acid sequence shown in FIGS. 6A–6D or FIGS. 9A–9D but lacking the amino acid residues encoded by tub exon 5 (i.e., amino acid residues 134 to 189 of FIGS. 6A–6D or FIGS. 9A–9D), contained in the cDNA clone fumh019, CBT9H1 or CBT9H3, or genomic clone P6, P8, or B13, as deposited with the ATCC, under less stringent conditions, such as moderately stringent conditions, e.g., washing in 0.2×SSC/0.1% SDS at 42° C. (Ausubel et al., 1989, supra), yet which still encodes a functionally equivalent tub gene product. As used herein, tub gene may also refer to degenerate variants of DNA sequences (a) through (d), especially naturally occurring variants thereof.

The invention also includes nucleic acid molecules, preferably DNA molecules, that hybridize to, and are therefore the complements of, the DNA sequences (a) through (d), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as tub gene antisense molecules, useful, for example, in tub gene regulation (for and/or as antisense primers in amplification reactions of tub gene nucleic acid sequences. With respect to tub gene regulation, such techniques can be used to regulate, for example, cachexia and/or anorexia. Further, such sequences may be used as part of ribozyme and/or triple helix sequences, also useful for tub gene regulation. Still further, such molecules may be used as components of diagnostic methods whereby, for example, the presence of a particular tub allele or alternatively spliced tub transcript responsible for causing or predisposing one to a weight disorder, such as obesity, may be detected. Among the molecules which can be used for diagnostic methods such as these which involve amplification of genomic tub sequences are those listed in FIG. 10 and in Table I, below.

The invention also encompasses (a) DNA vectors that contain any of the foregoing tub coding sequences and/or their complements (i.e., antisense); (b) DNA expression vectors that contain any of the foregoing tub coding sequences operatively associated with a regulatory element that directs the expression of the coding sequences; and (c)

genetically engineered host cells that contain any of the foregoing tub coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors. The invention includes fragments of any of the DNA sequences disclosed herein.

In addition to the tub gene sequences described above, homologs of such sequences, exhibiting extensive homology to one or more of domains of the tub gene product present in other species can be identified and readily isolated, without undue experimentation, by molecular biological techniques well known in the art. Further, there can exist homolog genes at other genetic loci within the genome that encode proteins which have extensive homology to one or more domains of the tub gene product. These genes can also be identified via similar techniques.

As an example, in order to clone a human tub gene homologue using isolated murine tub gene sequences as disclosed herein, such murine tub gene sequences may be labeled and used to screen a cDNA library constructed from mRNA obtained from appropriate cells or tissues (e.g., preferably hypothalamus, or brain) derived from the organism (in this case, human) of interest. With respect to the cloning of such a human tub homologue, a human fetal brain cDNA library (e.g., Clontech #HL1149x) may, for example, be used for screening.

The hybridization washing conditions used should be of a lower stringency when the cDNA library is derived from an organism different from the type of organism from which the labeled sequence was derived. With respect to the cloning of a human tub homologue, for example, hybridization can be performed for 4 hours at 65° C. using Amersham Rapid Hyb™ buffer (Cat. #RPN1639) according to manufacturer's protocol, followed by washing, with a final washing stringency of 1.0×SSC/0.1% SDS at 50° C. for 20 minutes being preferred.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

Alternatively, the labeled fragment may be used to screen a genomic library derived from the organism of interest, again, using appropriately stringent conditions.

Further, a tub gene homologue may be isolated from nucleic acid of the organism of interest by performing PCR using two degenerate oligonucleotide primer pools designed on the basis of amino acid sequences within the tub gene product disclosed herein. The template for the reaction may be cDNA obtained by reverse transcription of mRNA prepared from, for example, human or non-human cell lines or tissue known or suspected to express a tub gene allele.

The PCR product may be subcloned and sequenced to ensure that the amplified sequences represent the sequences of a tub gene nucleic acid sequence. The PCR fragment may then be used to isolate a full length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library.

Taking, as an example, the cloning of a human tub homologue using murine tub nucleic acid sequences, among the murine tub primers which may be utilized for PCR amplification are, for example, the following, which are derived from the murine fumh019 sequence described, above:

5'- CCG ACT CGA TTG CCA GTG TA -3' (SEQ ID NO:16)
5'- GCG GAT ACA GAC TCT CTC AT -3' (SEQ ID NO:17)

These primers generate a cDNA product of approximately 950 base pairs which can then be used as probe for the screening of appropriate cDNA libraries such as, for example, human fetal brain cDNA libraries (e.g., Clontech #HL1149x). When a cDNA library is screened with probes such as this, hybridization can, for example, be performed for 4 hours at 65° C. using Amersham Rapid Hyb™ buffer (Cat. #RPN1639) according to manufacturer's protocol, followed by washing, with a final washing stringency of 1.0×SSC/0.1% SDS at 50° C. for 20 minutes being preferred.

The Example presented in Section 16, below, describes the successful identification, cloning and characterization of a human tub homolog.

PCR technology may also be utilized to isolate full length cDNA sequences. For example, RNA may be isolated, following standard procedures, from an appropriate cellular or tissue source (i.e., one known, or suspected, to express the tub gene, such as, for example, hypothalamus tissue). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see. e.g., Sambrook et al., 1989, supra.

tub gene sequences may additionally be used to isolate mutant tub gene alleles. Such mutant alleles may be isolated from individuals either known or proposed to have a genotype which contributes to the symptoms of body weight disorders such as obesity, cachexia or anorexia. Mutant alleles and mutant allele products may then be utilized in the therapeutic and diagnostic systems described below. Additionally, such tub gene sequences can be used to detect tub gene regulatory (e.g., promoter) defects which can affect body weight.

A cDNA of a mutant tub gene may be isolated, for example, by using PCR, a technique which is well known to those of skill in the art. In this case, the first cDNA strand may be synthesized by hybridizing an oligo-dT oligonucleotide to mRNA isolated from tissue known or suspected to be expressed in an individual putatively carrying the mutant tub allele, and by extending the new strand with reverse transcriptase. The second strand of the cDNA is then synthesized using an oligonucleotide that hybridizes specifically to the 5' end of the normal gene.

Using these two primers, the product is then amplified via PCR, cloned into a suitable vector, and subjected to DNA sequence analysis through methods well known to those of skill in the art. By comparing the DNA sequence of the mutant tub allele to that of the normal tub allele, the mutation(s) responsible for the loss or alteration of function of the mutant tub gene product can be ascertained.

Alternatively, a genomic library can be constructed using DNA obtained from an individual suspected of or known to carry the mutant tub allele, or a cDNA library can be constructed using RNA from a tissue known, or suspected, to express the mutant tub allele. The normal tub gene or any suitable fragment thereof may then be labeled and used as a probe to identify the corresponding mutant tub allele in such libraries. Clones containing the mutant tub gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant tub allele in an individual suspected of or known to carry such a mutant allele. In this manner, gene products made by the putatively mutant tissue may be expressed and screened using standard antibody screening techniques in conjunction with antibodies raised against the normal tub gene product, as described, below, in Section 5.3. (For screening techniques, see, for example, Harlow, E. and Lane, eds., 1988, "Antibodies: A Laboratory Manual", Cold Spring Harbor Press, Cold Spring Harbor.) In cases where a tub mutation results in an expressed gene product with altered function (e.g., as a result of a missense or a frameshift mutation), a polyclonal set of anti-tub gene product antibodies are likely to cross-react with the mutant tub gene product. Library clones detected via their reaction with such labeled antibodies can be purified and subjected to sequence analysis according to methods well known to those of skill in the art.

5.2. Protein Products of the tub Gene tub gene products, or peptide fragments thereof, can be prepared for a variety of uses. For example, such gene products, or peptide fragments thereof, can be used for the generation of antibodies, in diagnostic assays, or for the identification of other cellular gene products involved in the regulation of body weight.

The amino acid sequence depicted in FIGS. 6A–6D represents a murine tub gene product while the amino acid sequence depicted in FIGS. 9A–9D represents a human tub gene product. The tub gene product, sometimes referred to herein as a "tub protein", may additionally include those gene products encoded by the tub gene sequences described in Section 5.1, above, and is intended to include, for example, a tub gene product encoded by a tub gene sequence lacking tub exon 5.

In addition, tub gene products may include proteins that represent functionally equivalent gene products. Such an equivalent tub gene product may contain deletions, additions or substitutions of amino acid residues within the amino acid sequence encoded by the tub gene sequences described, above, in Section 5.1, but which result in a silent change, thus producing a functionally equivalent tub gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

"Functionally equivalent", as utilized herein, refers to a protein capable of exhibiting a substantially similar in vivo activity as the endogenous tub gene products encoded by the tub gene sequences described in Section 5.1, above. The in vivo activity of the tub gene product, as used herein, refers to the ability of the tub gene product, when present in an appropriate cell type, to ameliorate, prevent or delay the appearance of the obese phenotype relative to it appearance when that cell type lacks a functional tub gene product. "Obese phenotype", as used herein, refers to the well known tub phenotype, db phenotype, or ob phenotype. In humans, this can also refer to an increased percentage of body fat which is medically considered abnormal.

The tub gene products or peptide fragments thereof, may be produced by recombinant DNA technology using techniques well known in the art. Thus, methods for preparing the tub gene polypeptides and peptides of the invention by expressing nucleic acid-containing tub gene sequences are described herein. Methods which are well known to those skilled in the art can be used to construct expression vectors containing tub gene product coding sequences and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding tub gene product sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the tub gene coding sequences of the invention. Such host-expression systems represent vehicles by which the coding sequences of interest may be produced and subsequently purified, but also represent cells which may, when transformed or transfected with the appropriate nucleotide coding sequences, exhibit the tub gene product of the invention in situ. These include but are not limited to microorganisms such as bacteria (e.g., *E. coli, B. subtilis*) transformed with recombinant bacteriophage DNA, plasmid DNA or cosmid DNA expression vectors containing tub gene product coding sequences; yeast (e.g., Saccharomyces, Pichia) transformed with recombinant yeast expression vectors containing the tub gene product coding sequences; insect cell systems infected with recombinant virus expression vectors (e.g., baculovirus) containing the tub gene product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing tub gene product coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the tub gene product being expressed. For example, when a large quantity of such a protein is to be produced, for the generation of pharmaceutical compositions of tub protein or for raising antibodies to tub protein, for example, vectors which direct the expression of high levels of fusion protein products that are readily purified may be desirable. Such vectors include, but are not limited to, the *E. coli* expression vector pUR278 (Ruther et al., 1983, EMBO J. 2:1791), in which the tub gene product coding sequence may be ligated individually into the vector in frame with the lac Z coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety. The Example presented in Section 15, below, describes the successful expression of both murine and human recombinant tub gene products utilizing modified pET vectors (Novagen, Inc., Madison, Wis.).

In an insect system, *Autographa californica* nuclear polyhedrosis virus (AcNPV) is used as a vector to express foreign genes. The virus grows in *Spodoptera frugiperda* cells. The tub gene coding sequence may be cloned individually into non-essential regions (for example the polyhedrin gene) of the virus and placed under control of an AcNPV promoter (for example the polyhedrin promoter). Successful insertion of tub gene coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (E.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the tub gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing tub gene product in infected hosts. (E.g., See Logan & Shenk, 1984, Proc. Natl. Acad. Sci. USA 81:3655–3659). Specific initiation signals may also be required for efficient translation of inserted tub gene product coding sequences. These signals include the ATG initiation codon and adjacent sequences. In cases where an entire tub gene, including its own initiation codon and adjacent sequences, is inserted into the appropriate expression vector, no additional translational control signals may be needed. However, in cases where only a portion of the tub gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, and in particular, hypothalamic cell lines such as GN and GH-1 cell lines.

For long-term, high-yield production of recombinant proteins, stable expression is preferred. For example, cell lines which stably express the tub gene product may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the tub gene product. Such engineered cell lines may be particularly useful in screening and evaluation of compounds that affect the endogenous activity of the tub gene product.

The Example presented in Section 15, below, describes the successful expression of recombinant tub gene products in mammalian cell lines.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88: 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers. The Example presented in Section 15, below, demonstrates the successful expression of carboxy-terminal histidine-tagged recombinant tub gene products.

The tub gene products can also be expressed in transgenic animals. Animals of any species, including, but not limited to, mice, rats, rabbits, guinea pigs, pigs, micro-pigs, goats, and non-human primates, e.g., baboons, monkeys, and chimpanzees may be used to generate tub transgenic animals.

Any technique known in the art may be used to introduce the tub gene transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the tub transgene in all their cells, as well as animals which carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al., 1992, Proc. Natl. Acad. Sci. USA 89: 6232–6236). The regulatory sequences required for such a cell-type specific activation will depend upon the particular cell type of interest, and will be apparent to those of skill in the art. When it is desired that the tub gene transgene be integrated into the chromosomal site of the endogenous tub gene, gene targeting is preferred. Briefly, when such a technique is to be utilized, vectors containing some nucleotide sequences homologous to the endogenous tub gene are designed for the purpose of integrating, via homologous recombination with chromosomal sequences, into and disrupting the function of the nucleotide sequence of the endogenous tub gene. The transgene may also be selectively introduced into a particular cell type, thus inactivating the endogenous tub gene in only that cell type, by following, for example, the teaching of Gu et al. (Gu, et al., 1994, Science 265: 103–106). The regulatory sequences required for such a cell-type specific inactivation will depend upon the particular cell type of interest, and will be apparent to those of skill in the art.

Once transgenic animals have been generated, the expression of the recombinant tub gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of tub gene-expressing tissue, may also be evaluated immunocytochemically using antibodies specific for the tub transgene product.

5.3. Antibodies to tub Gene Products

Described herein are methods for the production of antibodies capable of specifically recognizing one or more tub gene product epitopes or epitopes of conserved variants or peptide fragments of the tub gene products.

Such antibodies may include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be used, for example, in the detection of a tub gene product in an biological sample and may, therefore, be utilized as part of a diagnostic or prognostic technique whereby patients may be tested for abnormal levels of tub gene products, and/or for the presence of abnormal forms of the such gene products. Such antibodies may also be utilized in conjunction with, for example, compound screening schemes, as described, below, in Section 5.4.2, for the evaluation of the effect of test compounds on tub gene product levels and/or activity. Additionally, such antibodies can be used in conjunction with the gene therapy techniques described, below, in Section 5.4.3, to, for example, evaluate the normal and/or engineered tub-expressing cells prior to their introduction into the patient.

Anti-tub gene product antibodies may additionally be used as a method for the inhibition of abnormal tub gene product activity. Thus, such antibodies may, therefore, be utilized as part of weight disorder treatment methods.

For the production of antibodies against a tub gene product, various host animals may be immunized by injection with a tub gene product, or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

Polyclonal antibodies are heterogeneous populations of antibody molecules derived from the sera of animals immunized with an antigen, such as a tub gene product, or an antigenic functional derivative thereof. For the production of polyclonal antibodies, host animals such as those described above, may be immunized by injection with tub gene product supplemented with adjuvants as also described above.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against tub gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity.

5.4. Uses of the tub Gene, Gene Products, and Antibodies

Described herein are various applications of the tub gene, the tub gene product including peptide fragments thereof, and of antibodies directed against the tub gene product and peptide fragments thereof. Such applications include, for example, prognostic and diagnostic evaluation of body weight disorders and the identification of subjects with a predisposition to such disorders, as described, below, in Section 5.4.1. Additionally, such applications include methods for the treatment of body weight and body weight disorders, as described, below, in Section 5.4.2, and for the identification of compounds which modulate the expression of the tub gene and/or the activity of the tub gene product, as described below, in Section 5.4.3. Such compounds can include, for example, other cellular products which are involved in body weight regulation. These compounds can be used, for example, in the amelioration of body weight disorders including obesity, cachexia and anorexia.

While, for clarity, uses related to body weight disorder abnormalities are primarily described in this Section, it is to be noted that each of the diagnostic and therapeutic treatments described herein can additionally be utilized in connection with sensory (e.g., eye and hearing) and fertility defects that are commonly associated with mutations in the tub gene. That is, the diagnostic and prognostic techniques described herein can also be utilized to diagnose tub related eye, hearing and fertility abnormalities and/or a predisposition toward the development of such eye, hearing and fertility abnormalities, while the therapeutic techniques described herein can be utilized for the amelioration of such eye, hearing and fertility defects.

5.4.1 Diagnosis of Body Weight Disorder Abnormalities

A variety of methods can be employed for the diagnostic and prognostic evaluation of body weight disorders, including obesity, cachexia and anorexia, and for the identification of subjects having a predisposition to such disorders.

Such methods may, for example, utilize reagents such as the tub gene nucleotide sequences described in Sections 5.1, and antibodies directed against tub gene products, including peptide fragments thereof, as described, above, in Section 5.3. Specifically, such reagents may be used, for example, for: (1) the detection of the presence of tub gene mutations, or the detection of either over- or under-expression of tub gene mRNA relative to the non-body weight disorder state or the qualitative or quantitative detection of alternatively spliced forms of tub transcripts which may correlate with certain body weight disorders or susceptibility toward such body weight disorders; and (2) the detection of either an over- or an under-abundance of tub gene product relative to the non-body weight disorder state or the presence of a modified (e.g., less than full length) tub gene product which correlates with a body weight disorder state or a progression toward a body weight disorder state.

The methods described herein may be performed, for example, by utilizing pre-packaged diagnostic kits comprising at least one specific tub gene nucleic acid or anti-tub gene antibody reagent described herein, which may be conveniently used, e.g., in clinical settings, to screen and diagnose patients exhibiting body weight disorder abnormalities and to screen and identify those individuals exhibiting a predisposition to developing a body weight disorder abnormality.

For the detection of tub mutations, any nucleated cell can be used as a starting source for genomic nucleic acid. For the detection of tub transcripts or tub gene products, any cell type or tissue in which the tub gene is expressed, such as, for example, hypothalamus cells, may be utilized.

Nucleic acid-based detection techniques are described, below, in Section 5.4.1.1. Peptide detection techniques are described, below, in Section 5.4.1.2.

5.4.1.1 Detection of tub Gene Nucleic Acid Molecules

Mutations or polymorhisms within the tub gene can be detected by utilizing a number of techniques. Nucleic acid from any nucleated cell can be used as the starting point for such assay techniques, and may be isolated according to standard nucleic acid preparation procedures which are well known to those of skill in the art.

Genomic DNA may be used in hybridization or amplification assays of biological samples to detect abnormalities involving tub gene structure, including point mutations, insertions, deletions and chromosomal rearrangements. Such assays may include, but are not limited to, direct sequencing (Wong, C. et al., 1987, Nature 330:384–386), single stranded conformational polymorphism analyses (SSCP; Orita, M. et al., 1989, Proc. Natl. Acad. Sci. USA 86:2766–2770), heteroduplex analysis (Keen, T. J. et al., 1991, Genomics 11:199–205; Perry, D. J. & Carrell, R. W., 1992), denaturing gradient gel electrophoresis (DGGE; Myers, R. M. et al., 1985, Nucl. Acids Res. 13:3131–3145), chemical mismatch cleavage (Cotton, R. G. et al., 1988, Proc. Natl. Acad. Sci. USA 85:4397–4401) and oligonucleotide hybridization (Wallace, R. B. et al., 1981, Nucl. Acids Res. 9:879–894; Lipshutz, R. J. et al., 1995, Biotechniques 19:442–447).

Diagnostic methods for the detection of tub gene specific nucleic acid molecules, in patient samples or other appropriate cell sources, may involve the amplification of specific gene sequences, e.g., by the polymerase chain reaction (PCR; the experimental embodiment set forth in Mullis, K. B., 1987, U.S. Pat. No. 4,683,202), followed by the analysis of the amplified molecules using techniques well known to those of skill in the art, such as, for example, those listed above. Utilizing analysis techniques such as these, the amplified sequences can be compared to those which would be expected if the nucleic acid being amplified contained only normal copies of the tub gene in order to determine whether a tub gene mutation exists.

Among those tub nucleic acid sequences which are preferred for such amplification-related diagnostic screening analyses are oligonucleotide primers which amplify tub exon sequences. The sequence of such oligonucleotide primers are, therefore, preferably derived from tub intron sequence so that the enire exon (or coding region) can be analyzed, as discussed below. Primer pairs useful for amplification of tub exons are preferably derived from adjacent introns. For example, in order to amplify tub exon 5, a forward primer derived from the tub intron upstream of exon 5 (i.e., the intron between tub exon 4 and 5) could be used in conjunction with a reverse primer derived from the tub intron downstream of exon 5 (i.e., the intron between tub exon 5 and 6).

Appropriate primer pairs can be chosen such that each of the twelve tub exons are amplified. FIGS. 10A–10G depicts each of human tub exons 4 through 12 and, further, depicts intron sequences flanking each of these exons. Primers for the amplification of tub exons can routinely be designed by one of skill in the art by utilizing such intron flanking sequence.

As an example, and not by way of limitation, Table I, below, lists primers and primer pairs which can be utilized for the amplification of each of human tub exons 2 through 12. In this table, a primer pair is listed for each of exons 2 through 12, which consists of a forward primer derived from intron sequence upstream of the exon to be amplified and a reverse primer derived from sequence downstream of the exon to be amplified. Each of the primer pairs can be utilized, therefore, as part of a standard PCR reaction to amplify an individual tub exon. For each of the primer pairs listed in Table I, the approximate size of the resulting amplified exon-containing fragment is listed. Utilizing the primer pairs of Table I to amplify human tub exon 5, for example, primers F5 (the forward primer) and R5 (the reverse primer) would be used to amplify a fragment of approximately 250 base pairs that would contain the entire coding region of exon 5.

TABLE I

| HUMAN TUB EXON | PRIMER NAME AND SEQUENCE | | | AMPLIFIED FRAGMENT SIZE |
|---|---|---|---|---|
| 2 | F2 (SEQ ID NO: 18) | 5'-GTT CAA GCT GGT TTC AAG ATG-3' | | F2/R2 = 200 bp |
|   | R2 (SEQ ID NO: 19) | 5'-ATC ATC CAG GGA AGA TGG AC-3' | | |
| 3 | F3 (SEQ ID NO: 20) | 5'-CTT CCT GGT GGA GGC AGT G-3' | | F3/R3 = 220 bp |
|   | R3 (SEQ ID NO: 21) | 5'-GAA GCA GTG ACG GGA TGT GG-3' | | |
| 4 | F4 (SEQ ID NO: 22) | 5'-GGG TAC CGA GCT CTG GTC-3' | | F4/R4 = 295 bp |
|   | R4 (SEQ ID NO: 23) | 5'-TCC AAG TCA GGA GGA CAA AC-3' | | |
| 5 | F5 (SEQ ID NO: 24) | 5'-GAA AGT GCA TCT GAG AAC CTG-3' | | F5/R5 = 250 bp |
|   | R5 (SEQ ID NO: 25) | 5'-CCT CCT CCT GGA TGT AAC TC-3' | | |
| 6 | F6 (SEQ ID NO: 26) | 5'-TGT GAC CAT GTG TAT TTC AGG-3' | | F6/R6 = 234 bp |
|   | R6 (SEQ ID NO: 27) | 5'-CCT CTA ACG GAT GAG CAG TC-3' | | |
| 7 | F7 (SEQ ID NO: 28) | 5'-GAT TTG GAT CCC AGA CCA CC-3' | | F7/R7 = 331 bp |
|   | R7 (SEQ ID NO: 29) | 5'-GAC TTC CAG TCA CAT TTC AGC-3' | | |
| 8 | F8 (SEQ ID NO: 30) | 5'-GTG CAG ACC AGA GGC TGA G-3' | | F8/R8 = 300 bp |
|   | R8 (SEQ ID NO: 31) | 5'-TTC AGG CCC TCT ACA GAC AG-3' | | |
| 9 | F9 (SEQ ID NO: 32) | 5'-TCA TAG GAC AGA CGA TGA GC-3' | | F9/R9 = 210 bp |
|   | R9 (SEQ ID NO: 33) | 5'-GTC CTG GAT TTC ATA TCT ACC-3' | | |
| 10 | F10 (SEQ ID NO: 34) | 5'-AGG TAA ATA GAC GCC TCA GC-3' | | F10/R10 = 218 bp |
|   | R10 (SEQ ID NO: 35) | 5'-ACG TCT GCC CTT AGA AGC TC-3' | | |
| 11 | F11 (SEQ ID NO: 36) | 5'-CTG GAC CTG GCT CAG GTG-3' | | F11/R11 = 400 bp |
|   | R11 (SEQ ID NO: 37) | 5'-GTC ATT AGG GTT AGA AAG TTC C-3' | | |
| 12 | F12 (SEQ ID NO: 38) | 5'-TCT TCC CTC ATG TGG TTT GG-3' | | F12/R12 = 300 bp |
|   | R12 (SEQ ID NO: 39) | 5'-CCA CAG GCA GGC AGG CAA G-3' | | |

Additional tub nucleic acid sequences which are preferred for such amplification-related analyses are those which will detect the presence of the tub gene splice site mutation described, below, in Section 10.2 and depicted in FIG. 7.

Further, well-known genotyping techniques can be performed to type polymorphisms that are in close proximity to mutations in the tub gene itself. These polymorphisms can be used to identify individuals in families likely to carry mutations. If a polymorphism exhibits linkage disequilibrium with mutations in the tub gene, it can also be used to identify individuals in the general population likely to carry mutations. Polymorphisms that can be used in this way include restriction fragment length polymorphisms (RFLPs), which involve sequence variations in restriction enzyme target sequences, single-base polymorphisms and simple sequence repeat polymorphisms (SSLPs).

For example, Weber (U.S. Pat. No. 5,075,217, which is incorporated herein by reference in its entirety) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers which are so closely spaced exhibit a high frequency co-inheritance, and are extremely useful in the identification of genetic mutations, such as, for example, mutations within the tub gene, and the diagnosis of diseases and disorders related to tub mutations.

Also, Caskey et al. (U.S. Pat. No. 5,364,759, which is incorporated herein by reference in its entirety) describe a DNA profiling assay for detecting short tri and tetra nucleotide repeat sequences. The process includes extracting the DNA of interest, such as the tub gene, amplifying the extracted DNA, and labelling the repeat sequences to form a genotypic map of the individual's DNA.

A tub probe could additionally be used to directly identify RFLPs. Additionally, a tub probe or primers derived from the tub sequence could be used to isolate genomic clones such as YACs, BACs, PACs, cosmids, phage or plasmids. The DNA contained in these clones can be screened for single-base polymorphisms or simple sequence length polymorphisms (SSLPs) using standard hybridization or sequencing procedures.

Alternative diagnostic methods for the detection of tub gene-specific mutations or polymorphisms can include hybridization techniques which involve for example, contacting and incubating nucleic acids including recombinant DNA molecules, cloned genes or degenerate variants thereof, obtained from a sample, e.g., derived from a patient sample or other appropriate cellular source, with one or more labeled nucleic acid reagents including recombinant DNA molecules, cloned genes or degenerate variants thereof, as described in Section 5.1, under conditions favorable for the specific annealing of these reagents to their complementary sequences within the tub gene. Preferably, the lengths of these nucleic acid reagents are at least 15 to 30 nucleotides. After incubation, all non-annealed nucleic acids are removed from the nucleic acid:tub molecule hybrid. The presence of nucleic acids which have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described in Section 5.1 are easily removed. Detection of the remaining, annealed, labeled tub nucleic acid reagents is accomplished using standard techniques well-known to those in the art. The tub gene sequences to which the nucleic acid reagents have annealed can be compared to the annealing pattern expected from a normal tub gene sequence in order to determine whether a tub gene mutation is present.

Among the tub nucleic acid sequences which are preferred for such hybridization analyses are those which will detect the presence of the tub gene splice site mutation described, below, in Section 10.2 and depicted in FIGS. 7A–7D.

Quantitative and qualitative aspects of tub gene expression can also be assayed. For example, RNA from a cell type or tissue known, or suspected, to express the tub gene, such as brain, especially hypothalamus cells, may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the tub gene. Such analyses may reveal both quantitative and qualitative aspects of the expression pattern of the tub gene, including activation or inactivation of tub gene expression and presence of alternatively spliced tub transcripts.

In one embodiment of such a detection scheme, a cDNA molecule is synthesized from an RNA molecule of interest (e.g., by reverse transcription of the RNA molecule into cDNA). All or part of the resulting cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the tub gene nucleic acid reagents described in Section 5.1. The preferred lengths of such nucleic acid reagents are at least 9–30 nucleotides.

For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Such RT-PCR techniques can be utilized to detect differences in tub transcript size which may be due to normal or abnormal alternative splicing. Additionally, such techniques can be performed using standard techniques to detect quantitative differences between levels of full length and/or alternatively spliced tub transcripts detected in normal individuals relative to those individuals exhibiting body weight disorders or exhibiting a predisposition to toward such body weight disorders.

In the case where detection of specific alternatively spliced species is desired, appropriate primers and/or hybridization probes can be used. Using the detection of transcripts containing tub exon 5, for example, appropriate amplification primers can be chosen which will only yield an amplified fragment using cDNA derived from an exon 5-containing transcript. One of the primer pairs can be designed, for example, to specifically utilize an exon 5 sequence. In the absence of such sequence, no amplification would occur. Alternatively, primer pairs may be chosen utilizing the sequence data depicted in FIGS. 6A–6D and 9A–9D to choose primers which will yield fragments of differing size depending on whether exon 5 is present or absent from the transcript tub transcript being utilized.

As an alternative to amplification techniques, standard Northern analyses can be performed if a sufficient quantity of the appropriate cells can be obtained. Utilizing such techniques, quantitative as well as size related differences between tub transcripts can also be detected.

Additionally, it is possible to perform such tub gene expression assays "in situ", i.e., directly upon tissue sections (fixed and/or frozen) of patient tissue obtained from biopsies or resections, such that no nucleic acid purification is necessary. Nucleic acid reagents such as those described in Section 5.1 may be used as probes and/or primers for such in situ procedures (see, for example, Nuovo, G. J., 1992, "PCR In Situ Hybridization: Protocols And Applications", Raven Press, NY).

5.4.1.2. Detection of tub Gene Products

Antibodies directed against wild type or mutant tub gene products or conserved variants or peptide fragments thereof, which are discussed, above, in Section 5.3, may also be used as body weight disorder diagnostics and prognostics, as described herein. Such diagnostic methods, may be used to detect abnormalities in the level of tub gene expression, or abnormalities in the structure and/or temporal, tissue, cellular, or subcellular location of tub gene product. Because evidence disclosed herein indicates that the tub gene product is an intracellular gene product, the antibodies and immunoassay methods described below have important in vitro applications in assessing the efficacy of treatments for body-weight disorders such as obesity, cachexia and anorexia. Antibodies, or fragments of antibodies, such as those described below, may be used to screen potentially therapeutic compounds in vitro to determine their effects on tub gene expression and tub peptide production. The compounds which have beneficial effects on body weight disorders, such as obesity, cachexia and anorexia, can be identified, and a therapeutically effective dose determined.

In vitro immunoassays may also be used, for example, to assess the efficacy of cell-based gene therapy for body weight disorders, including obesity, cachexia and anorexia. Antibodies directed against tub peptides may be used in vitro to determine the level of tub gene expression achieved in cells genetically engineered to produce tub peptides. Given that evidence disclosed herein indicates that the tub gene product is an intracellular gene product, such an assessment is, preferably, done using cell lysates or extracts. Such analysis will allow for a determination of the number of transformed cells necessary to achieve therapeutic efficacy in vivo, as well as optimization of the gene replacement protocol.

The tissue or cell type to be analyzed will generally include those which are known, or suspected, to express the tub gene, such as, for example, hypothalamic cells. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety. The isolated cells can be derived from cell culture or from a patient. The analysis of cell taken from culture may be a necessary step in the assessment of cells to be used as part of a cell-based gene therapy technique or, alternatively, to test the effect of compounds on the expression of the tub gene.

Preferred diagnostic methods for the detection of tub gene products or conserved variants or peptide fragments thereof, may involve, for example, immunoassays wherein the tub gene products or conserved variants, including gene products which are the result of alternatively spliced transcripts, or peptide fragments are detected by their interaction with an anti-tub gene product-specific antibody.

For example, antibodies, or fragments of antibodies, such as those described, above, in Section 5.3, useful in the present invention may be used to quantitatively or qualitatively detect the presence of tub gene products or conserved variants or peptide fragments thereof. This can be accomplished, for example, by immunofluorescence techniques employing a fluorescently labeled antibody (see below, this Section) coupled with light microscopic, flow cytometric, or fluorimetric detection. Such techniques are especially preferred if such tub gene products are expressed on the cell surface.

The antibodies (or fragments thereof) useful in the present invention may, additionally, be employed histologically, as in immunofluorescence or immunoelectron microscopy, for in situ detection of tub gene products or conserved variants or peptide fragments thereof. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the tub gene product, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays for tub gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying tub gene products or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled tub gene specific antibody. The solid phase support may then be washed with the buffer a second time to remove unbound antibody. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-tub gene product antibody may be determined according to well known methods. Those skilled in the art will be able to determine operative and optimal assay conditions for each determination by employing routine experimentation.

One of the ways in which the tub gene peptide-specific antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, Md.); Voller, A. et al., 1978, J. Clin. Pathol. 31:507–520; Butler, J. E., 1981, Meth. Enzymol. 73:482–523; Maggio, E. (ed.), 1980, Enzyme Immunoassay, CRC Press, Boca Raton, Fla.; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect tub gene peptides through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.4.2. Screening Assays for Compounds that Modulate tub Gene Activity

The following assays are designed to identify compounds that bind to tub gene products, bind to other intracellular proteins that interact with a tub gene product, to compounds that interfere with the interaction of the tub gene product with other intracellular proteins and to compounds which modulate the activity of tub gene (i.e., modulate the level of tub gene expression and/or modulate the level of tub gene product activity). Assays may additionally be utilized which identify compounds which bind to tub gene regulatory sequences (e.g., promoter sequences). See e.g., Platt, K. A., 1994, J. Biol. Chem. 269:28558–28562, which is incorporated herein by reference in its entirety, which may modulate the level of tub gene expression. Compounds may include, but are not limited to, small organic molecules which are able to cross the blood-brain barrier, gain entry into an appropriate cell and affect expression of the tub gene or some other gene involved in the body weight regulatory pathway, or other intracellular proteins. Methods for the identification of such intracellular proteins are described, below, in Section 5.4.2.2. Such intracellular proteins may be involved in the control and/or regulation of body weight. Further, among these compounds are compounds which affect the level of tub gene expression and/or tub gene product activity and which can be used in the therapeutic treatment of body weight disorders, including obesity, cachexia and anorexia, as described, below, in Section 5.4.3.

Compounds may include, but are not limited to, peptides such as, for example, soluble peptides, including but not limited to, Ig-tailed fusion peptides, and members of random peptide libraries; (see, e.g., Lam, K. S. et al., 1991, Nature 354:82–84; Houghten, R. et al., 1991, Nature 354:84–86), and combinatorial chemistry-derived molecular library made of D-and/or L- configuration amino acids, phosphopeptides (including, but not limited to members of random or partially degenerate, directed phosphopeptide libraries; see, e.g., Songyang, Z. et al., 1993, Cell 72:767–778), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

Compounds identified via assays such as those described herein may be useful, for example, in elaborating the biological function of the tub gene product, and for ameliorating body weight disorders. Assays for testing the effectiveness of compounds, identified by, for example, techniques such as those described in Section 5.4.2.1–5.4.2.3, are discussed, below, in Section 5.4.2.4.

5.4.2.1. In Vitro Screening Assays for Compounds that bind to the tub Gene Product In vitro systems may be designed to identify compounds capable of binding the tub gene products of the invention. Compounds identified may be useful, for example, in modulating the activity of wild type and/or mutant tub gene products, may be useful in elaborating the biological function of the tub gene product, may be utilized in screens for identifying compounds that disrupt normal tub gene product interactions, or may in themselves disrupt such interactions.

The principle of the assays used to identify compounds that bind to the tub gene product involves preparing a reaction mixture of the tub gene product and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring tub gene product or the test substance onto a solid phase and detecting tub gene product/test compound complexes anchored on the solid phase at the end of the reaction. In one embodiment of such a method, the tub gene product may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for tub gene product or the test compound to anchor any complexes formed in solution, and a labeled antibody specific for the other component of the possible complex to detect anchored complexes.

5.4.2.2. Assays for Intracellular Proteins that Interact with the Tub Gene Product Any method suitable for detecting protein-protein interactions may be employed for identifying tub protein-intracellular protein interactions.

Among the traditional methods which may be employed are co-immunoprecipitation, crosslinking and co-purification through gradients or chromatographic columns. Utilizing procedures such as these allows for the identification of intracellular proteins which interact with tub gene products. Once isolated, such an intracellular protein can be identified and can, in turn, be used, in conjunction with standard techniques, to identify proteins it interacts with. For example, at least a portion of the amino acid sequence of the intracellular protein which interacts with the tub gene product can be ascertained using techniques well known to those of skill in the art, such as via the Edman degradation technique (see, e.g., Creighton, 1983, "Proteins: Structures and Molecular Principles", W. H. Freeman & Co., N.Y., pp.34–49). The amino acid sequence obtained may be used as a guide for the generation of oligonucleotide mixtures that can be used to screen for gene sequences encoding such intracellular proteins. Screening made be accomplished, for example, by standard hybridization or PCR techniques. Techniques for the generation of oligonucleotide mixtures and the screening are well-known. (See, e.g., Ausubel, supra., and PCR Protocols: A Guide to Methods and Applications, 1990, Innis, M. et al., eds. Academic Press, Inc., New York).

Additionally, methods may be employed which result in the simultaneous identification of genes which encode the intracellular protein interacting with the tub protein. These methods include, for example, probing expression libraries with labeled tub protein, using tub protein in a manner similar to the well known technique of antibody probing of λgt11 libraries.

One method which detects protein interactions in vivo, the two-hybrid system, is described in detail for illustration only and not by way of limitation. One version of this system has been described (Chien et al., 1991, Proc. Natl. Acad. Sci. USA, 88:9578–9582) and is commercially available from Clontech (Palo Alto, Calif.).

Briefly, utilizing such a system, plasmids are constructed that encode two hybrid proteins: one consists of the DNA-binding domain of a transcription activator protein fused to the tub gene product and the other consists of the transcription activator protein's activation domain fused to an unknown protein that is encoded by a cDNA which has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, tub gene products may be used as the bait gene product. Total genomic or cDNA sequences are fused to the DNA encoding an activation domain. This library and a plasmid encoding a hybrid of a bait tub gene product fused to the DNA-binding domain are cotransformed into a yeast reporter strain, and the resulting transformants are screened for those that express the reporter gene. For example, and not by way of limitation, a bait tub gene sequence, such as the 1.5 kb open reading frame of the tub gene, as depicted in FIG. 6 or FIG. 9 can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait tub gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait tub gene-GAL4 fusion plasmid into a yeast strain which contains a lacZ gene driven by a promoter which contains GAL4 activation sequence. A cDNA encoded protein, fused to GAL4 transcriptional activation domain, that interacts with bait tub gene product will reconstitute an active GAL4 protein and thereby drive expression of the HIS3 gene. Colonies which express HIS3 can be detected by their growth on petri dishes containing semi-solid agar based media lacking histidine. The cDNA can then be purified from these strains, and used to produce and isolate the bait tub gene-interacting protein using techniques routinely practiced in the art.

5.4.2.3. Assays for Compounds that Interfere with Tub Gene Product/Intracellular Macromolecule Interaction The tub gene products of the invention may, in vivo, interact with one or more intracellular macromolecules, such as proteins. Such macromolecules may include, but are not limited to, nucleic acid molecules and those proteins identified via methods such as those described, above, in Section 5.4.2.2. For purposes of this discussion, such intracellular macromolecules are referred to herein as "binding partners". Compounds that disrupt tub binding in this way may be useful in regulating the activity of the tub gene product, especially mutant tub gene products. Such compounds may include, but are not limited to molecules such as peptides, and the like, as described, for example, in Section 5.4.2.1. above, which would be capable of gaining access to the intracellular tub gene product.

The basic principle of the assay systems used to identify compounds that interfere with the interaction between the tub gene product and its intracellular binding partner or partners involves preparing a reaction mixture containing the tub gene product, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of tub gene product and its intracellular binding partner. Control reaction mixtures are incubated without the test compound or with a placebo. The formation of any complexes between the tub gene protein and the intracellular binding partner is then detected. The formation of a complex in the control reaction, but not in the reaction mixture containing the test compound, indicates that the compound interferes with the interaction of the tub gene protein and the interactive binding partner. Additionally, complex formation within reaction mixtures containing the test compound and normal tub gene protein may also be compared to complex formation within reaction mixtures containing the test compound and a mutant tub gene protein. This comparison may be important in those cases wherein it is desirable to identify compounds that disrupt interactions of mutant but not normal tub gene proteins.

The assay for compounds that interfere with the interaction of the tub gene products and binding partners can be conducted in a heterogeneous or homogeneous format. Heterogeneous assays involve anchoring either the tub gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the tub gene products and the binding partners, e.g., by competition, can be identified by conducting the reaction in the presence of the test substance; i.e., by adding the test substance to the reaction mixture prior to or simultaneously with the tub gene protein and interactive intracellular binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the tub gene product or the interactive intracellular binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the tub gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the tub gene protein and the interactive intracellular binding partner is prepared in which either the tub gene product or its binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt tub gene protein/intracellular binding partner interaction can be identified.

In a particular embodiment, the tub gene product can be prepared for immobilization using recombinant DNA techniques described in Section 5.2. above. For example, the tub coding region can be fused to a glutathione-S-transferase (GST) gene using a fusion vector, such as pGEX-5X-1, in such a manner that its binding activity is maintained in the resulting fusion protein. The interactive intracellular binding partner can be purified and used to raise a monoclonal antibody, using methods routinely practiced in the art and described above, in Section 5.3. This antibody can be labeled with the radioactive isotope $^{125}$I, for example, by methods routinely practiced in the art. In a heterogeneous assay, e.g., the GST-tub fusion protein can be anchored to glutathione-agarose beads. The interactive intracellular binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the tub gene protein and the interactive intracellular binding partner can be detected by measuring the amount of radioactivity that remains associated with the glutathione-agarose beads. A successful inhibition of the interaction by the test compound will result in a decrease in measured radioactivity.

Alternatively, the GST-tub gene fusion protein and the interactive intracellular binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the tub gene product/binding partner interaction can be detected by adding the labeled antibody and measuring the radioactivity associated with the beads.

In another embodiment of the invention, these same techniques can be employed using peptide fragments that correspond to the binding domains of the tub protein and/or the interactive intracellular or binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the intracellular binding partner is obtained, short gene segments can be engineered to express peptide fragments of the protein, which can then be tested for binding activity and purified or synthesized.

For example, and not by way of limitation, a tub gene product can be anchored to a solid material as described, above, in this Section by making a GST-tub fusion protein and allowing it to bind to glutathione agarose beads. The interactive intracellular binding partner can be labeled with a radioactive isotope, such as $^{35}$S, and cleaved with a proteolytic enzyme such as trypsin. Cleavage products can then be added to the anchored GST-tub fusion protein and allowed to bind. After washing away unbound peptides, labeled bound material, representing the intracellular binding partner binding domain, can be eluted, purified, and analyzed for amino acid sequence by well-known methods. Peptides so identified can be produced synthetically or fused to appropriate facilitative proteins using recombinant DNA technology.

5.4.2.4. Assays for Identification of Compounds that Ameliorate Body Weight Disclosure Compounds, including but not limited to binding compounds identified via assay techniques such as those described, above, in Sections 5.4.2.1–5.4.2.3, can be tested for the ability to ameliorate body weight disorder symptoms, including obesity. It should be noted that although tub gene products are intracellular molecules which are not secreted and have no transmembrane component, the assays described herein can identify compounds which affect tub gene activity by either affecting tub gene expression or by affecting the level of tub gene product activity. For example, compounds may be identified which are involved in another step in the pathway in which the tub gene and/or tub gene product is involved and, by affecting this same pathway may modulate the affect of tub on the development of body weight disorders. Such compounds can be used as part of a therapeutic method for the treatment of body weight disorders.

Described below are cell-based and animal model-based assays for the identification of compounds exhibiting such an ability to ameliorate body weight disorder symptoms.

First, cell-based systems can be used to identify compounds which may act to ameliorate body weight disorder symptoms. Such cell systems can include, for example, recombinant or non-recombinant cell, such as cell lines, which express the tub gene. For example, hypothalamus cells, such as, for example GH-1 (Melcang; R. C. et al., 1995, Endocrinology 136:679–686) and GN (Radovick, S. et al., 1991, Proc. Natl. Acad. Sci. USA 88:3402–3406) hypothalamic cell lines can be used.

In utilizing such cell systems, cells may be exposed to a compound, suspected of exhibiting an ability to ameliorate body weight disorder symptoms, at a sufficient concentration and for a time sufficient to elicit such an amelioration of body weight disorder symptoms in the exposed cells. After exposure, the cells can be assayed to measure alterations in the expression of the tub gene, e.g., by assaying cell lysates for tub mRNA transcripts (e.g., by Northern analysis) or for tub protein expressed in the cell; compounds which increase expression of the tub gene are good candidates as therapeutics. Alternatively, the cells are examined to determine whether one or more body weight disorder-like cellular phenotypes has been altered to resemble a more normal or more wild type, non-body weight disorder phenotype, or a phenotype more likely to produce a lower incidence or severity of disorder symptoms.

In addition, animal-based body weight disorder systems, which may include, for example tub mice, may be used to identify compounds capable of ameliorating body weight disorder-like symptoms. Such animal models may be used as test substrates for the identification of drugs, pharmaceuticals, therapies and interventions which may be effective in treating such disorders. For example, animal models may be exposed to a compound, suspected of exhibiting an ability to ameliorate body weight disorder symptoms, at a sufficient concentration and for a time sufficient to elicit such an amelioration of body weight disorder symptoms in the exposed animals. The response of the animals to the exposure may be monitored by assessing the reversal of disorders associated with body weight disorders such as obesity. With regard to intervention, any treatments which reverse any aspect of body weight disorder-like symptoms should be considered as candidates for human body weight disorder therapeutic intervention. Dosages of test agents may be determined by deriving dose-response curves, as discussed in Section 5.5.1, below.

5.4.3. Compounds and Methods for the Treatment of Body Weight

Described below are methods and compositions whereby body weight including body weight disorders, including obesity, cachexia and anorexia may be treated. Because a loss of normal tub gene product function results in the development of an obese phenotype, an increase in tub gene product activity would facilitate progress towards a normal body weight state in individuals exhibiting a deficient level of tub gene expression and/or tub gene product activity.

Alternatively, symptoms of certain body weight disorders such as, for example, cachexia, which involve a lower than normal body weight phenotype, may be ameliorated by decreasing the level of tub gene expression and/or tub gene product activity. For example, tub gene sequences may be utilized in conjunction with well-known antisense, gene "knock-out," ribozyme and/or triple helix methods to decrease the level of tub gene expression. Such methods can also be useful for agricultural applications in which a more favorable fat level body mass ratio (i.e., a decreased ratio) is desired.

With respect to an increase in the level of normal tub gene expression and/or tub gene product activity, tub gene nucleic acid sequences, described, above, in Section 5.1, can, for example, be utilized for the treatment of body weight disorders, including obesity. Such treatment can be administered, for example, in the form of gene replacement therapy. Specifically, one or more copies of a normal tub gene or a portion of the tub gene that directs the production of a tub gene product exhibiting normal tub gene function, may be inserted into the appropriate cells within a patient, using vectors which include, but are not limited to adenovirus, adeno-associated virus, and retrovirus vectors, in addition to other particles that introduce DNA into cells, such as liposomes.

Because the tub gene is expressed in the brain, including the hypothalamus, such gene replacement therapy techniques should be capable delivering tub gene sequences to these cell types within patients. Thus, the techniques for delivery of tub gene sequences should be able to readily cross the blood-brain barrier, which are well known to those of skill in the art (see, e.g., PCT application, publication No. W089/10134, which is incorporated herein by reference in its entirety), or, alternatively, should involve direct administration of such tub gene sequences to the site of the cells in which the tub gene sequences are to be expressed. With respect to delivery which is capable of crossing the blood-brain barrier, viral vectors such as, for example, those described above, are preferable.

Additional methods which may be utilized to increase the overall level of tub gene expression and/or tub gene product activity include the introduction of appropriate tub-expressing cells, preferably autologous cells, into a patient at positions and in numbers which are sufficient to ameliorate the symptoms of body weight disorders, including obesity. Such cells may be either recombinant or non-recombinant.

Among the cells which can be administered to increase the overall level of tub gene expression in a patient are normal cells, preferably hypothalamus cells, which express the tub gene. Among the hypothalamic cells which can be administered are hypothalamic cell lines, which include, but are not limited to the GT1-1 cell line (Melcangi, R. C. et al., 1995, Endocrin. 136:679–686).

Alternatively, cells, preferably autologous cells, can be engineered to express tub gene sequences which may then be introduced into a patient in positions appropriate for the amelioration of body weight disorder symptoms. Alternately, cells which express the tub gene in a wild type in MHC matched individuals, i.e., non-tub individual, and may include, for example, hypothalamic cells. The expression of the tub gene sequences is controlled by the appropriate gene regulatory sequences to allow such expression in the necessary cell types. Such gene regulatory sequences are well known to the skilled artisan. Such cell-based gene therapy techniques are well known to those skilled in the art, see, e.g., Anderson, F., U.S. Pat. No. 5,399,349.

When the cells to be administered are non-autologous cells, they can be administered using well known techniques which prevent a host immune response against the introduced cells from developing. For example, the cells may be introduced in an encapsulated form which, while allowing for an exchange of components with the immediate extracellular environment, does not allow the introduced cells to be recognized by the host immune system.

Additionally, compounds, such as those identified via techniques such as those described, above, in Section 5.4.2, which are capable of modulating tub gene product activity can be administered using standard techniques which are well known to those of skill in the art. In instances in which the compounds to be administered are to involve an interaction with brain cell types such as, for example, hypothalamic cell types, the administration techniques should include well known ones which allow for a crossing of the blood-brain barrier.

5.5. Pharmaceutical Preparations and Methods of Administration

The compounds that are determined to affect tub gene expression or gene product activity can be administered to a patient at therapeutically effective doses to treat or ameliorate weight disorders, including obesity. A therapeutically effective dose refers to that amount of the compound sufficient to result in amelioration of symptoms of body weight disorders.

5.5.1. Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

5.5.2. Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa utter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

EXAMPLE: GENETIC MAPPING OF THE tub LOCUS

In the Example presented herein, studies are described which, first, define the genetic interval within which the tub gene lies, and, second, successfully narrow the interval to approximately 0.25 cM.

6.1. Materials and Methods

The tubby Phenotype. The tubby phenotype was assessed by weighing the mice. Females weighing less than 35 grams at 150 days were classified as normal (i.e., either +/+ or tub/+), while those weighing greater than 43 grams were typed as tub/tub. Males weighing more than 55 grams at 150 days were classified as tub/tub, while males weighing less than 55 grams were classified as unknown.

The markers used to genotype the crosses were those identified and mapped at the Whitehead Institute at the Massachusetts Institute of Technology (Dietrich et al., 1992, Genetics 131:423–447).

The European backcross mapping panel (Breen et al., 1994, Human Mol. Genet. 3:621–627), which consists of a C57BL/6J x *Mus Spretus* backcross, was used to order markers within the tub gene interval.

Hbb protein polymorphism typing is described in Whitney, J. B. III, 1978, Biochem. Genet. 16:667–672.

Mouse crosses were performed according to standard procedures.

6.2. Results

The murine tub gene had previously been mapped to 2.4 cM +/−1.4 cM distal of the hemoglobin beta locus (Hbb) on mouse chromosome 7 (Jones, J. M. et al., 1992, Genomics 14:197–199). 2.4 cM represents a genetic distance measurement corresponding to 3 observed genetic crossovers in 125 opportunities. On average, in the mouse genome, this is equivalent to a physical distance of approximately 4.8 million base pairs. This level of genetic resolution, however, was not satisfactory for the cloning of the tub gene. Further, the region of chromosome 7 containing the tub gene was not well defined, and no defined markers existed which flanked the tub locus.

Described herein, therefore, are genetic crosses which: 1) define the chromosomal region surrounding the tub gene, and 2) narrow the interval within which the tub gene is determined to lie to 0.25 cM.

Specifically, two large crosses segregating the tubby phenotype were set up and performed, and were typed with available genetic markers known to map within the relevant region of chromosome 7.

First, an intercross of [C57BL/6J-tub x DBA/2J] $F_1$ hybrid mice was set up. These hybrid mice were the progeny derived from the mating of two inbred stains, C57BL/6J-tub/tub and DBA/2J-+/+. In total, 417 $F_2$ progeny, representing 838 independent meioses, were analyzed. Typing all informative markers against this cross identified a genomic region of approximately 4 megabases between the markers D7Mit17 and D7Mit281 which contained the tub gene. Two $F_2$ progeny showed recombination events between D7Mit17 and the tub locus, thereby establishing this marker as proximal to the tub locus. Five recombinant $F_2$ progeny demonstrated that the tub locus lies proximal to the D7Mit281 marker, thus placing the tub locus between the D7Mit17 and D7Mit281 markers, as shown in FIG. 1. The distance between the markers D7Mit17 and D7Mit281 was determined to be about 2.0 cM, thereby narrowing the interval within which the tub gene must lie to this 2.0 cM region.

The tub genetic interval was further narrowed by exploiting a by product of the way in which tub stock is maintained. tub heterozygotes must be identified in order to easily maintain the stock because tub homozygotes have reduced fertility. In order to maintain such heterozygotes, a C57BL/6J-tub strain was crossed with the congenic C57BL/6J-Hbb$^P$ strain. This congenic strain is presumed to be genetically identical to the C57BL/6J strain except for a genomic segment from a wild mouse strain surrounding and including the Hbb locus. As a result, the C57BL/6J-Hbb$^P$ strain has an Hbb allele (Hbb$^P$) which can be distinguished electrophoretically from the C57BL/6J Hbb allele (Hbb$^S$). Because the Hbb locus is closely linked to the tub locus, those animals found to be Hbb$^P$/Hbb$^S$ were presumed to be heterozygous at the tub locus as well (a subset of animals were tested for the tubby phenotype later, to assure that no recombination between the Hbb and tub loci had taken place).

Because the two markers under selection for heterozygosity in such a maintenance scheme are Hbb and tub, the genomic region between these two loci also remains heterozygous as the stock is propagated. However, with each successive generation, this region will narrow, and the region outside this interval will become homozygous for C57BL/6J alleles.

By genotyping of the parental strains C57BL/6J and C57BL/6J-Hbb$^P$, the boundaries of the original congenic interval surrounding the Hbb locus were established. Proximal of the tub locus, the congenic interval includes the markers D7Mit17, 39, 33, 37 and 38. The congenic interval extends distally beyond the marker D7Mit222 and includes the markers D7Mit130 and 53.

The genotyping of the C57BL/6J-tub/+-Hbb$^S$/Hbb$^P$ strains generated herein, led to the finding that the markers D7Mit39, 53 and 22 were homozygous for C57BL/6J alleles in each of the animals of this strain which were tested. This showed that the congenic interval had been narrowed, through subsequent generations, to an interval between D7Mit39 and D7Mit53 (D7Mit39 is 0.3 cM proximal to D7Mit17). Because the tub locus is, by necessity, heterozygous in these animals, it must also, therefore, lie within this D7Mit39-to-D7Mit53 interval. Based on the typing of 982 progeny of the European backcross mapping panel (Breen et al., 1994, Human Mol. Genet. 3:621–627), this interval was estimated to be approximately 0.5 cM.

Next, the tub maintenance stock was used as a cross. Because heterozygous mice of this stock (C57BL/6J-tub/+) were heterozygous for markers within the congenic interval, such a cross represented an $F_1$ intercross segregating tubby in a manner analogous to the tub/DBA/2J intercross. 394 meioses were genotyped and a single recombinant mouse was identified, demonstrating that the tub locus lies proximal to the D7Mit130 marker. Thus, at this point in the genetic mapping, the proximal boundary of the tub interval was D7Mit17, as defined by the recombinants isolated from the [C57BL/6J-tub x DBA/2J] $F_1$ intercross and the distal boundary of the tub interval was D7Mit130, as shown by the recombinant of this C57BL/6J-tub/+ intercross. The total number of meioses genotyped at this point was 1232: 838 meioses in the [C57BL/6J-tubxDBA/2J] $F_1$ intercross and 394 meioses in the maintenance stock intercross.

The size of this region was estimated to be approximately 0.25 cM on the European backcross panel. On average in the mouse genome, such a genetic distance corresponds to a physical distance of approximately 500 kb. This finding led to efforts to clone the intervening DNA in an attempt to isolate the tub gene.

7. EXAMPLE

PHYSICAL MAPPING OF THE tub GENE INTERVAL

As a step toward identifying the tub gene, the Example presented herein describes the physical mapping of the D7Mit17 to D7Mit53 interval within which the tub gene was determined to lie.

7.1. MATERIALS AND METHODS

Yeast artificial chromosome (YAC) libraries. Two mouse genomic YAC libraries were screened in an effort to identify specific YACs containing genomic DNA from the tub region. The first YAC library, the Whitehead Mouse YAC Library I, was obtained from Research Genetics (Huntsville, Ala.). The second YAC library, the St. Mary's/ICRF YAC library, was a composite library made of YACs constructed at St. Mary's Hospital (London, England) and of YACs constructed at the Imperial Cancer Research Fund laboratories and it was obtained from St. Mary's Hospital.

The YAC libraries were screened by PCR amplification of DNA pools representing the libraries. A description of a screening protocol can be found in Research Genetics Catalog No. 95020.

The terminal sequences of the YACs were isolated by vectorette PCR according to Riley et al., 1990, Nucl. Acids Res. 18:2887–2890). Sequencing was performed according to standard procedures.

YAC ends were mapped according to the protocol described by Tuffrey et al., 1993, Hum. Mut. 2:368–374 for single-stranded conformational polymorphism (SSCP) analysis, using SSCPs identified between C57BL/6J and Mus spretus (the two mouse strains used to generate the European Backcross mapping panel). Utilizing the YAC end SSCPs it was possible to determine that the ends of the YACs mapped between the D7Mit17 and D7Mit53 markers.

P1 bacteriophage. A mouse genomic P1 bacteriophage library (Pierce, J. C. et al., 1992, Mamm. Genome 3:550–558) as screened using the Genome Systems screening service. For screening, the ura end of the M72 YAC (M72R) was identified via vectorette PCR (Riley et al., 1990, Nucl. Acids Res. 18:2887–2890). M72R was sequenced and two PCR fragments were chosen from this sequence, as shown below:

M72R-f: (SEQ ID NO:40) 5'-TGC GCA GAA ACA ATC ACC TA-3'; and
M72R-r: (SEQ ID NO:41) 5'-CAA GAC GTG AAC CTG GA-3'

The two primers amplify a 129 bp fragment from mouse genomic DNA. The primers were used by Genome Systems screening service to screen the mouse genomic Pi library.

Bacterial Artificial Chromosomes (BACs). A MIT/Research mouse BAC library obtained from Research Genetics (Catalog No. 96023) was screened according to manufacturer's suggested screening protocol.

7.2 RESULTS

Described herein are results which describe the physical mapping of the tub region. This region is shown in FIG. 1. In FIG. 1, genetic markers are indicated above the top line, while YACs spanning the region are shown below this. The checkered P1 and BAC clones were analyzed by sequence sampling and exon trapping (see Section 8, below). Overlaps between clones were identified by PCR amplification of clones with physical markers in the region. The tub gene, as described, below, in this section, was mapped between D7Mit17 and D7Mit53.

The markers D7Mit 127, 219, 63, 280, 236 and 130 were mapped between the D7Mit17 and D7Mit53 markers on the European Backcross panel (Breen et al., 1994, Human Mol. Genet. 3:621–627). These markers, including the D7Mit17 and D7Mit53 markers, were used, therefore, to screen the MIT YAC library.

Screening with these markers resulted in the identification of a set of YACs which constituted two contigs. Specifically, the contig around D7Mit17 included YACs M65, M70 and M72, while the contig around D7Mit53 included M49, M79 and M31.

In order to clone the gap between the two YAC contigs, physical PCR markers at the ends of the YACs were established, via vectorette PCR (Riley, 1990, Nucl. Acids Res. 18:2887–2890), with which to rescreen the YAC library. The resulting PCR products were sequenced and PCR screening primers were chosen. The trp ends of YACs M70 and M31 were isolated (trp ends will be referred to herein as the left end of the YACs, e.c., M70L, while the ura ends will be referred to herein as the right ends), and were genetically mapped, as described, above, in Section 6.1, to the tub region of mouse chromosome 7 in order to show that they were not derived from chimeric YACs. These ends were then used to screen the St. Mary's/ICRF YAC library.

One YAC, M84, was identified by both M70L and M31L. Thus, a single contig spanning the D7Mit17 to D7Mit53 was established. The minimal contig consisted of M65, M72, M84, M31, M79 and M49, as shown in FIG. 1.

In order to further aid in gene identification and to confirm the integrity of the YAC contig described above, P1 bacteriophage and bacterial artificial chromosomes (BACs) were established for the interval between D7Mit17 and D7Mit130. These P1 clones and BACs overlap to form three contigs separated by two gaps, as shown in FIG. 1.

8. EXAMPLE: IDENTIFICATION OF A CANDIDATE tub GENE

In the Example presented herein, a gene is identified, via exon trapping and sequence sampling, within the cloned DNA described in the Example presented, above, in Section 7, which corresponds to a candidate tub gene. Specifically, Section 8.1 describes the exon trapping and sequencing analyses, while Section 8.2 describes the cloning of putative tub gene cDNA clones.

8.1. EXON TRAPPING AND SEQUENCE SAMPLING OF tub GENE INTERVAL DNA

MATERIALS AND METHODS

Eleven P1 (P1, P2, P3, P4, P6, P7, P8, P10, P11, P13 and P14) and twelve BAC (B1, B2, B3, B4, B5, B6, B7, B9, B12, B13, B14 AND B15) clones were subcloned into the D-pSPL3, vector, exon trapped and sequence sampled, as described below.

Exon trapping. The exon trapping analysis was performed using Gibco BRL Exon Trapping System (Cat. No. 18449-017) and using the D-pSPL3 vector, a modified version of the pSPL3 vector (Gibco BRL Life Sciences). In this system, exons are trapped from genomic DNA subcloned into the vector as a result of the interaction between the vector splice site and splice sites flanking exons in the genomic DNA.

D-pSPL3 was derived from the splicing vector pSPL3 (Gibco BRL Life Sciences) by deletion of the NdeI (1119) -NheI (1976) fragment in the HIV tat intron to eliminate the cryptic splice-donor site at position 1134 in the pSPL3 sequence. Stocks of BamHI-cut and PstI-cut D-pSPL3 DNA were prepared by digesting 50–100 µg DNA with the corresponding enzyme and dephosphorylating the linearized vector with calf intestinal alkaline phosphatase as specified by the manufacturers (New England Biolabs and Boerhinger Mannheim, respectively). The linearized vector was purified away from uncut plasmid DNA by agarose gel electrophoresis and electroelution and assayed to assess the level of uncut and self-ligated vector as described elsewhere (Pulido and Duyk, 1994, in Current Protocols in Human Genetics, Wiley Pub., pp 2.2.1–2.3.1).

Briefly, P1 and BAC clone DNA was prepared from overnight cultures (100 ml LB/kanamycin 25 µg/ml) by standard alkaline lysis, treated with RNase A, purified by phenol/chloroform/isoamyl alcohol (25:24:1) extraction, ethanol precipitated, rinsed in 70% ethanol, dried and resuspended in 400 µl deionized water.

5–10 µg P1/BAC DNA was cut with either BamHI and BglII, or PstI, as specified by the manufacturer (New England Biolabs, Beverly, Mass.). The digested DNA was phenol extracted, ethanol precipitated and resuspended in 50 µl deionized water.

Exon trapping was then completed as described in the Gibco BRL Exon Trapping Manual. Briefly, the D-pSPL3 clones were transfected into COS-7 cells. RNA was isolated and first strand cDNA was synthesized. Two rounds of nested PCR specifically amplified transcripts derived from the D-pSPL3 clones. These PCR products were cloned into the vector pAMP10. Clones from this pAMP10 library of trapped fragments were then analyzed by PCR to determine insert sizes. Clones with insert sizes greater than 150 bp were sequenced using M13 forward and reverse primers. One of the D-pSPL3 subclones was designated ium008p004, and was sequenced.

A 90 bp fragment, designated P8X1, was PCR amplified using the sequence of this subclone insert. The P8X1 fragment was generated using two PCR primers which were designed using the ium008p004 sequence as follows:

P8X1F1(SEQ ID NO: 42):   5'-GCG GAT ACA GAC TCT CTC AT-3'
P8X1R1(SEQ ID NO: 43):   5'-GAG GAC AAA TGT CCT AGG CT-3'

The 90 bp P8X1 DNA fragment was PCR amplified from first strand cDNA made from C57BL/6J mouse brain RNA. Standard cDNA synthesis and PCR procedures were utilized.

Sequence sampling. Sequence sampling is a technique for rapidly determining whether coding sequences were present in a nucleic acid sample of interest (See Claverie, J. M., 1994, Genomics 23:575–581). The inserts in D-pSPL3 clones described above were sequenced in both orientations using the following primers:

SPL3A(SEQ ID NO: 44):  5'-CAT GCT CCT TGG GAT GT-3'
SPL3C(SEQ ID NO: 45):  5'-TGA GGA TTG CTT AAA GA-3'

After vector trimming and quality assessment, the resulting sequences were compared to nucleic acid and protein databases using BLAST algorithms (Altschul, S. F. et al., 1990, J. Mol. Biol. 215:403–410).

RESULTS

In order to look for genes within the cloned DNA, described, above, in Section 7, within the interval containing the tub gene, P1 and BAC clones were subcloned into the D-pSPL3 vector and exon trapped and sample sequenced, as described, above, in the Materials and Methods portion of this section. One of the D-pSPL3 subclones, designated ium008p004, was derived from a D-pSPL3 library made from the P8 clone (see FIG. 1). A 327 base pair portion of the P1 insert in ium008p004 was sequenced. The protein sequence encoded by this portion of ium008p004 showed homology to two translated sequences in the GenBank nucleic acid database. Two primers were selected from the region of homology and used to amplify a DNA fragment of 90 bp, called P8X1, having the following sequence:

2×SSC/0.1 SDS at 65° C. was attained and autoradiography was performed overnight. One million clones were screened. Among the clones identified was the fume009 clone, a 1.15 kb cDNA, which was then sequenced.

The fume009 clone was used to screen a mouse hypothalamus cDNA library. This library was constructed from poly-A$^+$ RNA from 6 week old C57BL/6J mice. First and second strand cDNA was made from the poly-A$^+$ RNA using standard procedures. cDNA was ligated into Uni-ZAP XR lambda vector and packaged using a Stratagene kit (Cat. No. 237611). Identical washing conditions as described above were utilized. The screen identified a 6.0 kb clone, designated fumh019, which was sequenced. The fumh019 cDNA clone contains the entire CBT9 gene coding region. The CBT9 sequence is further discussed, below, in the Example presented in Section 12.

RESULTS

In order to isolate CBT9 cDNA clone, the P8X1 fragment was used, as described, above, in the Materials and Methods portion of this section, to screen a mouse brain cDNA library. This screen resulted in the isolation of the fume009 1.15 kb cDNA clone.

The fume009 cDNA clone was then used, as described, above, in the Materials and Methods portion of this section, to screen a mouse hypothalamus cDNA library. This screen resulted in the isolation of a 6.0 kb cDNA clone, designated fumh019.

The fumh019 cDNA clone was sequenced and was determined to contain the entire CBT9 coding region. The CBT9

```
5'GAGACAAATG TCCTAGGCTT CAAGGGACCT CGGAAGATGA GTGTGATCGT
   CCCAGGCATG AACATGGTTC ATGAGAGAGT CTGTATCCGC 3'
```

The ium008p004 homologies were to Genbank sequences Z48334 and X69827. Z48334 is the partial sequence of a *Caenorhabditis elegans* cosmid, F10B5. One of the putative genes identified within this sequence contains a 425 amino acid open reading frame, designated F10B5.4 (Wilson R. et al, 1994, Nature 368:32–38). X69827 is a mouse 981 bp partial cDNA with a potential open reading frame of 323 amino acids. This sequence has been shown to have similarity to the family of phosphodiesterase proteins (Vambutas, V. and Wolgemuth, D. J., 1994, Biochim. Biophys. Acta. 1217:203–206).

The above sequence was flanked by consensus splice sites, further demonstrating that the sequence is from an exon, or a coding region, of a gene. The homology to a known gene, as described above, coupled with the presence of consensus splice sites strongly suggested that this region of the ium008p004 clone corresponded to a portion of the coding region of a gene. Given its location within the interval in which the tub gene is located, this putative gene, which was designated CBT9, represented a tub gene candidate.

8.2 ISOLATION OF CBT9 cDNA CLONES

MATERIALS AND METHODS cDNA cloning. In order to isolate a longer cDNA of the CBT9 gene, the P8X1 fragment was used as a probe to screen a Stratagene (La Jolla, Calif.) mouse brain cDNA library (#936309). For hybridization, Amersham Rapid Hyb Buffer (Cat. No. RPN1639) was utilized according to manufacturer's protocol. A final washing stringency of was nucleotide and amino acid sequence are described, below, in the Example presented, below, in Section 12.

9. EXAMPLE: CHARACTERIZATION OF THE EXPRESSION OF THE CBT9 GENE

In the Example presented herein, Northern analysis data is described which characterizes the CBT9 gene (see Section 8, above). Specifically, experiments are presented herein which evaluate the expression of CBT9 in a number of mouse tissues obtained from wild type and tub mice. The results presented herein are consistent with the CBT9 gene being the tub gene.

9.1 MATERIALS AND METHODS

Northern analysis. The P8X1 DNA fragment and the fume009 cDNA clone were used to probe Northern blots containing total mouse RNA.

Total RNA from tub and wild type (C57BL/6J) mice was isolated and utilized for the Northern analysis. All mice were sacrificed by carbon dioxide asphyxiation. Tissues were dissected on ice, snap-frozen in liquid nitrogen and stored at −80° C. Total RNA was isolated using RNazolB (TelTest, Inc.) The total RNA samples were resuspended in RNase-free DEPC-treated water and quantitated by optical density measurement.

For the Northern blots, 10µg total RNA of each sample was loaded onto a formaldehyde gel. The gel was blotted onto a nylon membrane using standard Northern transfer techniques. The blot was hybridized with P8X1 which had been radiolabelled by random priming using a Gibco-BRL kit (Cat. No. 18187-013) according the manufacturer's recommended protocol. For hybridization, Amersham Rapid Hyb Buffer (Cat. No. RPN1639) was utilized according to manufacturer's protocol. A final washing stringency of 0.1× SSC/0.1% SDS at 65° C. was attained, and autoradiography was performed overnight.

The Northern blot depicted in FIG. 2 was loaded as follows: lane 1, wild type brain without hypothalamus; lane 2, tub brain without hypothalamus; lane 3, wild type hypothalamus; lane 4, tub hypothalamus; lane 5, wild type heart; lane 6, tub heart; lane 7, wild type lung; lane 8, tub lung; lane 9, wild type liver; lane 10, tub liver; lane 11, wild type kidney; lane 12, tub kidney; lane 13, wild type spleen; lane 14, tub spleen; lane 15, wild type stomach; lane 16, tub stomach; lane 17, wild type muscle; lane 18, tub muscle; lane 19, wild type fat; lane 20, tub fat; lane 21, wild type testis; lane 22, tub testis; lane 23, RNA molecular weight standards, the sizes of which are indicated by the lines at the right hand side of the blot. Specifically, the sizes are 9.49 kb, 7.46 kb, 4.40 kb, 2.37 kb, 1.35 kb and 0.24 kb. The crosses indicate the positions of the 28S and 18S ribosomal RNA molecules. "Wild type" refers to C57BL/6J mice.

Figure 3:
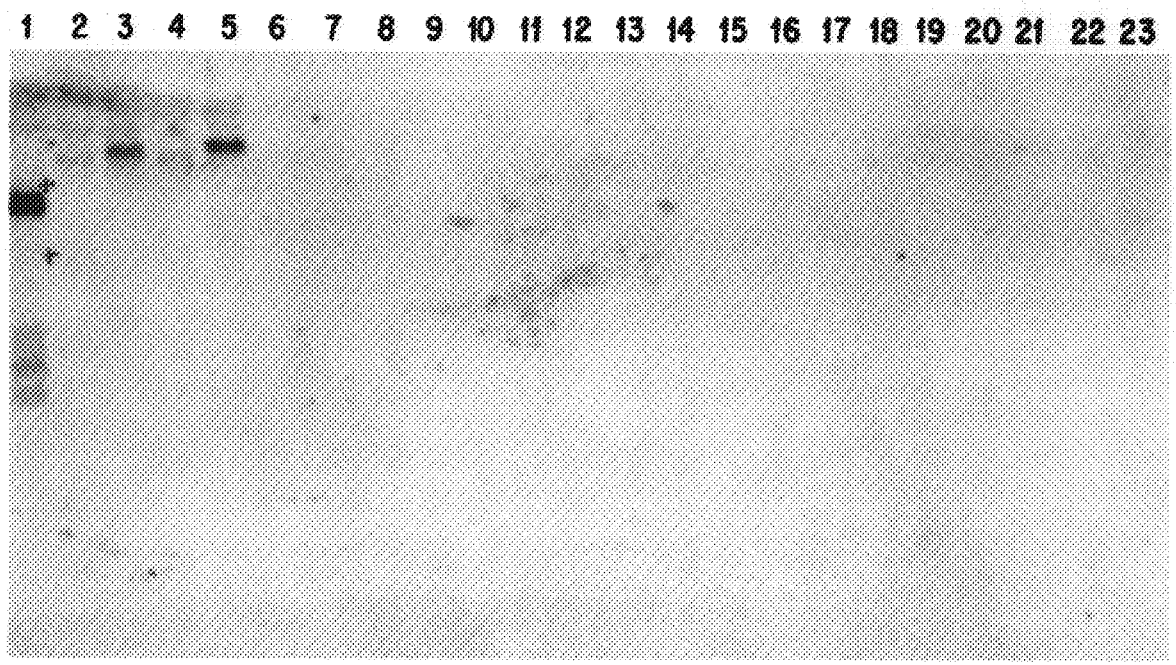
FIG. 3. Northern blot analysis of total RNA derived from various tissues of tub and wild type (C57BL/6J) mice, using the 1.15 kb fume009 cDNA clone as a probe. See Sections 9.1 and 9.2 for details.
Figure 4:
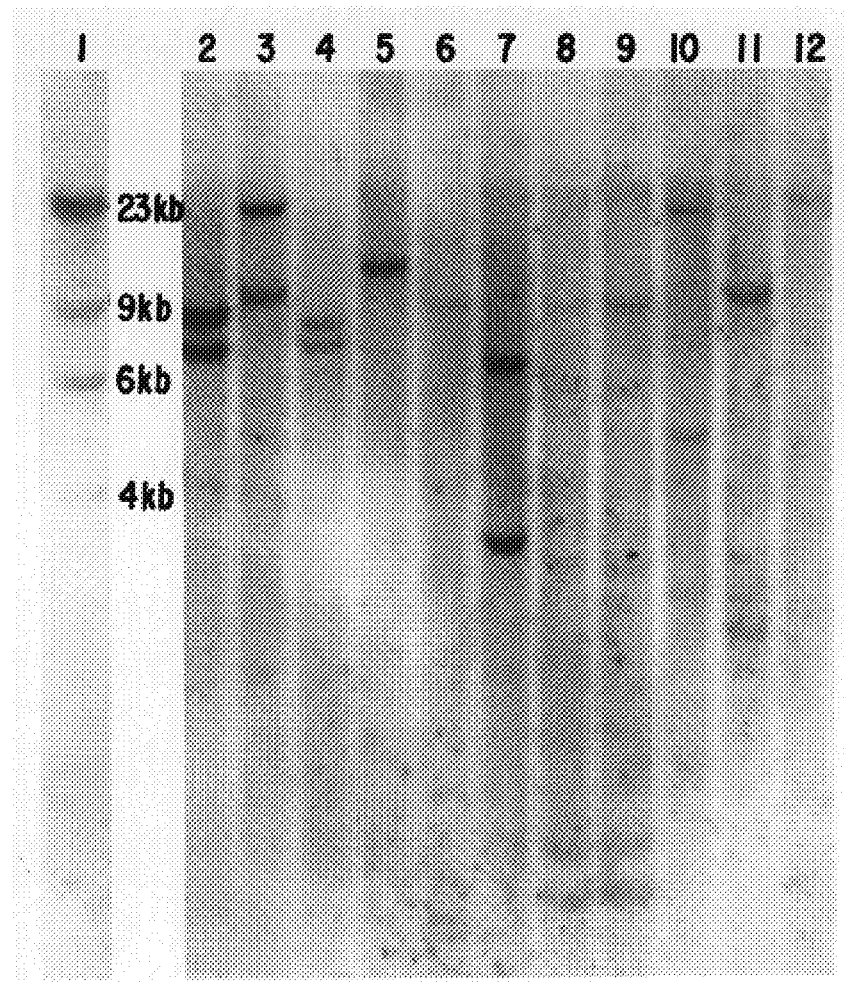
FIG. 4. Southern blot analysis of EcoRI-digested mammalian genomic DNA derived from a number of different species, as indicated, using a fragment of CBT9 (P8X9-10) as a probe, as described, below, in Sections 10.1 and 10.2.

The Northern blot depicted in FIG. 3 was loaded as follows: lane 1, RNA molecular weight standards, the sizes of which are indicated by the lines at the side of the blot (specifically, such sizes are 9.49 kb, 7.46 kb, 4.40 kb, 2.37 kb, 1.35 kb and 0.24 kb); lane 2, wild type brain without hypothalamus; lane 3, tub brain without hypothalamus; lane 4, wild type hypothalamus; lane 5, tub hypothalamus; lane 6, wild type heart; lane 7, tub heart; lane 8, wild type lung; lane 9, tub lung; lane 10, wild type liver; lane 11, tub liver; lane 12, wild type kidney; lane 13, tub kidney; lane 14, wild type spleen; lane 15, tub spleen; lane 16, wild type stomach; lane 17, tub stomach; lane 18, wild type muscle; lane 19, tub muscle; lane 20, wild type fat; lane 21, tub fat; lane 22, wild type testis; lane 23, tub testis. The crosses indicate the positions of the 28S and 18S ribosomal RNA molecules. "Wild type" refers to C57BL/6J mice.

9.2. RESULTS

Figure 2:
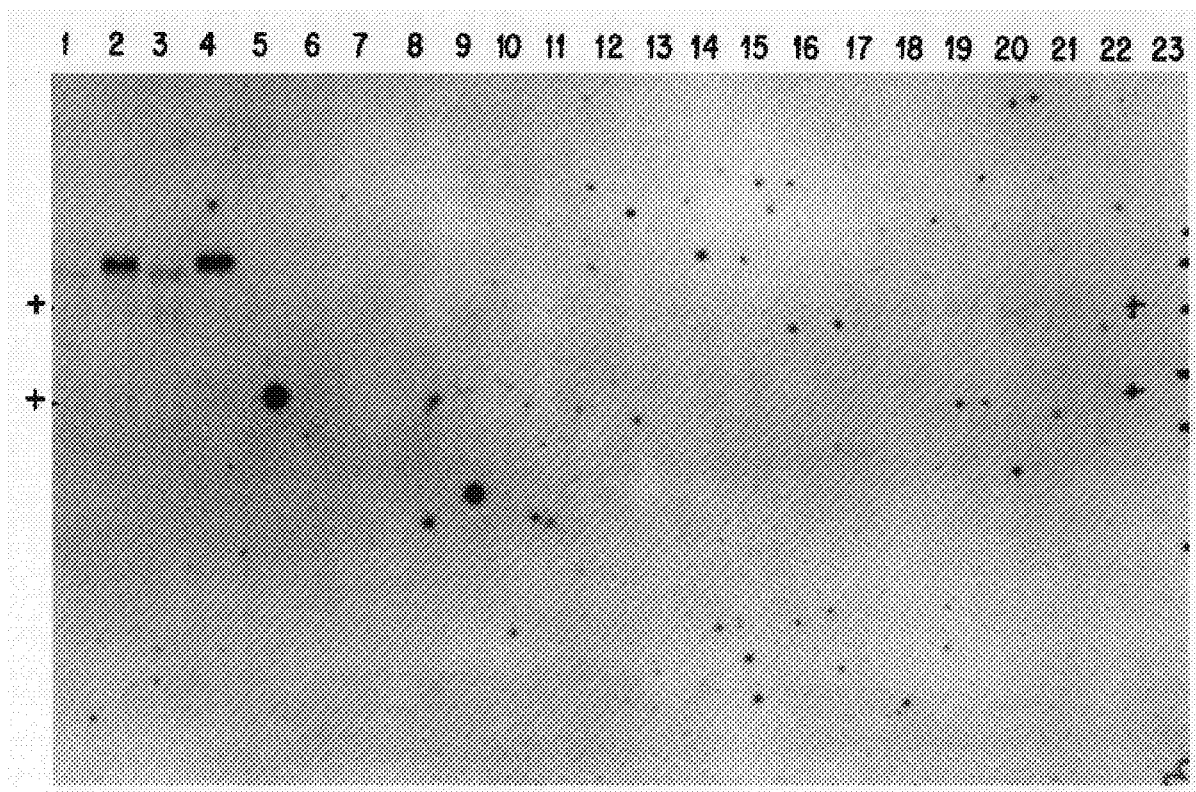
FIG. 2. Northern blot analysis of total RNA derived from various tissues of tub and wild type (C57BL/6J) mice, using the 90 bp P8X1 DNA fragment as a probe. See Sections 10.1 and 10.2 for details.

As shown in FIG. 2, a CBT9 transcript of approximately 7.0 kb is present in the hypothalamus without brain (lane 2) and in the hypothalamus (lane 4) RNA samples derived from the wild type C57BL/6J mice as detected by the P8X1 probe. No CBT9 transcript is detectable in other total RNA samples derived from wild type mouse tissues.

As is further shown in FIG. 2, a CBT9 transcript of approximately 7.5 kb, i.e., approximately 0.5 kb larger than the transcript seen in the wild type tissues, is present in both the brain without hypothalamus (lane 3) and hypothalamus (lane 5) RNA samples derived from the tub mice as detected by the P8X1 probe. No CBT9 transcript is detectable in other samples of total RNA derived from tub mouse tissues. It should additionally be noted that the abundance of the transcript detected by the P8X1 probe in tub RNA samples is approximately 5-fold greater than it is in RNA samples from wild type (C57BL/6J) mice.

In addition, the fume009 clone was used as a probe to verify the results, described above, which were obtained using the P8X1 fragment as a probe. As shown in FIG. 3, Northern analysis using such a fume009 sequence to probe total RNA from tub and wild type mouse tissue samples yielded the same CBT9 results which were observed using the P8X1 probe. Specifically, a transcript of the same increased size was seen in the total RNA samples derived from tub homozygous mice and the same up regulation was observed in the amount of tub RNA present in total RNA samples derived from tub homozygous animals relative to wild type animals.

A Northern blot analysis of total RNA derived from an animal genotypically shown to be heterozygous for the tub mutation revealed, as expected from the above results, the presence of both the 7.5 kb and 7.0 kb transcripts in total brain RNA. In addition, a moderate up regulation (approximately two-fold) of CBT9 transcript levels relative to CBT9 levels in wild type animals, was observed.

The results of these Northern analyses strongly suggest that a defect within the CBT9 gene results in the tubby phenotype. Specifically, the difference in size observed between the CBT9 transcript in wild type and in tub RNA is consistent with a mutation resulting in the inclusion of exogenous nucleic acid into the tub mRNA. Second, the approximately 5-fold up regulation of CBT9 RNA levels in the RNA samples derived from the tub/tub homozygotes relative to levels observed in RNA samples derived from the wild type mice suggests that such high levels of this transcript are related to the obesity phenotype seen in tubby animals. This may be the result of a negative feedback loop induced by the absence or malfunction of the protein encoded by the mutant tub (CBT9) gene. Third, in total mouse RNA, the CBT9 gene is expressed in the brain, including the hypothalamus, a region of the brain which is known to be involved in the control of body weight (Bray, G. A., 1992, Progress in Brain Res. 93:333–341). Finally, the moderate up regulation seen in the heterozygous animals is consistent with the recessive inheritance pattern of the tubby phenotype, in which heterozygotes are not obese, but, nonetheless, have been shown to exhibit some phenotypic differences relative to homozygous wild type control animals (Nishina, P. M. et al., 1994, Metabolism 43:554–558).

10. EXAMPLE: CBT9 SOUTHERN BLOT ANALYSIS

In the Example presented herein, the results of a Southern blot analysis are described which indicate that homologs of the murine CBT9 gene are present and have been conserved in other mammalian species.

10.1. MATERIAL AND METHODS

Southern blot analysis. Two PCR primers were designed from the CBT9 nucleotide coding sequence, as follows:

P8X9F1(SEQ ID NO: 47): 5'-GGA CAA GAA GGG GAT GGA C-3'
P8X10R1(SEQ ID NO: 48): 5'-CCG TGG ATG ATC TGG AAG T-3'

The primers were used to amplify, via RT-PCR, a 650 bp cDNA fragment (designated P8X9-10) from C57BL/6J mouse whole brain RNA. Standard RT-PCR conditions were utilized. The band was gel-purified and random-prime radiolabelled, as described above.

The resulting probe was hybridized to a Southern blot of EcoRI-digested genomic DNA (BIOS Laboratories; #EBM-100E) from various mammals. Each lane was loaded with 8 µg of digested genomic DNA. For hybridization, Amersham Rapid Hyb Buffer (Cat. No. RPN1639) was utilized according to manufacturer's protocol. A final washing stringency of 0.5×SSC/0.1% SDS at 65° C. was attained, and blots were exposed overnight with an intensifying screen at −80° C.

Figure 5:
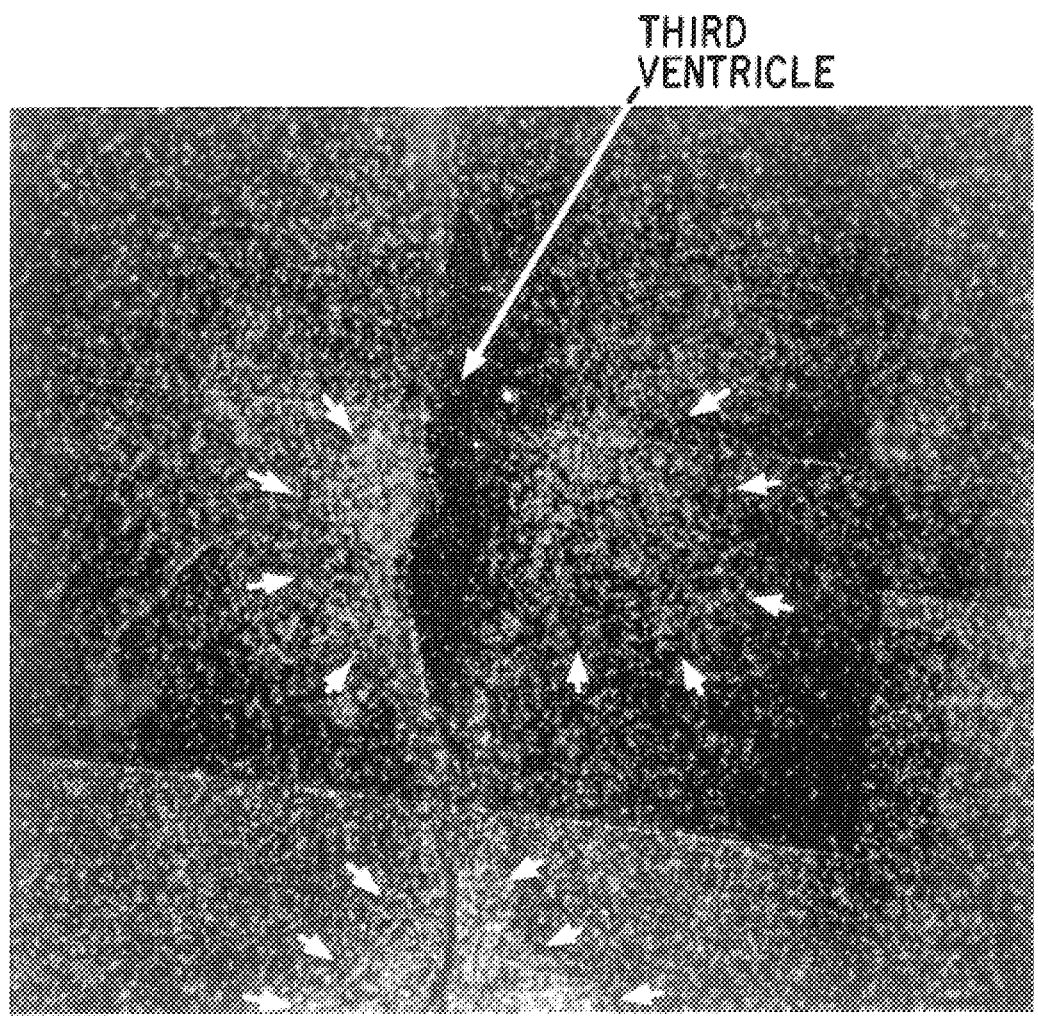
FIG. 5. In situ hybridization analysis of CBT9 spatial expression in a brain (hypothalamus) tissue section of C57BL/6J wild type mice, using a fume009 cDNA probe.

The lanes of the Southern blot depicted in FIG. 5 were loaded as follows: lane 1, markers: lambda DNA digested with HindIII (band sizes are as indicated in the figure); lane 2, mouse; lane 3, hamster; lane 4, rat; lane 5, rabbit; lane 6, dog; lane 7, cat; lane 8, cow; lane 9, sheep; lane 10, pig; lane 11, marmoset; lane 12, human.

10.2 RESULTS

A Southern blot analysis was conducted using a CBT9 probe (P8X9-10; see Section 10.1 for details) and a DNA blot containing EcoRI-digested mammalian genomic DNA of various species, as described above, in Section 10.1. As is shown in FIG. 5, the CBT9 probe detects homologous sequences in each of the mammalian DNA sample represented on the blot. This result provides additional evidence that the CBT9 sequence used as a probe is part of a gene and, additionally, demonstrates that the sequences show a high level of conservation among a wide range of mammalian species.

11. EXAMPLE: CBT9 IN SITU HYBRIDIZATION ANALYSIS

In the Example presented herein, the results of an in situ hybridization analysis are described which verify that the CBT9 gene is expressed in the brain. Primary CBT9 gene expression occurred within the hippocampus, hypothalamus and cortex. Weaker hybridization could be seen throughout the brain.

11.1 MATERIALS AND METHODS

In situ Hybridization Localization: Brains from 6 month-old C57 BL/6J mice were removed flash frozen at −80° C. and stored at −80° C. until use. 10 μm frozen sections of brains were post-fixed with 4% PFA/PBS for 15 minutes. After washing with PBS, sections were digested with 1 μg/ml proteinase K at 37° C. for 15 minutes, and again incubated with 4% PFA/PBS for 10 minutes. Sections were then washed with PBS, incubated with 0.2N HCl for 10 minutes, washed with PBS, incubated with 0.25% acetic anhydride/1M triethanolamine for 10 minutes, washed with PBS and dehydrated with 70% ethanol and 100% ethanol. Hybridizations were performed with $^{35}$S-radiolabelled ($5 \times 10^7$ cpm/ml) cRNA probes encoding a 1.15 kb segment of the coding region of the mouse clone fume009 in the presence of 50% formamide, 10% dextran sulfate, 1× Denhardt's solution, 600 mM NaCl, 10 mM DTT, 0.25% SDS and 100 μg/ml tRNA for 18 hours at 55° C. After hybridization, slides were washed with 5×SSC at 55° C., 50% formamide/2×SSC at 55° C. for 30 minutes, 10 mM Tris-HCl (pH 7.6)/500 mM NaCl/1 mM EDTA (TNE) at 37° C. for 10 minutes, incubated in 10 μg/ml RNase A in TNE at 37° C. for 30 minutes, washed in TNE at 37° C. for 10 minutes, incubated once in 2×SSC at 50° C. for 30 minutes, twice in 0.2×SSC at 50° C. for 30 minutes, and dehydrated with 70% ethanol and 100% ethanol. Localization of mRNA transcripts was detected by film emulsion autoradiography followed by dipping slides in photo-emulsion for precise autoradiographic localization.

11.2 RESULTS

The fume009 cDNA clone was used as a probe for an in situ hybridization analysis. Specifically, the 1.15 kb fume009 probe was hybridized to sections of wild type C57BL/6J mice. As shown in FIG. 5, the CBT9 transcript is expressed in the hypothalamus and other regions of the brain, consistent with the above-described Northern analysis data, which was presented in Section 9, above.

Specifically, an mRNA transcript hybridizing to the 1.15 kB fume009 antisense cRNA probe was localized to discrete regions of the brain of both C57BL/6J wild-type mice (FIG. 5) and tub homozygous mice. Signal was observed in the hypothalamus adjacent to the 3rd ventricle in two "nuclear bodies" (indicated by dense clustering of nuclei) as well as at the base of the hypothalamus adjacent to the optic chiasm in the tissue from both mice. Thus, expression in the hypothalamus is highest in the paraventricular, ventromedial and arcuate nuclei.

In addition, signal was detected in scattered cells in the subcortical temporal lobe and in hippocampus in the tissue sections from both mice. FIG. 5 shows the regions of localization of tub gene transcript in the brain of C57BL/6J mice (the arrows indicate those regions where signal was detected). Weaker hybridization was observed throughout the brain. No distinct signal was observed in heart, spleen, liver, lung, skeletal muscle, pancreas, small intestine and stomach of either the C57 BL/6J wild-type mice or tub homozygous mice.

12. EXAMPLE: IDENTIFICATION OF CBT9 AS THE tub GENE

Presented in this Example is, first, a mutational analysis of the CBT9 gene, which compares CBT9 gene sequences within nucleic acid derived from wild type and tub animals. Specifically, a CBT9 splice site mutation is identified within tub genomic DNA which is absent from wild type genomic DNA. Second, the nucleotide and derived amino acid sequence of the CBT9 gene is presented. The results disclosed herein, coupled with the results presented, above, in Sections 6 to 11, identify the CBT9 gene to be the tub gene.

12.1 MATERIALS AND METHODS

PCR analysis. A number of primers were designed to amplify the entire open reading frame of CBT9 from tub and wild type mice in order to identify the location of the mutation in the tub gene. The following two primers amplified different sized cDNA fragments when amplifying tub-derived versus wild type-derived nucleic acid:

PX1RSEQ ID NO: 49: 5'-TGA GAC AAA TGT CCT AGG CT-3'
  (corresponding to CBT9 base pair 1113 to 1132);
PX12RSEQ ID NO: 50): 5'-TGG ACA GAG CAA TGG CGA AG-3'
  (corresponding to CBT9 base pair 1489 to 1470)

Standard PCR conditions and sequencing procedures were utilized.

12.2. RESULTS

12.2.1. CBT9 MUTATIONAL ANALYSIS

In order to more definitively show that the CBT9 gene corresponded to the tub gene, a PCR study was conducted to define the mutation causing the CBT9 transcript size change observed in tub mice relative to the CBT9 transcript size observed in RNA of wild type mice. Of the PCR primer pairs utilized, only one resulted in a size differential between the fragment amplified using tub-derived nucleic acid and the fragment amplified using wild type-derived nucleic acid (see Section 10.1 for details).

Specifically, utilizing this primer pair (i.e., PX1R and PX12R) a cDNA was amplified from wild type (C57BL/6J) brain RNA which was about 350 bp, while a cDNA fragment was amplified from tub brain RNA which was about 800 bp. The amplification of both wild type (C57BL/6J) and tub genomic DNA resulted in a band of approximately 900 bp.

It should be noted that the size differential, approximately 450 bp, between the tub and wild type cDNA amplified fragments roughly corresponds to the difference in transcript size (i.e., 7 vs. 7.5 kb) observed between tub and wild type RNA in the CBT9 Northern analysis described, above, in the Example presented in Section 9. By sequencing (see below) it was determined that the precise size difference between the tub and wild type cDNA amplified sequences was 398 bp.

The 900 bp fragment amplified from genomic DNA reveals the presence of a second intron within the amplified region. Only one of these introns (of approximately 100 bp in length) was processed correctly in the tub animals, as discussed below.

The cDNA and genomic amplified fragments in the region of the mutation were sequenced and the wild type- and tub-derived sequences were aligned, as shown in FIG. 7A–7D. For orientation of the genomic sequence depicted in FIG. 7A–7D with the full length CBT9 cDNA coding sequence shown in FIG. 6A–6D, bases 1–12 and 411–437 in FIG. 7A–7D correspond to bases 1373–1384 and 1385–1411 of FIG. 6A–6D. In FIG. 7A–7D, the two top sequences are from genomic DNA derived from tub and wild type C57BL/6J mice, as indicated. The bottom two sequences are derived from cDNA from tub and wild type mice, as indicated. The vertical arrow shows the position of the tub mutation. The horizontal box indicates the consensus splice site sequence in C57BL/6J which is abolished in the tub genomic DNA. The asterisks indicate the intron which is erroneously not spliced out of the mature tub mRNA.

The portion of the CBT9 gene sequence in FIG. 7A–7D depicts only the genomic region near the mutation site. This alignment revealed a single base pair difference of a G to T transversion in the first base of the splice site (GTGACT; see boxed region of FIG. 1) of the intron between base 1384 and 1385 of the open reading frame of the genomic DNA. This mutation abolishes the splice site, resulting in retention of an intron of approximately 450 bp in the amplified cDNA derived from the tub RNA. To confirm that the identified sequence change did not simply represent a polymorphism, the splice site was sequenced in 32 additional mouse strains. In each of the strains, the DNA sequence at the putative mutation site was identical to that observed in the wild type C57BL/6J strain.

Figure 8:
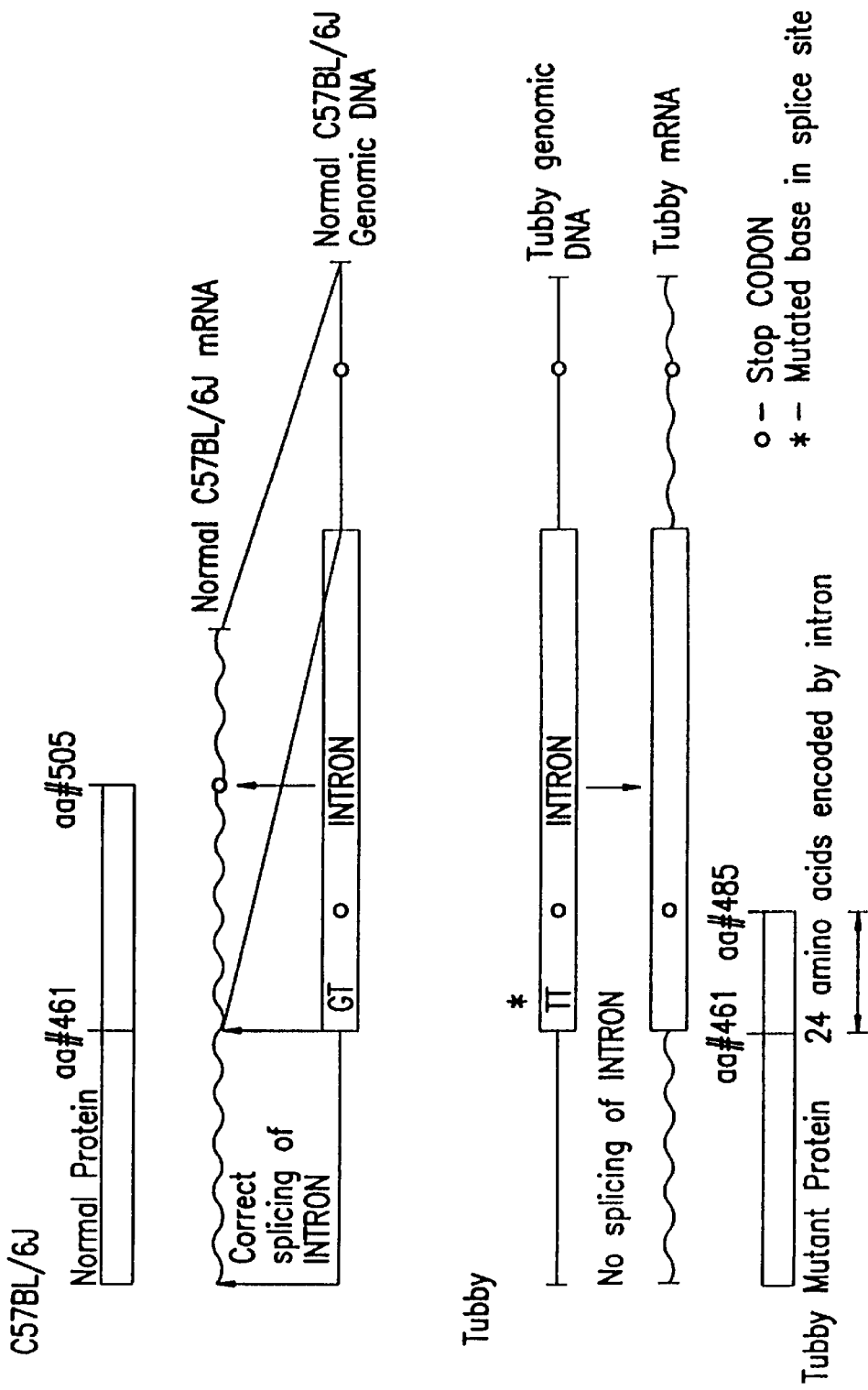
FIG. 8. Schematic representation of the splicing defect in the CBT9 gene in tub animals.

FIG. 8 depicts a schematic representation of the splicing defect within the CBT9 in tub mice. The top half of the figure shows the normal, wild type splicing of the intron from C57BL/6J RNA and the predicted carboxy terminus of the wild type CBT9 protein. The G to T mutation of the first base of the intron within the CBT9 gene in tub mice abolishes splicing of this intron, causing the intron to be retained within the mature mRNA. The predicted tub mutant CBT9 protein, therefore, is abnormal. Specifically, due to translation of intronic sequence, this mutant tub gene product lacks the final 44 amino acid residues of the normal CBT9 protein and, instead, contains 24 intron-encoded amino acid residues at its carboxy terminus which are erroneously added to the tub protein until a stop codon within the intronic sequence is reached.

12.2.2. CBT9 NUCLEOTIDE AND AMINO ACID SEQUENCE

As discussed in Section 8.2, above, the fumh019 CBT9 cDNA clone was sequenced. Sequencing revealed that the fumh019 cDNA clone contained the entire CBT9 open reading frame.

The nucleotide sequence and amino acid sequence of CBT9 is shown in FIG. 6A–6D. The CBT9-encoded protein is 505 amino acid residues in length. CBT9 is a novel gene, with no identical sequences present in published databases. The entire CBT9 coding region of the Mus spretus and A/J mouse strains were sequenced and no non-conservative amino acid changes in either strain as compared to the C57BL/6J tub sequence were found.

The CBT9 gene product is a hydrophilic protein, with an estimated pI of 9.2, which lacks any obvious secretary sequence, mitochondrial transit peptide or transmembrane domain. The gene product contains a region consisting of two runs of serine amino acid residues separated by eight acidic amino acid residues (amino acid residues 191–211), which could serve as a hinge between domains of the protein. In addition, two potential dibasic protease cleavage sites are present at amino acid positions 302 and 383, and two potential glycosylation sites are present at amino acid positions 205 and 426.

The carboxy half of the CBT9 gene product shows similarity to several sequences in the public protein databases and/or encoded by sequences present in public nucleotide databases, including p4–6, a mouse testis cDNA (Genbank X69827); F10B5.4 (Genbank Z48334), a *C. elegans* genomic sequence; DM87D3S (Genbank Z50688) a Drosophila STS; and ys86c04.r1 (Genbank H92408), a human retinal cDNA; as well as several rice, maize and Arabidopsis ESTs. With the exception of the mouse testis cDNA p4–6, none of these sequences has been functionally characterized. p4–6 was isolated by screening of a cDNA library with a rat phosphodiesterase probe (Vambutas, V. & Wolgemuth, D. J. 1994, Biochim. Biophys. Acta 1217: 203–206).

Upon alignment of the CBT9 gene product and the sequences showing similarity to CBT9, certain regions were shown to be completely conserved. Specifically, the two dibasic protease cleavage amino acid residues and the cysteine amino acid at the penultimate CBT9 position are all completely conserved among all the CBT9-related sequences.

The data presented in Sections 6 to 11 above, including mapping data, and Northern and in situ analyses, and the mutational analysis data presented in this Section demonstrating that the tubby phenotype is associated with a splicing defect within the CBT9 gene which results in a major alteration of the carboxy terminus of the CBT9 gene product, represent conclusive evidence that the CBT9 gene is the tub gene. Specifically, CBT9 maps within the 0.25 cM interval that the tub gene has been shown, herein, to map. Further, the CBT9 gene is expressed in the brain, including the hypothalamus, a region known to be involved in body weight control. Additionally, the CBT9 transcript in tub animals is larger than the CBT9 transcript found in wild type C57BL/6J animals and it has been shown herein that this increase in size is due to a single base mutation in a CBT9 splice site which results in the incorrect splicing of the RNA such that a 398 nucleotide intron remains within the mature mRNA. As a result, the protein which is translated from such a mutant transcript exhibits an abnormal carboxy terminus. Presumably as a result of this defect, the CBT9 mRNA is upregulated approximately 5-fold in homozygous tub/tub mice. The heterozygous tub/+ mice showed a more modest upregulation, as would be expected, given the heterozygous tub phenotype. In summary, therefore, the CBT9 gene has successfully been identified to be the tub gene.

13. EXAMPLE: CLONING AND CHARACTERIZATION OF THE HUMAN tub GENE

The Example presented herein describes the successful cloning and characterization of the human tub gene, which is involved in the control of human body weight. Both the human tub gene and gene product exhibit a striking level of similarity to the murine tub gene and gene product.

13.1. MATERIALS AND METHODS

P8X5-1 tub probe generation: The 950 base pair P8X5-1 tub gene cDNA probe was generated by standard PCR amplification of the murine cDNA clone fumh019, described, above, in Section 8. The following primers were utilized for the amplification:

P8X5R1(SEQ ID NO: 51): 5'-CCG ACT CGA TTG CCA GTG TA -3'
P8X1F1(SEQ ID NO: 52): 5'-GCG GAT ACA GAC TCT CTC AT -3'

Upon amplification, the probe was gel purified and radiolabelled according to standard protocols.

cDNA screening: Screening was performed on a human fetal brain cDNA library (Clontech #HL1149x). Hybridization was performed for 4 hours at 65° C. using Amersham Rapid Hyb buffer (Cat. # RPN1639) according to the manufacturer's protocol. A final washing stringency of 1.0×SSC/ 0.1% SDS at 50° C. for 20 minutes was achieved. Autoradiography was performed overnight.

DNA sequencing: Standard DNA sequencing techniques were utilized for the sequencing of the resulting putative human tub CDNA clones.

13.2 RESULTS

The 950 base pair P8X5-1 murine tub gene probe, described, above, in Section 13.1, was used to screen a human fetal brain cDNA library for clones corresponding to the human tub gene. Screening conditions were as described, above, in Section 13.1.

Screening of the human cDNA library yielded thirteen independent positive clones. Among these clones were those designated CBT9H1, CBT9H2 and CBT9H3, which have been deposited with the ATCC. Sequencing revealed that the entire coding region of the human tub gene was contained within these partially overlapping clones.

The nucleotide and derived amino acid sequences of the human tub gene are shown in FIG. 9A–9D. As shown in FIG. 9A–9D, the human tub gene encodes a 506 amino acid protein. The human tub gene product encodes a hydrophilic protein exhibiting an estimated pI of 9.2 which lacks any obvious secretory sequence, mitochondrial transit peptide or transmembrane domain. The gene product contains a region consisting of two runs of serine amino acid residues separated by a acidic amino acid residues (amino acid 191–211) which could serve as a hinge between domains of the protein. In addition, there are two potential dibasic protease cleavage sites at amino acid positions 301–306 and 381–384, as well as two potential N-glycosylation sites at amino acid residues 206 and 427.

The human tub gene and gene product exhibit a striking similarity to the murine tub gene and gene product. Specifically, the human tub gene is 89% identical, at the nucleotide level, to the murine tub gene. Further, the 506 amino acid human tub gene product exhibits a 94% identity to the 505 amino acid murine tub gene product. Amino acid residue 201 represents the only amino acid insertion between the two tub gene product sequences. Specifically, the human tub amino acid residue 201 corresponds to an insertion between murine amino acid residues 200 and 201. The carboxy half of the tub gene product is particularly highly conserved. The final 260 amino acid residues of the human and mouse tub gene products differ by only a single residue. Specifically, murine tub gene product amino acid residue 399 is a cysteine, while the corresponding human tub gene product amino acid residue 400 is serine.

In summary, the results presented herein represent the successful cloning of the human tub gene.

14. EXAMPLE: HUMAN AND MURINE tub GENE ALTERNATIVE SPLICING

The Example presented herein describes the discovery that both the human and murine tub genes produce alternatively spliced transcripts. Specifically, it is shown that tub transcripts are produced which either contain or are lacking the sequence corresponding to tub exon 5. Quantitative variation between the relative amounts of alternatively spliced species produced is also described.

14.1. MATERIAL AND METHODS

RT-PCR. First strand cDNA was synthesized from total RNA using SuperScript (Gibco-BRL) according to supplier's protocol. Subsequent PCR conditions were as follows: Hot start with 0.5U AmpliTaq, followed by 30 cycles at 94° C. for 1 minute, 55° C. for 1 minute and 72° C. for 1 minute. Products were electrophoresed on 2% agarose gels. RT-PCR products to be sequenced were run on LMP agarose, excised, digested with β-Agarase (New England Biolabs), precipitated and resuspended in water. The same conditions were utilized for amplification of both human and mouse RNA populations.

The primers utilized for mouse sequence amplification were derived from murine tub exons 4 and 6:

P8X5R(SEQ ID NO: 53):   5'-CCG ACT CGA TTG CCA GTG TA -3';  and
CBT9R5(SEQ ID NO: 54):  5'-GGA GCT GTT TTC ATC CTC ATC -3'.

The primers utilized for human sequence amplification were derived from human tub exons 4 and 6:

hCBT9F11(SEQ ID NO: 55):  5'-GAA GGA GAA GAA GGG AAA GC-3';  and
hCBT9R11(SEQ ID NO: 56):  5'-GGG TGT TAC TAT TTA GCT GG-3'.

Other techniques. All other techniques were performed according to standard procedures and/or as described in the Examples presented above. Primers used for genomic PCR amplification were derived from tub exons 4 and 5:

X4F1(SEQ ID NO: 57):  5'-TTC AAG AGG CCG ACT CGA TT -3'; and
X5R1(SEQ ID NO: 58):  5'-TTC CTC TGC ATC GTG GCA C -3'.

14.2. RESULTS

RT-PCR from mouse brain RNA using primers derived from exons 4 and 6, as described in Section 14.1, above, resulted in the amplification of two products. Sequencing of these products showed that they differ by the presence or absence of sequence corresponding to exon 5. RT-PCR of RNA from C57BL/6J mice consistently yielded more of the amplified product containing exon 5. This result was shown to be true for 7 other strains tested.

RT-PCR performed using brain RNA derived from the Mus spretus strain, however, invariably showed a greater abundance of the product lacking exon 5. This was demonstrated in 6 independent *M. spretus* mice. This quantitative pattern was also found to be exhibited in *M. castaneous* mice. Genomic PCR revealed that the intron preceding exon 5 was 0.5 kb shorter in both *M. spretus* and *M. castaneous* strains. Sequencing of a portion of this intron showed that its donor, acceptor and branch point sequences were not affected by the sequence missing in these strains.

RT-PCR of total human RNA from several tissues was performed with two primers from exons 4 and 6 using the same conditions as for mouse RNA. The amplification primers were hCBT9F11 and hCBT9R11, as described, above, in Section 14.1. Amplification produced two amplified fragments of 281 bp and 113 bp. Sequencing revealed that the larger band represented a transcript containing exon 5, while the smaller fragment was missing the sequence corresponding to exon 5. Thus, the human tub gene, also exhibits alternate splicing of exon 5. Both the human and mouse exon 5 is 168 base pairs long. Because this length is a multiple of 3, the reading frame of the transcripts lacking exon 5 is conserved.

It is possible that variant splicing may result in proteins with qualitatively or quantitatively distinct activities. The differential regulation of alternate splicing may result in individuals with differential susceptibilities to obesity. For example, in place of the constitutive obesity associated with the tub mutation, alleles which yield a higher amount of protein encoded by transcripts lacking exon 5 relative to the level encoded by transcripts containing exon 5 may confer a greater susceptibility to obesity only in the context of a particular environmental and genetic background.

15. EXAMPLE: RECOMBINANT EXPRESSION OF tub GENE PRODUCTS

The Example presented in this Section describes the recombinant expression of murine and human tub gene products.

15.1. MATERIALS AND METHODS

Bacterial expression.

Murine tub subcloning. cDNA sequence containing the entire murine tub coding region was subcloned into bacterial expression vector pET29*. pET29* is a modified pET29a vector (Novagen, Inc., Madison, Wis.) containing an altered Shine-Dalgarno sequence for optimal initiation of translation (Chen, H. et al., 1994, Nuc. Acids Res. 22:4953–4957).

In order to subclone the tub coding sequence into the pET29* vector, site directed mutagenesis was performed on an existing tub cDNA to create a tub sequence with appropriate restriction sites. Specifically, single stranded DNA was rescued from CJ 236 E. coli transformed with pMal-c2 (New England Biolabs, Beverley, Mass.) plasmid containing a PCR-derived tub CDNA by infection with K07 M13 helper phage. The single stranded DNA was used as a template for site directed mutagenesis which yielded amplified tub fragments containing altered ends (Kunkel, T. A., 1985, Proc. Natl. Acad. Sci. USA 82:488–491). The 5' end of the amplified fragment was altered such that the tub initiation codon was contained within an NdeI site (i.e., CATATG), while the 3' end was altered such that part of the tub termination codon was contained within an EcoRI site (i.e., TGAATTC). The resulting tub cDNA was excised as a 5' NdeI to 3' EcoRI fragment and ligated into NdeI/EcoRI-digested pET29* vector, to yield the murine pET29*-tub expression construct.

In order to produce the murine tub-HIS$_6$ expression construct, codons for six histidine residues were fused in-frame at the 3' end of the tub cDNA sequence. Site directed mutagenesis was employed as described above, except that the primers utilized yielded fragments containing the six histidine codons inserted just 5' of the EcoRI site at the 3' end of the CDNA (i.e., CACCACCACCACCACCACTGAATTC) (SEQ ID NO:59). The resulting mutagenized fragment was excised and ligated into pET29* as described above to yield the murine pET29*-tub-HIS$_6$ expression construct.

Human tub subcloning. The entire coding region of the human tub sequence was also inserted into the pET29* expression vector in both native and HIS$_6$ fusion forms. For insertion into pET29*, a human tub cDNA in pMal-C2 was modified via site directed mutagenesis to create 5' NdeI and 3' EcoRI restriction sites, as described for the murine tub sequence, above, to yield the human pET29*-tub expression construct.

For construction of the human tub HIS$_6$ construct, six histidine codons were introduced just 5' of the EcoRI site by a three part ligation. Specifically, a 5' ApaLI - 3' EcoRI restriction fragment encoding the last 25 amino acids of the murine pET29*-tub-HIS$_6$ was exchanged for the equivalent fragment of the human tub gene sequence in human pET29*-tub construct, to yield the human pET29*-tub-HIS$_6$ expression construct. It should be noted that, although the human and mouse tub genes have differing primary sequences, the amino acid residues they encode within this carboxy-terminal region are identical.

Expression of recombinant tub proteins. Host bacteria BL21(DE3) (Novagen, Inc., Madison, Wis.) were chemically transformed with each of the expression constructs described above (i.e., murine pET29*-tub, murine pET29*-tub-HIS$_6$, human pET29*-tub or human pET29*-tub-HIS$_6$) and grown in 6 liters BHI (Brain Heart Infusion broth) cultures to mid-log phase ($OD_{595}$=1.0) at 37° C.

T7 RNA polymerase and, concomitantly, tub protein expression, was induced by the addition of IPTG to a final concentration of 0.5 mM. Two hours post-induction, bacteria were collected by centrifugation and frozen.

Mammalian expression.

Murine tub subcloning. To prepare murine tub cDNA containing the entire tub coding region, the 5' end of the murine tub cDNA in the murine pET29*-tub construct was mutagenized to remove the NdeI restriction site, and replaced with a BamHI restriction site and a Kozak box (Kozak, M. 1987, Nuc. Acid Res. 15:8125–8132) for efficient initiation of translation in mammalian cells. After modification, the sequence just 5' of the tub start codon was as follows: GGATCCACCATG (the start codon is underlined).

The modified sequence was digested with BamHI and EcoRI to excise the region to be subcloned. After excision, the murine tub cDNA was ligated into the transient expression vector pN8ε (to yield the pN8E-tub construct) and into the stable retroviral expression vector pWZLblast (to yield the pWZLblast-tub construct). Transcription in pN8ε is directed from the human CMV immediate early promoter, while transcription from pWZLblast is initiated in the promoter embedded Moloney Leukemia Virus LTR.

Constructs for the expression of epitope tagged recombinant tub gene product were generated, in which a DNA fragment encoding three tandem copies of the influenza virus hemagglutinin peptide YPYDVPDYA was fused in-frame with the $NH_2$ terminus of the tub cDNA in pN8ε-tub. Specifically, the triple flu epitope was amplified from the plasmid pBS HA$^3$ via PCR with primers possessing 5' HindIII and 3' BamHI restriction sites. The PCR product was purified, HindIII/BamHI digested and ligated into HindIII/BamHI digested pN8ε-tub. The correct sequence of the fusion construct (designated pN8ε3Xflu-tub) was verified.

Expression of recombinant tub proteins. Transient expression is achieved by transfection of pN8ε-tub or pN8ε3Xflu-tub expression constructs into 293 EBNA cells (Invitrogen Corp.) via lipofection (Lipofectamine; Life Technologies Corp.). Analyses performed 72 hours post-lipofection.

Stably infected polyclonal pools of NIH 3T3 cells harboring pWLZblast-tub proviruses are generated by transiently transfecting ΩE producer cells (Morgenstern, J. P. & Land, H., 1990, Nuc. Acids Res. 18:3587–3596) with calcium phosphate and harvesting recombinant retrovirus 48 hours later. The virus is then used to infect target NIH 3T3 fibroblasts overnight at which time the infected cells are split 1:10 into medium supplemented with blasticidin HCl (ICN Corp.) at a concentration of 10 μg/ml. Colonies of blasticidinS HCl-resistant cells which appear within roughly two weeks are pooled and lysed for analysis.

15.2. RESULTS

Described herein is the successful expression of recombinant murine and human tub gene products in mammalian and/or bacterial systems. With respect to bacterial expression, both native and $HIS_6$ fusion (i.e., a fusion protein containing six carboxy-terminal histidine amino acid residues following the native tub amino acid sequence) tub gene products have been expressed. Details regarding the creation of tub expression constructs and production of gene products using these constructs are described, above, in Section 15.1.

Figure 11:
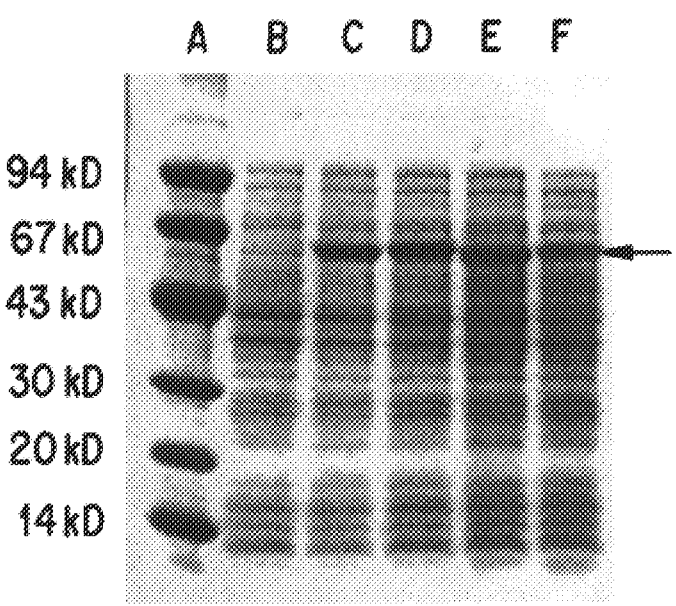
FIG. 11. SDS polyacrylamide protein gel demonstrating bacterial expression of recombinant murine and human tub gene products. Lanes from left to right: Pharmacia Low Molecular Weight Markers; uninduced BL21DE3/human pET29*-tub; induced BL21DE3/human pET29*-tub; induced BL21DE3/ human pET29*-tub HIS$_6$; induced BL21DE3/murine pET29*-tub; induced BL21DE3/murine pET29*-tub HIS$_6$. Arrow represents recombinant tub gene products.

Aliquots of bacterial lysates (representing approximately $10^{-5}$ of the total 6 liter preparation were analyzed using standard SDS polyacrylamide gel electrophoresis, as depicted in FIG. 11. A protein with a molecular weight of approximately 57 kD was readily apparent in proteins obtained from induced bacteria containing murine pET29*-tub. 57 kD was the approximate molecular weight one would predict for the murine tub protein, with its 505 amino acid residues. Likewise, a protein with a molecular weight of approximately 57 kD was readily apparent in proteins obtained from induced bacteria containing human pET29*-tub. 57 kD was the approximate molecular weight one would predict for the 506 amino acid residue human tub gene product.

A protein exhibiting a slightly increased molecular weight was readily apparent in proteins obtained from induced bacteria containing either human or murine pET29*-$HIS_6$. The slight increase in molecular weight was expected given the additional six histidine residues present in these tub-$HIS_6$ fusion proteins.

Constructs for the expression of epitope-tagged murine tub protein were utilized to demonstrate successful mammalian expression of recombinant tub gene product. Specifically, the pN8ε3Xflu-tub expression construct was introduced, via lipofection, into 293 EBNA cells, as described, above, in Section 15.1. After lipofection, immunoprecipitation followed by Western blot detection with the monoclonal antibody 12CA5 (directed against the flu hemagglutinin peptide; Boehringer Mannhein Corp.) was performed. Western blotting revealed the presence of a protein exhibiting a molecular weight of approximately 59 kD (i.e., a size expected of the full length tub gene product fused the triple flu hemagglutinin peptide sequence). No such protein was detected in control transfections with non-hemagglutinin tagged pN8ε-tub constructs.

In summary, the results described herein indicate that recombinant murine and human tub gene products have successfully been expressed in bacterial and/or mammalian systems.

16. EXAMPLE: IDENTIFICATION AND CHARACTERIZATION OF A tub GENE HOMOLOG

The Example presented in this Section describes the identification and characterization of a human tub gene homolog, referred to herein as human tub homolog 1.

The mouse tub gene nucleotide sequence was utilized as a database query using the Blastx program (1993, Nature Genetics 3:266–272), which resulted in the identification of a human EST (GenBank Accession No. H92408) which exhibited a 75.3% identity over 85 derived amino acid residues. The EST was originally derived from a human retinal library (Soares, B. and Benaldo, F.).

Upon identification of the EST, the corresponding clone was obtained from Genbank and sequenced. A number of errors in the sequence listed in the database were found. These included a deletion of bp 33 from the Genbank sequence, incorrect base pair insertions (Genbank sequence bps 330, 339, 359, 366, 375 and 384), incorrect sequence at bps 133–137 (ACCGA in Genbank sequence, as opposed to the correct GGCCG sequence) and incorrect bp 398 (T in Genbank as opposed to the correct G).

The identified sequence was used to screen a retinal cDNA library, which resulted in the identification of several positive clones. FIG. 12A–12C depicts nucleotide sequence of the tub homolog identified via this screening effort, which is referred to herein as human tub homolog 1. The sequence depicted in FIG. 12A–12C codes for a substantial portion of the human tub homolog 1 protein, the derived amino acid sequence of which is also depicted in FIG. 12A–12C. The sequence exhibits a 73.9% identity over 216 derived amino acid residues.

The EST derived from the human tub homolog 1 gene was mapped in the human by PCR typing of the Genebridge (G4) radiation hybridization panel. Typing of the DNA and comparison to radiation hybrid map data at the Whitehead Institute Center for Genome Research (WICGR) tightly linked the EST to an anonymous STS, WI-4186, on human chromosome 6.

Additionally, the EST was genetically mapped in the mouse using a C57BL/6J×Mus spretus interspecific backcross. Genotyping of 100 meioses demonstrated linkage to a region on mouse chromosome 17 between D17Mit48 and D7Mit 9.

Human multiple tissue northern blots (Cat. No. 7766-1 and 7760-1; Clonetech, Palo Alto, Calif.) containing 2 μg of poly A+ RNA per lane were probed with the approximately 1.35 kb EcoRI - NotI fragment of the sequence obtained from Genbank containing the human tub homolog 1 insert. The filters were prehybridized in 5 mls of Church buffer at 65° C. for 1 hour, after which 100 ng of $^{32}$P-labelled probe was added. Probe was made using Stratagene Prime-It kit (Cat. No. 300392; Stratagene, La Jolla, Calif.). Hybridization was allowed to proceed at 65° C. for approximately 18 hours. Final washes of the filters was in 0.1% SDS, 0.2×SSC solution for 65° C. Washed filters were exposed to a phosphoimager for 4 hours.

The Northern analysis was performed using a 1.35 kb probe as described in Section 16.1, above, containing human tub homolog 1 sequence encoding 285 amino acids plus 3'-untranslated sequence to the poly-A sequence was performed. Tissues tested included brain, lung, liver, kidney, spleen, thymus, muscle, prostate, testis and fat. A message of approximately 2 kb was apparent in the lanes containing RNA from skeletal muscle and testis.

17. DEPOSIT OF MICROORGANISMS

The following microorganisms were deposited under the provisions of the Budapest Treaty on the International Recognition of the Deposit of Microorganisms for the Purposes of Patent Procedure, and comply with the criteria set forth in 37 C.F.R. §1.801–1.809 regarding availability and permanency of deposits. The microorganisms were deposited with the American Type Culture Collection (ATCC), Rockville, Md., on the dates indicated and were assigned the indicated accession numbers:

| Microorganism | Clone | ATCC Access. No. | Deposit Date |
|---|---|---|---|
| H019 (*E. coli*) | fumh019 | 69856 | June 29, 1995 |
| E/P8 (*E. coli*) | P8 | 69858 | June 30, 1995 |
| E/P6 (*E. coli*) | P6 | 69857 | June 30, 1995 |
| E/B13 (*E. coli*) | B13 | 69859 | June 30, 1995 |
| CBT9H1 (*E. coli*) | CBT9H1 | 97222 | July 10, 1995 |
| CBT9H2 (*E. coli*) | CBT9H2 | 97221 | July 10, 1995 |
| CBT9H3 (*E. coli*) | CBT9H3 | 69874 | July 28, 1995 |

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

---

What is claimed is:

1. An isolated polypeptide comprising:

(a) the amino acid sequence shown in SEQ ID NO:2;

(b) the amino acid sequence shown in SEQ ID NO:8;

(c) an amino acid sequence encoded by the nucleic acid insert of the clone contained in ATCC Deposit No. 69856;

(d) the amino acid sequence encoded by the nucleic acid insert of the clone contained in ATCC Deposit No. 97222;

(e) the amino acid sequence encoded by the nucleic acid insert of the clone contained in ATCC Deposit No. 97221;

(f) the amino acid sequence encoded by the nucleic acid insert of the clone contained in ATCC Deposit No. 69874;

(g) an amino acid sequence encoded by the nucleic acid insert of the clone contained in ATCC Deposit No. 69857;

(h) an amino acid sequence encoded by the nucleic acid insert of the clone contained in ATCC Deposit No. 69858; or (i) an amino acid sequence encoded by the nucleic acid insert of the clone contained in ATCC Deposit No. 69859.

2. The isolated polypeptide of claim 1 wherein the polypeptide comprises the amino acid sequence shown in SEQ ID NO:2.

3. The isolated polypeptide of claim 1 wherein the polypeptide comprises the amino acid sequence shown in SEQ ID NO:8.

4. The isolated polypeptide of claim 1 wherein the polypeptide comprises the amino acid sequence encoded by the nucleic acid insert of the clone contained in ATCC Deposit No. 69856.

5. The isolated polypeptide of claim 1 wherein the polypeptide comprises the amino acid sequence encoded by the nucleic acid insert of the clone contained in ATCC Deposit No. 97222.

6. The isolated polypeptide of claim 1 wherein the polypeptide comprises the amino acid sequence encoded by the nucleic acid insert of the clone contained in ATCC Deposit No. 97221.

7. The isolated polypeptide of claim 1 wherein the polypeptide comprises the amino acid sequence encoded by the nucleic acid insert of the clone contained in ATCC Deposit No. 69874.

8. The isolated polypeptide of claim 1 wherein the polypeptide comprises an amino acid sequence encoded by the nucleic acid insert of the clone contained in ATCC Deposit No. 69857.

9. The isolated polypeptide of claim 1 wherein the polypeptide comprises an amino acid sequence encoded by the nucleic acid insert of the clone contained in ATCC Deposit No. 69858.

10. The isolated polypeptide of claim 1 wherein the polypeptide comprises an amino acid sequence encoded by the nucleic acid insert of the clone contained in ATCC Deposit No. 69859.

11. An isolated polypeptide comprising:

(a) amino acid residues 1–133 shown in SEQ ID NO:2;

(b) amino acid residues 190–505 shown in SEQ ID NO:2;

(c) amino acid residues 1–133 and 190–505 shown in SEQ ID NO:2;

(d) amino acid residues 1–133 shown in SEQ ID NO:8;

(e) amino acid residues 190–506 shown in SEQ ID NO:8; or (f) amino acid residues 1–133 and 190–506 shown in SEQ ID NO:8.

12. The isolated polypeptide of claim 11 wherein the polypeptide comprises amino acid residues 1–133 shown in SEQ ID NO:2.

13. The isolated polypeptide of claim 11 wherein the polypeptide comprises amino acid residues 190–505 shown in SEQ ID NO:2.

14. The isolated polypeptide of claim 11 wherein the polypeptide comprises amino acid residues 1–133 and 190–505 shown in SEQ ID NO:2.

15. The isolated polypeptide of claim 11 wherein the polypeptide comprises amino acid residues 1–133 shown in SEQ ID No:8.

16. The isolated polypeptide of claim 11 wherein the polypeptide comprises amino acid residues 190–506 shown in SEQ ID NO:8.

17. The isolated polypeptide of claim 11 wherein the polypeptide comprises amino acid residues 1–133 and 190–506 shown in SEQ ID NO:8.

18. The isolated polypeptide of claim 14 wherein the isolated polypeptide comprises amino acid residue 133 shown in SEQ ID NO:2 attached via a peptide bond to amino acid residue 190 shown in SEQ ID NO:2 so that amino acid residues 1–133 and 190–505 shown in SEQ ID NO:2 are contiguously present within the polypeptide.

19. The isolated polypeptide of claim 17 wherein the isolated polypeptide comprises amino acid residue 133 shown in SEQ ID NO:8 attached via a peptide bond to amino acid residue 190 shown in SEQ ID No:8 so that amino acid residues 1–133 and 190–505 shown in SEQ ID No:8 are contiguously present within the polypeptide.

20. The isolated polypeptide of claim 1 further comprising a heterologous amino acid sequence.

21. The isolated polypeptide of claim 11 further comprising a heterologous amino acid sequence.

22. An isolated polypeptide comprising the amino acid sequence shown in SEQ ID NO:8.

23. An isolated polypeptide comprising an amino acid sequence encoded by the nucleic acid insert of the clone contained in ATCC Deposit No. 97222.

24. An isolated polypeptide comprising an amino acid sequence encoded by the nucleic acid insert of the clone contained in ATCC Deposit No. 97221.

25. An isolated polypeptide comprising an amino acid sequence encoded by the nucleic acid insert of the clone contained in ATCC Deposit No. 69874.

26. An isolated polypeptide comprising amino acid residues 1–133 shown in SEQ ID NO:8.

27. An isolated polypeptide comprising amino acid residues 190–506 shown in SEQ ID NO:8.

28. An isolated polypeptide comprising amino acid residues 1–133 and 190–506 shown in SEQ ID NO:8.

29. The isolated polypeptide comprising amino acid residue 133 shown in SEQ ID NO:8 attached via a peptide bond to amino acid residue 190 shown in SEQ ID NO:2 so that amino acid residues 1–133 and 190–505 shown in SEQ ID NO:8 are contiguously present within the polypeptide.

* * * * *